(12) United States Patent
Kehler et al.

(10) Patent No.: US 10,633,382 B2
(45) Date of Patent: Apr. 28, 2020

(54) IMIDAZOPYRAZINONES, PYRAZOLOPYRIMIDINONES AND PYRAZOLOPYRIDINONES AS PDE1 INHIBITORS

(71) Applicant: H. Lundbeck A/S, Valby (DK)

(72) Inventors: Jan Kehler, Lyngby (DK); Lars Kyhn Rasmussen, Vanløse (DK); Morten Langgård, Glostrup (DK); Mikkel Jessing, Frederiksberg (DK); Paulo Jorge Vieira Vital, København V (DK); Karsten Juhl, Greve (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 16/340,429

(22) PCT Filed: Oct. 17, 2017

(86) PCT No.: PCT/EP2017/076481
§ 371 (c)(1),
(2) Date: Apr. 9, 2019

(87) PCT Pub. No.: WO2018/073251
PCT Pub. Date: Apr. 26, 2018

(65) Prior Publication Data
US 2019/0308968 A1 Oct. 10, 2019

(30) Foreign Application Priority Data

Oct. 18, 2016 (DK) ................................ 2016 00643
Mar. 14, 2017 (DK) ................................ 2017 00191

(51) Int. Cl.
*C07D 471/04* (2006.01)
*C07D 487/04* (2006.01)

(52) U.S. Cl.
CPC ......... *C07D 471/04* (2013.01); *C07D 487/04* (2013.01)

(58) Field of Classification Search
CPC .................... C07D 487/041; C07D 471/04
See application file for complete search history.

(56) References Cited

U.S. PATENT DOCUMENTS

| | | | |
|---|---|---|---|
| 6,174,884 B1 * | 1/2001 | Haning | C07D 487/04 514/234.2 |
| 7,872,124 B2 | 1/2011 | Feng et al. | |
| 10,011,606 B2 | 7/2018 | Kehler et al. | |
| 10,150,771 B2 | 12/2018 | Kehler et al. | |
| 2006/0135767 A1 | 6/2006 | Feng et al. | |
| 2008/0194592 A1 | 8/2008 | Mates et al. | |
| 2009/0143391 A1 | 6/2009 | Hofgen et al. | |
| 2010/0190771 A1 | 7/2010 | Claffey et al. | |
| 2011/0281832 A1 | 11/2011 | Li et al. | |
| 2016/0083391 A1 | 3/2016 | Burdi et al. | |
| 2016/0083400 A1 | 3/2016 | Burdi et al. | |
| 2016/0311831 A1 | 10/2016 | Kehler et al. | |
| 2016/0318939 A1 | 11/2016 | Kehler et al. | |
| 2017/0291901 A1 | 10/2017 | Juhl et al. | |
| 2017/0291903 A1 | 10/2017 | Kehler et al. | |
| 2017/0298072 A1 | 10/2017 | Kehler et al. | |
| 2019/0062335 A1 | 2/2019 | Kehler et al. | |

FOREIGN PATENT DOCUMENTS

| | | |
|---|---|---|
| EP | 2305262 | 4/2011 |
| GB | 973361 | 10/1964 |
| JP | 2015-052588 | 2/2016 |
| JP | 2016-011511 | 2/2016 |
| JP | 2018-76285 A1 | 5/2018 |
| WO | WO 2004/018474 | 3/2004 |
| WO | WO 2004/026876 | 4/2004 |
| WO | WO 2004/099211 | 11/2004 |
| WO | WO 2008/070095 | 6/2008 |
| WO | WO 2008/139293 | 11/2008 |
| WO | WO 2009/121919 A1 | 10/2009 |
| WO | WO 2010/026214 A1 | 3/2010 |
| WO | WO 2010/065152 | 6/2010 |
| WO | WO 2010/084438 | 7/2010 |
| WO | WO 2011/153136 | 12/2011 |

(Continued)

OTHER PUBLICATIONS

International Search Report and Written Opinion dated Dec. 2, 2015 for Application No. PCT/EP2015/073417.
International Search Report and Written Opinion dated Jun. 2, 2016 for Application No. PCT/EP2016/058910.
International Search Report and Written Opinion dated Jul. 21, 2016 for Application No. PCT/EP2016/059583.
International Search Report and Written Opinion dated May 15, 2017 for Application No. PCT/EP2017/058332.
International Search Report and Written Opinion dated Dec. 11, 2017 for Application No. PCT/EP2017/076481.
International Search Report and Written Opinion dated Feb. 2, 2018 for Application No. PCT/EP2017/077497.

(Continued)

*Primary Examiner* — Erich A Leeser
(74) *Attorney, Agent, or Firm* — Wolf, Greenfield & Sacks, P.C.

(57) ABSTRACT

The present invention provides compounds according to formula (I) below that are PDE1 enzyme inhibitors and their use as medicaments, in particular for the treatment of neurodegenerative disorders and psychiatric disorders. The present invention also provides pharmaceutical compositions comprising compounds of the invention and methods of treating disorders using the compounds of the invention.

(I)

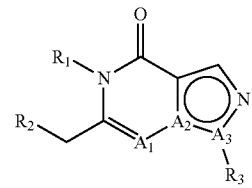

16 Claims, No Drawings

(56) References Cited

FOREIGN PATENT DOCUMENTS

| WO | WO 2012/040048 | | 3/2012 |
|---|---|---|---|
| WO | WO 2012/040230 | | 3/2012 |
| WO | WO 2012/065612 | A1 | 5/2012 |
| WO | WO 2012/171016 | | 12/2012 |
| WO | WO 2013/053690 | | 4/2013 |
| WO | WO 2013/110768 | | 8/2013 |
| WO | WO 2013/192225 | A1 | 12/2013 |
| WO | WO 2013/192229 | A1 | 12/2013 |
| WO | WO 2014/151409 | | 9/2014 |
| WO | WO 2016/042775 | | 3/2016 |
| WO | WO 2016/055618 | | 4/2016 |
| WO | WO 2016/147659 | | 9/2016 |
| WO | WO 2016/170064 | A1 | 10/2016 |
| WO | WO 2016/174188 | | 11/2016 |
| WO | WO 2017/139186 | A1 | 8/2017 |
| WO | WO 2018/073251 | A1 | 4/2018 |
| WO | WO 2018/078038 | A1 | 5/2018 |
| WO | WO 2018/078042 | A1 | 5/2018 |

OTHER PUBLICATIONS

International Search Report and Written Opinion dated Feb. 7, 2018 for Application No. PCT/EP2017/077503.
[No Author Listed] FDA mulls drug to slow late-stage Alzheimer's. CNN Health. Sep. 24, 2003; http://www.cnn.com/2003/HEALTH/conditions/09/24/alzheimers.drug.ap/index.html [obtained Oct. 9, 2010].
Berge et al., Pharmaceutical Salts. J Pharm Sci. Jan. 1977;66(1):1-19.
Bernard et al., Transcriptional architecture of the primate neocortex. Neuron. Mar. 22, 2012;73(6):1083-99. doi: 10.1016/j.neuron.2012.03.002.
Blokland et al., PDE inhibition and cognition enhancement. Expert Opin Ther Pat. Apr. 2012;22(4):349-54. doi: 10.1517/13543776.2012.674514.
CAS Registry No. 1296334-75-2 (May 18, 2011).
Chan et al., PD E1 Isozymes, Key Regulators of Pathological Vascular Remodeling. Curr. Opin. Pharmacol. 2011; 11(6):720-724.
Damasio et al., Alzheimer's Disease and Related Dementias. Cecil Textbook of Medicine. 20th edition. 1996;2:1992-1996.
Finlander et al., Phosphorus Pentoxide in Organic Synthesis V. Phosphorus Pentoxide and Amine Hydrochlorides as Reagents in the Synthesis of 1,5-dihydro-l-methyl-4H-pyrazolo[3,4-dlpyrimidin-4-ones. Chemica Scripta. 1983;22(4):171-176 (Chemical Abstracts Only).
Francis et al., Mammalian cyclic nucleotide phosphodiesterases: molecular mechanisms and physiological functions. Physiol. Rev. Apr. 2011;91(2):651-90. doi: 10.1152/physrev.00030.2010.
Medina, (2011) Therapeutic Utility of Phosphodiesterase Type I Inhibitors in Neurological Conditions. Front Neurosci. 2011; 5:21. Published online Feb. 18, 2011. Prepublished online Jan. 19, 2011. doi: 10.3389/fnins.2011.00021.
U.S. Appl. No. 15/517,348, filed Apr. 6, 2017, Granted, U.S. Pat. No. 10,150,771.
U.S. Appl. No. 15/481,083, filed Apr. 6, 2017, Abandoned, 2017-0291901.
U.S. Appl. No. 16/051,612, filed Aug. 1, 2018, Pending.
U.S. Appl. No. 15/142,116, filed Apr. 29, 2016, Abandoned, 2016-0318939.
U.S. Appl. No. 15/615,380, filed Jun. 6, 2017, Granted, U.S. Pat. No. 10,011,606.
U.S. Appl. No. 16/002,116, filed Jun. 7, 2018, Published, 2019-0062335.
U.S. Appl. No. 16/345,136, filed Apr. 25, 2019, Pending.
U.S. Appl. No. 16/345,157, filed Apr. 25, 2019, Pending.
PCT/EP2015/073417, Dec. 2, 2015, International Search Report and Written Opinion.
PCT/EP2016/058910, Jun. 2, 2016, International Search Report and Written Opinion.
PCT/EP2016/059583, Jul. 21, 2016, International Search Report and Written Opinion.
PCT/EP2017/058332, May 15, 2017, International Search Report and Written Opinion.
PCT/EP2017/076481, Dec. 11, 2017, International Search Report and Written Opinion.
PCT/EP2017/077497, Feb. 2, 2018, International Search Report and Written Opinion.
PCT/EP2017/077503, Feb. 7, 2018, International Search Report and Written Opinion.

* cited by examiner

IMIDAZOPYRAZINONES, PYRAZOLOPYRIMIDINONES AND PYRAZOLOPYRIDINONES AS PDE1 INHIBITORS

CROSS REFERENCE TO RELATED APPLICATIONS

This Application is a National Stage filing under 35 U.S.C. 371 of International Patent Application No. PCT/EP2017/076481, filed Oct. 17, 2017, which claims foreign priority benefits are claimed under 35 U.S.C. § 119(a)-(d) or 35 U.S.C. § 365(b) of Danish application Number PA201700191, filed Mar. 14, 2017, and Danish Application Number PA201600643, filed Oct. 18, 2016. The entire contents of these applications are incorporated herein by reference in their entirety.

FIELD OF THE INVENTION

The present invention provides compounds that are PDE1 enzyme inhibitors and their use as medicaments, in particular for the treatment of neurodegenerative disorders and psychiatric disorders. The present invention also provides pharmaceutical compositions comprising compounds of the invention and methods of treating disorders using the compounds of the invention.

BACKGROUND OF THE INVENTION

The second messenger cyclic Nucleotides (cNs), cyclic adenosine monophosphate (cAMP) and cyclic guanosine monophosphate (cGMP) play a major role in intracellular signal transduction cascade, by regulating cN-dependent protein kinases (PKA and PKG), EPACs (Exchange Protein Activated by cAMP), phosphoprotein phosphatases, and/or cN-gated cation channels. In neurons, this includes the activation of cAMP- and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by phosphodiesterases (PDEs, EC 3.1.4.17). PDEs are bimetallic hydrolases that inactivate cAMP/cGMP by catalytic hydrolysis of the 3'-ester bond, forming the inactive 5'-monophosphate. Since PDEs provide the only means of degrading the cyclic nucleotides cAMP and cGMP in cells, PDEs play an essential role in cyclic nucleotide signalling. The catalytic activities of PDEs provide for breakdown of cNs over a spectrum of cN-concentrations in all cells, and their varied regulatory mechanisms provide for integration and crosstalk with myriads of signalling pathways. Particular PDEs are targeted to discrete compartments within cells where they control cN level and sculpt microenvironments for a variety of cN signalosomes (Sharron H. Francis, Mitsi A. Blount, and Jackie D. Corbin. Physiol Rev 2011, 91, 651-690).

On the basis of substrate specificity, the PDE families can be divided into three groups: 1) The cAMP-specific PDEs, which include PDE4, PDE7, and PDE8, 2) the cGMP-selective enzymes PDE5 and PDE9, and 3) the dual-substrate PDEs, PDE1, PDE2, PDE3, as well as PDE10 and PDE11.

Previously named calmodulin-stimulated PDE (CaM-PDE), PDE1 is unique in that it is $Ca^{2+}$-dependently regulated via calmodulin (CaM, a 16 kDa $Ca^{2+}$-binding protein) complexed with four $Ca^{2+}$ (for review, Sharron H. Francis, Mitsi A. Blount, and Jackie D. Corbin. Physiol Rev 2011, 91: 651-690). Thus, PDE1 represents an interesting regulatory link between cyclic nucleotides and intracellular $Ca^{2+}$. The PDE1 family is encoded by three genes: PDE1A (mapped on human chromosome 2q32), PDE1B (human chromosome location, hcl: 12q13) and PDE1C (hcl: 7p14.3). They have alternative promoters and give rise to a multitude of proteins by alternative splicing which differ in their regulatory properties, substrate affinities, specific activities, activation constants for CaM, tissue distribution and molecular weights. More than 10 human isoforms are identified. Their molecular weights vary from 58 to 86 kDa per monomer. The N-terminal regulatory domain contains two $Ca^{2+}$/CaM binding domains and two phosphorylation sites and different splice variants have different variations of the N-terminal domain, which can give proteins with different amino acid sequence with different biochemical functions. PDE1 is a dual substrate PDE and the PDE1C-subtype has equal activity towards cAMP and cGMP (Km≈1-3 μM), whereas the subtypes PDE1A and PDE1B have a preference for cGMP (Km for cGMP≈1-3 μM and for cAMP≈10-30 μM).

The PDE1 subtypes are highly enriched in the brain and located especially in the striatum (PDE1B), hippocampus (PDE1A) and cortex (PDE1A) and this localization is conserved across species (Amy Bernard et al. Neuron 2012, 73, 1083-1099). In the cortex, PDE1A is present mainly in deep cortical layers 5 and 6 (output layers), and used as a specificity marker for the deep cortical layers. PDE1 inhibitors enhance the levels of the second messenger cNs leading to enhanced neuronal excitability.

Thus, PDE1 is a therapeutic target for regulation of intracellular signalling pathways, preferably in the nervous system and PDE1 inhibitors can enhance the levels of the second messenger's cAMP/cGMP leading to modulation of neuronal processes and to the expression of neuronal plasticity-related genes, neurotrophic factors, and neuroprotective molecules. These neuronal plasticity enhancement properties together with the modulation of synaptic transmission make PDE1 inhibitors good candidates as therapeutic agents in many neurological and psychiatric conditions. The evaluation of PDE1 inhibitors in animal models (for reviews see e.g. Blokland et al. Expert Opinion on Therapeutic Patents 2012, 22(4), 349-354; and Medina, A. E. Frontiers in Neuropharmacology 2011 5 (February), 21) has suggested the potential for the therapeutic use of PDE1 inhibitors in neurological disorders, like e.g. Alzheimer's, Parkinson's and Huntington's Diseases and in psychiatric disorders like e.g. Attention Deficit Hyperactivity Disorder (ADHD), depression, anxiety, narcolepsy, cognitive impairment and cognitive impairment associated with schizophrenia (CIAS) and in restless leg syndrome. There have also been patent applications claiming that PDE1 inhibitors are useful in diseases that may be alleviated by the enhancement of progesterone-signalling such as female sexual dysfunction (e.g. WO 2008/070095).

Various chemical structures with PDE1 inhibiting activity have been identified. WO 2016/055618 discloses triazolopyrazinones as PDE1 inhibitors; WO 2016/042775, US 2016/0083391 and US 2016/0083400 disclose tricyclic lactams as PDE1 inhibitors; and WO 2016/147659 discloses imidazopyrazinones as PDE1 inhibitors.

WO 2013/053690 and WO 2013/110768 disclose imidazopyrazinones and imidazotriazinones as PDE9 inhibitors.

Current treatments for neurodegenerative and/or psychiatric disorders are not efficacious in all patients. Hence, there remains a need for alternative methods of treatment of such diseases and for this purpose PDE1 inhibitors may be a good alternative. The present invention discloses new bicyclic lactams with PDE1 inhibitor activity and good physicochemical properties as alternatives to known PDE1 inhibitors.

SUMMARY OF THE INVENTION

PDE1 enzymes are expressed in the Central Nervous System (CNS), making this gene family an attractive source of new targets for the treatment of psychiatric and neurodegenerative disorders.

The objective of the present invention is to provide compounds that are PDE1 inhibitors, and as such are useful to treat neurodegenerative disorders and psychiatric disorders. Preferably, said compounds are at least a ten-fold stronger as PDE1 inhibitors than as PDE9 inhibitors in order to prevent potentially unwanted effects associated with PDE9 inhibition.

Accordingly, the present invention relates to compounds of formula (I)

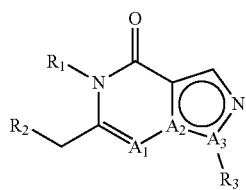

wherein
A1 is N, A2 is C and A3 is N; or
A1 is C, A2 is C and A3 is N; or
A1 is C, A2 is N and A3 is C;
R1 is hydrogen, or linear or branched $C_1$-$C_8$ alkyl; or
R1 is methyl substituted with phenyl, wherein said phenyl is optionally substituted one or more times with one or more substituents selected from the group consisting of halogen, $C_1$-$C_3$ alkyl, fluoromethyl, difluoromethyl, trifluoromethyl, methoxy, difluoromethoxy and trifluoromethoxy;
R2 is phenyl which is substituted in the 4-position with phenyl or with a heteroaromatic group; wherein said phenyl substituent or said heteroaromatic group can be substituted one or more times with one or more substituents selected from the group consisting of methyl, fluoromethyl, difluoromethyl, trifluoromethyl, halogen, hydroxy, cyano, methoxy, difluoromethoxy and trifluoromethoxy; or
R2 is piperazin-1-yl which is substituted in the 4-position with phenyl or with a heteroaromatic group; wherein said phenyl substituent or said heteroaromatic group can be substituted one or more times with one or more substituents selected from the group consisting of methyl, fluoromethyl, difluoromethyl, trifluoromethyl, halogen, hydroxy, cyano, methoxy, difluoromethoxy and trifluoromethoxy;
R3 is selected from the group consisting of linear or branched $C_2$-$C_8$ alkyl, saturated monocyclic $C_3$-$C_8$ cycloalkyl, oxetanyl, tetrahydrofuranyl, and tetrahydropyranyl; all of which can be substituted one or more times with one or more substituents selected from the group consisting of methyl, fluorine, hydroxy, cyano and methoxy;
or a pharmaceutically acceptable salt thereof.

Reference to compounds encompassed by the present invention includes the free base and pharmaceutically acceptable salts of the compounds, such as acid addition salts of the compounds, racemic mixtures of the compounds, or the corresponding enantiomer and/or optical isomer of the compounds, and polymorphic and amorphic forms as well as tautomeric forms of the compounds. Furthermore, the compounds of this invention may exist in unsolvated as well as in solvated forms with pharmaceutically acceptable solvents such as water, ethanol and the like. The present invention relates to both solvated and unsolvated forms of the compounds.

In one embodiment, the invention relates to a compound according to formula (I) for use in therapy.

In one embodiment, the invention relates to a compound according to formula (I), for use in the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

In one embodiment, the invention relates to a pharmaceutical composition comprising a compound according formula (I), and one or more pharmaceutically acceptable carrier or excipient.

In one embodiment, the invention relates to a method for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome, which method comprises the administration of a therapeutically effective amount of a compound according to formula (I) to a patient in need thereof.

Definitions

PDE1 Enzymes:

The PDE1 isozyme family includes numerous splice variant PDE1 isoforms. It has three subtypes, PDE1A, PDE1B and PDE1C which divide further into various isoforms. In the context of the present invention PDE1 and PDE1 enzymes are synonymous and refer to PDE1A, PDE1B and PDE1C enzymes as well as their isoforms unless otherwise specified.

PDE1 Inhibitors and PDE9 Inhibitors:

In the context of the present invention, a compound is considered to be a PDE1 inhibitor if the amount required to reach the $IC_{50}$ level of any of the three PDE1 isoforms is 10 micro molar or less, preferably less than 9 micro molar, such as 8 micro molar or less, such as 7 micro molar or less, such as 6 micro molar or less, such as 5 micro molar or less, such as 4 micro molar or less, such as 3 micro molar or less, more preferably 2 micro molar or less, such as 1 micro molar or less, in particular 500 nM or less. Some compounds of the invention exhibit selectivity towards the PDE1B isoform meaning that said compounds are stronger as PDE1B inhibitors than as PDE1A and/or PDE1C inhibitors. In preferred embodiments, said compounds are at least two-fold stronger, three-fold stronger, four-fold stronger or five-fold stronger as PDE1B inhibitors than as PDE1A and/or PDE1C inhibitors. In preferred embodiments, the required amount of PDE1 inhibitor required to reach the $IC_{50}$ level of PDE1B is 400 nM or less, such as 300 nM or less, 200 nM or less, 100 nM or less, or even 80 nM or less, such as 50 nM or less, for example 25 nM or less. Selectivity towards the PDE1B isoform may prevent potentially unwanted effects associated with PDE1A and/or PDE1C inhibition.

In a preferred embodiment, the compounds of the present invention are at least a ten-fold stronger as PDE1 inhibitors than as PDE9 inhibitors, i.e. the amount of the compound required to reach the $IC_{50}$ level of one or more of the three PDE1 isoforms is at least a ten-fold less than the amount of the same compound required to reach the $IC_{50}$ level of the PDE9 enzyme.

Substituents:

In the present context, "optionally substituted" means that the indicated moiety may or may not be substituted, and when substituted is mono-, di-, or tri-substituted. It is understood that where no substituents are indicated for an "optionally substituted" moiety, then the position is held by a hydrogen atom.

As used in the context of the present invention, the terms "halo" and "halogen" are used interchangeably and refer to fluorine, chlorine, bromine or iodine.

A given range may interchangeably be indicated with "-" (dash) or "to", e.g. the term "$C_1$-$C_3$ alkyl" is equivalent to "$C_1$ to $C_3$ alkyl".

The terms "$C_1$-$C_3$ alkyl", "$C_1$-$C_4$ alkyl", "$C_1$-$C_5$ alkyl", "$C_1$-$C_6$ alkyl", "$C_1$-$C_7$ alkyl" and "$C_1$-$C_8$ alkyl" refer to a linear (i.e. unbranched) or branched saturated hydrocarbon having from one up to eight carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, n-hexyl, n-heptyl and n-octyl.

The term saturated monocyclic $C_3$-$C_8$ cycloalkyl refers to cyclopropyl, cyclobutyl, cyclopentyl, cyclohexyl, cycloheptyl and cyclooctyl.

The term "heteroaromatic group" refers to a 5 or 6 membered aromatic monocyclic ring containing 1 to 5 carbon atoms and one or more heteroatoms selected from oxygen, nitrogen and sulfur. Examples include, 5 and 6 membered heteroaromatic groups such as, but not limited to pyridinyl, pyrimidinyl, pyrazinyl, imidazolyl and oxadiazolyl. Particular mention is made of pyridinyl.

The term "$C_1$-$C_3$ alkoxy" refers to a moiety of the formula —OR', wherein R' indicates $C_1$-$C_3$ alkyl as defined above.

Isomeric and Tautomeric Forms

Where compounds of the present invention contain one or more chiral centers reference to any of the compounds will, unless otherwise specified, cover the enantiomerically or diastereomerically pure compound as well as mixtures of the enantiomers or diastereomers in any ratio.

When a compound of the invention with one chiral center is denoted with the suffix "isomer 1" or "isomer 2" it is understood that said enantiomer could be either the S-enantiomer or the R-enantiomer. I.e. "isomer 1" could be either the S-enantiomer or the R-enantiomer and "isomer 2" could be either the S-enantiomer or the R-enantiomer. When both isomer 1 and isomer 2 have been exemplified for a compound it follows that one is the S-enantiomer and the other is the R-enantiomer. The absolute stereochemistry for a compound of the invention with one chiral center can be determined by X-ray crystallography or vibrational circular dichroism or other methods known to persons skilled in the art. Likewise, when a compound of the invention with two chiral centers is denoted with the suffix "isomer 1", "isomer 2", "isomer 3" or "isomer 4" it is understood that said diastereomer could be either the S,S-diastereomer, the R,S-diastereomer, the S,R-diastereomeror the R,R-diastereomer. I.e. "isomer 1" could be either the S,S-diastereomer, the R,S-diastereomer, the S,R-diastereomer or the R,R-diastereomer and "isomer 2" could be either the S,S-diastereomer, R,S-diastereomer, S,R-diastereomer or the R,R-diastereomer etc. When all four diastereomers (isomers 1-4) have been exemplified for a compound with two chiral centers it follows that one is the S,S-diastereomer, one is the R,S-diastereomer, one is the S,R-diastereomer and one is the R,R-diastereomer. The absolute stereochemistry for a compound of the invention with two chiral centers can be determined by X-ray crystallography or other methods known to persons skilled in the art.

Furthermore, some of the compounds of the present invention may exist in different tautomeric forms and it is intended that any tautomeric forms that the compounds are able to form are included within the scope of the present invention.

Pharmaceutically Acceptable Salts:

The compounds of this invention are generally utilized as the free substance or as a pharmaceutically acceptable salt thereof. When a compound of formula (I) contains a free base such salts are prepared in a conventional manner by treating a solution or suspension of a free base of formula (I) with a molar equivalent of a pharmaceutically acceptable acid. Representative examples of suitable organic and inorganic acids are described below.

Pharmaceutically acceptable salts in the present context is intended to indicate non-toxic, i.e. physiologically acceptable salts. The term pharmaceutically acceptable salts includes salts formed with inorganic and/or organic acids such as hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, salicylic acid and sulfonic acids, such as methanesulfonic acid, ethanesulfonic acid, toluenesulfonic acid and benzenesulfonic acid. Some of the acids listed above are di- or tri-acids, i.e. acids containing two or three acidic hydrogens, such as phosphoric acid, sulphuric acid, fumaric acid and maleic acid.

Additional examples of useful acids to form pharmaceutically acceptable salts can be found e.g. in Stahl and Wermuth (Eds) "Handbook of Pharmaceutical salts. Properties, selection, and use", Wiley-VCH, 2008.

Therapeutically Effective Amount:

In the present context, the term "therapeutically effective amount" of a compound means an amount sufficient to alleviate, arrest or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

Treatment and Treating:

In the present context, "treatment" or "treating" is intended to indicate the management and care of a patient for the purpose of alleviating, arresting, partly arresting or delaying progress of the clinical manifestation of the disease. The patient to be treated is preferably a mammal, in particular a human being.

Administration Routes:

The pharmaceutical compositions may be specifically formulated for administration by any suitable route such as the oral, rectal, nasal, buccal, sublingual, transdermal and parenteral (e.g. subcutaneous, intramuscular, and intravenous) route; the oral route being preferred.

It will be appreciated that the route will depend on the general condition and age of the subject to be treated, the nature of the condition to be treated and the active ingredient.

Pharmaceutical Formulations and Excipients:

In the following, the term, "excipient" or "pharmaceutically acceptable excipient" refers to pharmaceutical excipients including, but not limited to, fillers, antiadherents, binders, coatings, colours, disintegrants, flavours, glidants, lubricants, preservatives, sorbents, sweeteners, solvents, vehicles and adjuvants.

The present invention also provides a pharmaceutical composition comprising a compound of formula (I), such as one of the compounds disclosed in the Experimental Section herein. The present invention also provides a process for making a pharmaceutical composition comprising a compound of formula (I). The pharmaceutical compositions according to the invention may be formulated with pharmaceutically acceptable excipients in accordance with conventional techniques such as those disclosed in Remington, "The Science and Practice of Pharmacy", 22$^{th}$ edition (2012), Edited by Allen, Loyd V., Jr.

Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Doses:

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.1-1000 mg/day of a compound of the present invention, such as 1-500 mg/day, such as 1-100 mg/day or 1-50 mg/day. Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

DETAILED DESCRIPTION OF THE INVENTION

The present inventors have identified compounds that are PDE1 inhibitors, and as such are useful to treat neurodegenerative and psychiatric disorders. The present invention thus provides compounds of formula (I) that are effective in inhibiting PDE1 for use as a medicament in the treatment of a mammal, preferably a human.

The invention provides a compound of formula (I) or a pharmaceutically acceptable salt thereof, as well as a pharmaceutical composition containing such compound, for use in the treatment of a brain disease which could be a neurodegenerative disorder or a psychiatric disorder. In a preferred embodiment, the neurodegenerative disorder is selected from the group consisting of Alzheimer's Disease, Parkinson's Disease and Huntington's Disease. In another preferred embodiment, the psychiatric disorder is selected from the group consisting of Attention Deficit Hyperactivity Disorder (ADHD), depression, anxiety, narcolepsy, cognitive impairment and cognitive impairment associated with schizophrenia (CIAS). Other brain disorders could be e.g. restless leg syndrome.

This invention further provides a method of treating a brain disease which could be a neurodegenerative or a psychiatric disorder, which method comprises administering to said mammal a pharmaceutically effective amount of a compound of formula (I) or a pharmaceutically acceptable salt thereof. Examples of neurodegenerative disorders that can be treated according to the present invention include Alzheimer's Disease, Parkinson's Disease and Huntington's Disease, which method comprises administering to the subject a therapeutically effective amount of a compound of formula (I). Examples of psychiatric disorders that can be treated according to the present invention include Attention Deficit Hyperactivity Disorder (ADHD), depression, narcolepsy, cognitive impairment and cognitive impairment associated with schizophrenia (CIAS). Other brain disorders to be treated could be e.g. restless leg syndrome.

EMBODIMENTS OF THE INVENTION

In the following, embodiments of the invention are disclosed. The first embodiment is denoted E1, the second embodiment is denoted E2 and so forth E1. A compound according to formula (I)

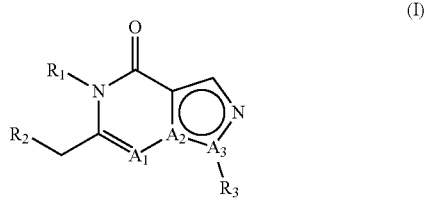

wherein
A1 is N, A2 is C and A3 is N; or
A1 is C, A2 is C and A3 is N; or
A1 is C, A2 is N and A3 is C;
R1 is hydrogen, or linear or branched $C_1$-$C_8$ alkyl; or
R1 is methyl substituted with phenyl, wherein said phenyl is optionally substituted one or more times with one or more substituents selected from the group consisting of halogen, $C_1$-$C_3$ alkyl, fluoromethyl, difluoromethyl, trifluoromethyl, methoxy, difluoromethoxy and trifluoromethoxy;
R2 is phenyl which is substituted in the 4-position with phenyl or with a heteroaromatic group; wherein said phenyl substituent or said heteroaromatic group can be substituted one or more times with one or more substituents selected from the group consisting of methyl, fluoromethyl, difluoromethyl, trifluoromethyl, halogen, hydroxy, cyano, methoxy, difluoromethoxy and trifluoromethoxy; or
R2 is piperazin-1-yl which is substituted in the 4-position with phenyl or with a heteroaromatic group; wherein said phenyl substituent or said heteroaromatic group can be substituted one or more times with one or more substituents selected from the group consisting of methyl, fluoromethyl, difluoromethyl, trifluoromethyl, halogen, hydroxy, cyano, methoxy, difluoromethoxy and trifluoromethoxy;
R3 is selected from the group consisting of linear or branched $C_2$-$C_8$ alkyl, saturated monocyclic $C_3$-$C_8$ cycloalkyl, oxetanyl, tetrahydrofuranyl, and tetrahydropyranyl; all of which can be substituted one or more times with one or more substituents selected from the group consisting of methyl, fluorine, hydroxy, cyano and methoxy;
or a pharmaceutically acceptable salt thereof.

E2. The compound according to embodiment 1, wherein A1 is N, A2 is C and A3 is N.
E3. The compound according to embodiment 1, wherein A1 is C, A2 is C and A3 is N.
E4. The compound according to embodiment 1, wherein A1 is C, A2 is N and A3 is C.
E5. The compound according to embodiment 1, wherein A1 is N, A2 is C and A3 is N; or A1 is C, A2 is C and A3 is N.
E6. The compound according to embodiment 1, wherein A1 is C, A2 is C and A3 is N; or A1 is C, A2 is N and A3 is C.
E7. The compound according to embodiment 1, wherein A1 is N, A2 is C and A3 is N; or A1 is C, A2 is N and A3 is C.
E8. The compound according to any of embodiments 1-7, wherein R1 is hydrogen.
E9. The compound according to any of embodiments 1-7, wherein R1 is other than hydrogen.
E10. The compound according to any of embodiments 1-7, wherein R1 is linear or branched $C_1$-$C_8$ alkyl.
E11. The compound according to embodiment 10, wherein R1 is methyl or ethyl.
E12. The compound according to any of embodiments 1-7, wherein R1 is methyl substituted with phenyl, wherein said phenyl is optionally substituted one or more times with one or more substituents selected from the group consisting of halogen, $C_1$-$C_3$ alkyl and methoxy.
E13. The compound according to embodiment 12, wherein R1 is methyl substituted with phenyl, wherein said phenyl is substituted one time with methoxy.
E14. The compound according to any of embodiments 1-13, wherein R2 is phenyl which is substituted in the 4-position with phenyl or with a heteroaromatic group; wherein said phenyl substituent or said heteroaromatic group can be substituted one or more times with one or more substituents selected from the group consisting of methyl, fluoromethyl, difluoromethyl, trifluoromethyl, halogen, hydroxy, cyano, methoxy, difluoromethoxy and trifluoromethoxy.
E15. The compound according to embodiment 14, wherein R2 is phenyl which is substituted in the 4-position with a heteroaromatic group which can be substituted one or more times with one or more substituents selected from the group consisting of methyl, fluoromethyl, difluoromethyl, trifluoromethyl, halogen, hydroxy, cyano, methoxy, difluoromethoxy and trifluoromethoxy.
E16. The compound according to any of embodiments 14-15, wherein said heteroaromatic group is selected from pyridinyl, pyrimidinyl, pyrazinyl and imidazolyl.
E17. The compound according to embodiment 16, wherein said heteroaromatic group is 2-pyridinyl.
E18. The compound according to embodiment 14, wherein R2 is phenyl which is substituted in the 4-position with phenyl wherein said phenyl substituent can be substituted one or more times with one or more substituents selected from the group consisting of methyl, fluoromethyl, difluoromethyl, trifluoromethyl, halogen, hydroxy, cyano, methoxy, difluoromethoxy and trifluoromethoxy.
E19. The compound according to any of embodiments 1-13, wherein R2 is piperazin-1-yl which is substituted in the 4-position with phenyl or with a heteroaromatic group; wherein said phenyl substituent or said heteroaromatic group can be substituted one or more times with one or more substituents selected from the group consisting of methyl, fluoromethyl, difluoromethyl, trifluoromethyl, halogen, hydroxy, cyano, methoxy, difluoromethoxy and trifluoromethoxy.

E20. The compound according to embodiment 19, wherein R2 is piperazin-1-yl which is substituted in the 4-position with a heteroaromatic group which can be substituted one or more times with one or more substituents selected from the group consisting of methyl, fluoromethyl, difluoromethyl, trifluoromethyl, halogen, hydroxy, cyano, methoxy, difluoromethoxy and trifluoromethoxy.

E21. The compound according to any of embodiments 19-20, wherein said heteroaromatic group is selected from pyridinyl, pyrimidinyl, pyrazinyl and imidazolyl.

E22. The compound according to embodiment 21, wherein said heteroaromatic group is 2-pyridinyl.

E23. The compound according to embodiment 19, wherein R2 is piperazin-1-yl which is substituted in the 4-position with phenyl wherein said phenyl substituent can be substituted one or more times with one or more substituents selected from the group consisting of methyl, fluoromethyl, difluoromethyl, trifluoromethyl, halogen, hydroxy, cyano, methoxy, difluoromethoxy and trifluoromethoxy.

E24. The compound according to any of embodiments 14-23, wherein said phenyl substituent or said heteroaromatic group is substituted once with a substituent selected from the group consisting of methyl, fluoromethyl, difluoromethyl, trifluoromethyl, halogen, hydroxy, cyano, methoxy, difluoromethoxy and trifluoromethoxy.

E25. The compound according to any of embodiments 14-24, wherein said halogen is fluorine.

E26. The compound according to any of embodiments 14-23, wherein said one or more substituents are selected from methyl, difluoromethyl, fluorine and methoxy.

E27. The compound according to embodiment 24, wherein said substituent is selected from methyl, difluoromethyl, fluorine and methoxy.

E28. The compound according to any of embodiments 14-23, wherein said phenyl substituent or said heteroaromatic group is unsubstituted.

E29. The compound according to any of embodiments 1-28, wherein R3 is selected from $C_2$-$C_3$ alkyl, oxetanyl, tetrahydrofuranyl, and tetrahydropyranyl; all of which can be substituted one or more times with one or more substituents selected from the group consisting of methyl, fluorine, hydroxy, cyano and methoxy.

E30. The compound according to any of embodiments 1-28, wherein R3 is selected from the group consisting of linear or branched $C_2$-$C_8$ alkyl, saturated monocyclic $C_3$-$C_8$ cycloalkyl, oxetanyl, tetrahydrofuranyl and tetrahydropyranyl; all of which are unsubstituted.

E31. The compound according to any of embodiments 1-28, wherein R3 is selected from unsubstituted $C_2$-$C_3$ alkyl, oxetanyl, tetrahydrofuranyl, and tetrahydropyranyl.

E32. The compound according to any of embodiments 1-28, wherein R3 is $C_2$-$C_3$ alkyl which is optionally substituted with one or more fluorine.

E33. The compound according to any of embodiments 1-28, wherein R3 is unsubstituted tetrahydropyranyl.

E34. The compound according to any of embodiments 1-28, wherein R3 is tetrahydrofuranyl which is optionally substituted with a methyl.

E35. The compound according to any of embodiments 1-13, wherein R2 is phenyl which is substituted in the 4-position with phenyl or with pyridinyl; wherein said phenyl substituent or said pyridinyl can be substituted one or more times with one or more substituents selected from the group consisting of methyl, fluoromethyl, halogen, hydroxy, cyano and methoxy.

E36. The compound according to any of embodiments 1-13, wherein R2 is piperazin-1-yl which is substituted in the 4-position with phenyl or with pyridinyl; wherein said phenyl substituent or said pyridinyl can be substituted one or more times with one or more substituents selected from the group consisting of methyl, fluoromethyl, halogen, hydroxy, cyano and methoxy.

E37. The compound according to embodiment 36, wherein said heteroaromatic group is 2-pyridinyl.

E38. The compound according to any of embodiments 35-37, wherein said one or more substituents are selected from methyl, fluoromethyl, difluoromethyl, trifluoromethyl, fluorine, methoxy, difluoromethoxy and trifluoromethoxy.

E39. The compound according to embodiment 1, wherein the compound is selected from the group consisting of:
1. 5-methyl-6-[[4-(6-methyl-2-pyridyl)phenyl]methyl]-1-tetrahydropyran-4-yl-pyrazolo[4,3-c]pyridin-4-one;
2. 5-methyl-6-[[4-(2-pyridyl)phenyl]methyl]-1-tetrahydropyran-4-yl-pyrazolo[3,4-d]pyrimidin-4-one;
3. 5-methyl-6-[[4-(6-methyl-2-pyridyl)phenyl]methyl]-1-tetrahydropyran-4-yl-pyrazolo[3,4-d]pyrimidin-4-one;
4. 6-[[4-(6-fluoro-2-pyridyl)phenyl]methyl]-5-methyl-1-tetrahydropyran-4-yl-pyrazolo[3,4-d]pyrimidin-4-one;
5. 6-[[4-(6-fluoro-2-pyridyl)phenyl]methyl]-5-methyl-1-tetrahydropyran-4-yl-pyrazolo[4,3-c]pyridin-4-one;
6. 5-methyl-6-[[4-(2-pyridyl)phenyl]methyl]-1-tetrahydropyran-4-yl-pyrazolo[4,3-c]pyridin-4-one;
7. 7-[(4-methoxyphenyl)methyl]-6-[[4-(2-pyridyl)piperazin-1-yl]methyl]-3-tetrahydropyran-4-yl-imidazo[1,5-a]pyrazin-8-one;
8. 7-[(4-methoxyphenyl)methyl]-6-[(4-phenylpiperazin-1-yl)methyl]-3-tetrahydropyran-4-yl-imidazo[1,5-a]pyrazin-8-one;
9. 7-[(4-methoxyphenyl)methyl]-6-[[4-(2-pyridyl)phenyl]methyl]-3-tetrahydropyran-4-yl-imidazo[1,5-a]pyrazin-8-one;
10. 6-[[4-(2-pyridyl)phenyl]methyl]-3-tetrahydropyran-4-yl-7H-imidazo[1,5-a]pyrazin-8-one;
11. 7-methyl-6-[[4-(2-pyridyl)phenyl]methyl]-3-tetrahydropyran-4-yl-imidazo[1,5-a]pyrazin-8-one;
12. 7-ethyl-6-[[4-(2-pyridyl)phenyl]methyl]-3-tetrahydropyran-4-yl-imidazo[1,5-a]pyrazin-8-one;
13. 7-methyl-6-[[4-(6-methyl-2-pyridyl)phenyl]methyl]-3-tetrahydropyran-4-yl-imidazo[1,5-a]pyrazin-8-one;
14. 6-[[4-(6-fluoro-2-pyridyl)phenyl]methyl]-7-methyl-3-tetrahydropyran-4-yl-imidazo[1,5-a]pyrazin-8-one;
15. 6-[[4-(6-(difluoromethyl)-2-pyridyl)phenyl]methyl]-7-methyl-3-tetrahydropyran-4-yl-imidazo[1,5-a]pyrazin-8-one;
16. 6-[[4-(6-methoxy-2-pyridyl)phenyl]methyl]-7-methyl-3-tetrahydropyran-4-yl-imidazo[1,5-a]pyrazin-8-one;
17. 6-[[4-(3-methoxy-2-pyridyl)phenyl]methyl]-7-methyl-3-tetrahydropyran-4-yl-imidazo[1,5-a]pyrazin-8-one;
18. 7-methyl-6-[[4-(o-tolyl)phenyl]methyl]-3-tetrahydropyran-4-yl-imidazo[1,5-a]pyrazin-8-one;
19. 7-methyl-6-[(4-phenylphenyl)methyl]-3-tetrahydropyran-4-yl-imidazo[1,5-a]pyrazin-8-one;
20. 7-methyl-6-(4-(1-methyl-1H-imidazol-4-yl)benzyl)-3-(tetrahydro-2H-pyran-4-yl)imidazo[1,5-a]pyrazin-8(7H)-one;
21. 6-[[4-(6-fluoro-2-pyridyl)phenyl]methyl]-3-isopropyl-7-methyl-imidazo[1,5-a]pyrazin-8-one;
22. 6-(4-(6-fluoropyridin-2-yl)benzyl)-7-methyl-3-propylimidazo[1,5-a]pyrazin-8(7H)-one;

23. 3-ethyl-6-(4-(6-fluoropyridin-2-yl)benzyl)-7-methylimidazo[1,5-a]pyrazin-8(7H)-one;
24. 7-methyl-6-(4-(pyrazin-2-yl)benzyl)-3-(tetrahydro-2H-pyran-4-yl)imidazo[1,5-a]pyrazin-8(7H)-one;
25. 6-(4-(6-fluoropyridin-2-yl)benzyl)-7-methyl-3-(2,2,2-trifluoroethyl)imidazo[1,5-a]pyrazin-8(7H)-one;
26. 7-methyl-6-(4-(pyrimidin-4-yl)benzyl)-3-(tetrahydro-2H-pyran-4-yl)imidazo[1,5-a]pyrazin-8(7H)-one;
27. 6-(4-(6-fluoropyridin-2-yl)benzyl)-7-methyl-3-(tetrahydrofuran-3-yl)imidazo[1,5-a]pyrazin-8(7H)-one, isomer 1;
28. 6-(4-(6-fluoropyridin-2-yl)benzyl)-7-methyl-3-(tetrahydrofuran-3-yl)imidazo[1,5-a]pyrazin-8(7H)-one, isomer 2;
29. 6-(4-(6-fluoropyridin-2-yl)benzyl)-7-methyl-3-(2-methyltetrahydrofuran-3-yl)imidazo[1,5-a]pyrazin-8(7H)-one, isomer 1;
30. 6-(4-(6-fluoropyridin-2-yl)benzyl)-7-methyl-3-(2-methyltetrahydrofuran-3-yl)imidazo[1,5-a]pyrazin-8(7H)-one, isomer 2;
31. 6-(4-(6-fluoropyridin-2-yl)benzyl)-7-methyl-3-(2-methyltetrahydrofuran-3-yl)imidazo[1,5-a]pyrazin-8(7H)-one, isomer 3;
32. 6-(4-(6-fluoropyridin-2-yl)benzyl)-7-methyl-3-(2-methyltetrahydrofuran-3-yl)imidazo[1,5-a]pyrazin-8(7H)-one, isomer 4;
or a pharmaceutically acceptable salt of any of these compounds.

E40. The compound according to embodiment 1, wherein the compound is:
10. 6-[[4-(2-pyridyl)phenyl]methyl]-3-tetrahydropyran-4-yl-7H-imidazo[1,5-a]pyrazin-8-one;
or a pharmaceutically acceptable salt thereof.

E41. A compound of any one of embodiments 1-40, wherein said compound has a PDE1A, PDE1B or PDE1C $IC_{50}$ value, determined as described in the section "PDE1 inhibition assay", of 10 micro molar or less, such as 5 micro molar or less, such as 4 micro molar or less, such as 3 micro molar or less, such as 2 micro molar or less, such as 1 micro molar or less, such as 500 nM or less, such as 400 nM or less, such as 300 nM or less, such as 200 nM or less, such as 100 nM or less.

E42. A compound of any one of embodiments 1-40 for use in therapy.

E43. A compound according to any of embodiments 1-40, for use as a medicament.

E44. A pharmaceutical composition comprising a therapeutically effective amount of a compound of any one of embodiments 1-40 and one or more pharmaceutically acceptable carriers, diluents or excipients.

E45. A compound according to any of embodiments 1-40 for use in the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

E46. A method for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome, which method comprises the administration of a therapeutically effective amount of a compound according to any of embodiments 1-40 to a patient in need thereof.

E47. Use of a compound according to any of embodiments 1-40, for the manufacture of a medicament for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "such as") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

COMPOUNDS OF THE INVENTION

TABLE 1

Compounds of the invention

| Example | Compound | PDE1A, $IC_{50}$ (nM) | PDE1B, $IC_{50}$ (nM) | PDE1C, $IC_{50}$ (nM) | PDE9 Inhibition at 10 μM (%) |
| --- | --- | --- | --- | --- | --- |
| 1 | 5-methyl-6-[[4-(6-methyl-2-pyridyl)phenyl]methyl]-1-tetrahydropyran-4-yl-pyrazolo[4,3-c]pyridin-4-one | 150 | 32 | 220 | 10 |
| 2 | 5-methyl-6-[[4-(2-pyridyl)phenyl]methyl]-1- | 390 | 92 | 530 | 5 |

TABLE 1-continued

Compounds of the invention

| Example | Compound | PDE1A, IC$_{50}$ (nM) | PDE1B, IC$_{50}$ (nM) | PDE1C, IC$_{50}$ (nM) | PDE9 Inhibition at 10 μM (%) |
|---|---|---|---|---|---|
|  | tetrahydropyran-4-yl-pyrazolo[3,4-d]pyrimidin-4-one |  |  |  |  |
| 3 | 5-methyl-6-[[4-(6-methyl-2-pyridyl)phenyl]methyl]-1-tetrahydropyran-4-yl-pyrazolo[3,4-d]pyrimidin-4-one | 350 | 93 | 660 | 25 |
| 4 | 6-[[4-(6-fluoro-2-pyridyl)phenyl]methyl]-5-methyl-1-tetrahydropyran-4-yl-pyrazolo[3,4-d]pyrimidin-4-one | 180 | 57 | 2100 | 17 |
| 5 | 6-[[4-(6-fluoro-2-pyridyl)phenyl]methyl]-5-methyl-1-tetrahydropyran-4-yl-pyrazolo[4,3-c]pyridin-4-one | 120 | 20 | 190 | 3 |
| 6 | 5-methyl-6-[[4-(2-pyridyl)phenyl]methyl]-1-tetrahydropyran-4-yl-pyrazolo[4,3-c]pyridin-4-one | 160 | 25 | 240 | 4 |
| 7 | 7-[(4-methoxyphenyl)methyl]-6-[[4-(2-pyridyl)piperazin-1-yl]methyl]-3-tetrahydropyran-4-yl-imidazo[1,5-a]pyrazin-8-one | 88 | 13 | 190 | 19 |
| 8 | 7-[(4-methoxyphenyl)methyl]-6-[(4-phenylpiperazin-1-yl)methyl]-3-tetrahydropyran-4-yl-imidazo[1,5-a]pyrazin-8-one | 59 | 9.8 | 140 | 11 |
| 9 | 7-[(4-methoxyphenyl)methyl]-6-[[4-(2-pyridyl)phenyl]methyl]-3-tetrahydropyran-4-yl-imidazo[1,5-a]pyrazin-8-one | 0.29 | 0.19 | 0.38 | 39 |
| 10 | 6-[[4-(2-pyridyl)phenyl]methyl]-3-tetrahydropyran-4-yl-7H-imidazo[1,5-a]pyrazin-8-one | 17 | 6 | 22 | IC50 = 180 nM |
| 11 | 7-methyl-6-[[4-(2-pyridyl)phenyl]methyl]-3-tetrahydropyran-4-yl-imidazo[1,5-a]pyrazin-8-one | 30 | 3.5 | 120 | −10 |
| 12 | 7-ethyl-6-[[4-(2-pyridyl)phenyl]methyl]-3-tetrahydropyran-4-yl-imidazo[1,5-a]pyrazin-8-one | 12 | 3.1 | 26 | 4 |
| 13 | 7-methyl-6-[[4-(6-methyl-2-pyridyl)phenyl]methyl]-3-tetrahydropyran-4-yl-imidazo[1,5-a]pyrazin-8-one | 81 | 14 | 80 | 18 |
| 14 | 6-[[4-(6-fluoro-2-pyridyl)phenyl]methyl]-7-methyl-3-tetrahydropyran-4-yl-imidazo[1,5-a]pyrazin-8-one | 62 | 5.2 | 67 | 14 |
| 15 | 6-[[4-[6-(difluoromethyl)-2-pyridyl]phenyl]methyl]-7-methyl-3-tetrahydropyran-4-yl-imidazo[1,5-a]pyrazin-8-one | 58 | 14 | 87 | 6 |
| 16 | 6-[[4-(6-methoxy-2-pyridyl)phenyl]methyl]-7-methyl-3-tetrahydropyran-4-yl-imidazo[1,5-a]pyrazin-8-one | 24 | 4.7 | 42 | 7 |
| 17 | 6-[[4-(3-methoxy-2-pyridyl)phenyl]methyl]-7-methyl-3-tetrahydropyran-4-yl-imidazo[1,5-α]pyrazin-8-one | 87 | 21 | 161 | 2 |
| 18 | 7-methyl-6-[[4-(o-tolyl)phenyl]methyl]-3-tetrahydropyran-4-yl-imidazo[1,5-a]pyrazin-8-one | 117 | 23 | 238 | 9 |
| 19 | 7-methyl-6-[(4-phenylphenyl)methyl]-3-tetrahydropyran-4-yl-imidazo[1,5-a]pyrazin-8-one | 28 | 7.3 | 61 | 7 |
| 20 | 7-methyl-6-(4-(1-methyl-1H-imidazol-4-yl)benzyl)-3-(tetrahydro-2H-pyran-4-yl)imidazo[1,5-a]pyrazin-8(7H)-one | 75 | 17 | 157 | −6 |
| 21 | 6-[[4-(6-fluoro-2-pyridyl)phenyl]methyl]-3-isopropyl-7-methyl-imidazo[1,5-a]pyrazin-8-one | 36 | 13 | 93 | 13 |

TABLE 1-continued

Compounds of the invention

| Example | Compound | PDE1A, IC$_{50}$ (nM) | PDE1B, IC$_{50}$ (nM) | PDE1C, IC$_{50}$ (nM) | PDE9 Inhibition at 10 μM (%) |
|---|---|---|---|---|---|
| 22 | 6-(4-(6-fluoropyridin-2-yl)benzyl)-7-methyl-3-propylimidazo[1,5-α]pyrazin-8(7H)-one | 168 | 40 | 310 | 2 |
| 23 | 3-ethyl-6-(4-(6-fluoropyridin-2-yl)benzyl)-7-methylimidazo[1,5-a]pyrazin-8(7H)-one | 176 | 56 | 578 | 17 |
| 24 | 7-methyl-6-(4-(pyrazin-2-yl)benzyl)-3-(tetrahydro-2H-pyran-4-yl)imidazo[1,5-a]pyrazin-8(7H)-one | 91 | 30 | 198 | −2 |
| 25 | 6-(4-(6-fluoropyridin-2-yl)benzyl)-7-methyl-3-(2,2,2-trifluoroethyl)imidazo[1,5-a]pyrazin-8(7H)-one | 218 | 90 | 400 | 9 |
| 26 | 7-methyl-6-(4-(pyrimidin-4-yl)benzyl)-3-(tetrahydro-2H-pyran-4-yl)imidazo[1,5-a]pyrazin-8(7H)-one | 68 | 16 | 149 | 14 |
| 27 | 6-(4-(6-fluoropyridin-2-yl)benzyl)-7-methyl-3-(tetrahydrofuran-3-yl)imidazo[1,5-a]pyrazin-8(7H)-one, isomer 1 | 57 | 16 | 96 | 4 |
| 28 | 6-(4-(6-fluoropyridin-2-yl)benzyl)-7-methyl-3-(tetrahydrofuran-3-yl)imidazo[1,5-a]pyrazin-8(7H)-one, isomer 2 | 71 | 26 | 111 | 6 |
| 29 | 6-(4-(6-fluoropyridin-2-yl)benzyl)-7-methyl-3-(2-methyltetrahydrofuran-3-yl)imidazo[1,5-a]pyrazin-8(7H)-one, isomer 1 | 61 | 24 | 104 | 4 |
| 30 | 6-(4-(6-fluoropyridin-2-yl)benzyl)-7-methyl-3-(2-methyltetrahydrofuran-3-yl)imidazo[1,5-a]pyrazin-8(7H)-one, isomer 2 | 70 | 71 | 148 | −2 |
| 31 | 6-(4-(6-fluoropyridin-2-yl)benzyl)-7-methyl-3-(2-methyltetrahydrofuran-3-yl)imidazo[1,5-a]pyrazin-8(7H)-one, isomer 3 | 18 | 4 | 45 | 10 |
| 32 | 6-(4-(6-fluoropyridin-2-yl)benzyl)-7-methyl-3-(2-methyltetrahydrofuran-3-yl)imidazo[1,5-a]pyrazin-8(7H)-one, isomer 4 | 5.8 | 1.3 | 9.2 | 5 |

Table 1 lists the IC$_{50}$ value for inhibition of PDE1 by the compounds of the invention. The IC$_{50}$ value refers to the concentration (nM) of the compound required to reach 50% inhibition of the PDE1 enzyme at the specified substrate concentration. Table 1 also lists values for inhibition of the PDE9 receptor at 10 μM.

The PDE1 and PDE9 assays are described in the Experimental Section.

EXPERIMENTAL SECTION

Preparation of the Compounds of the Invention—General Methods

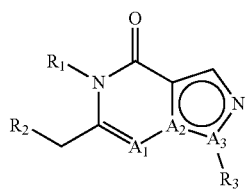
(I)

The compounds of formula (I) may be prepared by methods described below, together with synthetic methods known in the art of organic chemistry, or modifications that are familiar to those of ordinary skill in the art. The starting materials used herein are available commercially or may be prepared by routine methods known in the art, such as those methods described in standard reference books such as "Compendium of Organic Synthetic Methods, Vol. I-XIII" (published with Wiley-Interscience, ISSN: 1934-4783). Preferred methods include, but are not limited to, those described below.

The schemes are representative of methods useful in synthesizing the compounds of the present invention. They are not to constrain the scope of the invention in any way.

Method 1:

Scheme 1 where $R_1$, and $R_3$ are as described for formula I; R is an alkyl group such as methyl or ethyl; R4 is phenyl or a heteroaromatic group; all of which can be substituted one or more times with one or more substituents selected from the group consisting of methyl, halogen, hydroxy, cyano or methoxy; and R5 is hydrogen or the two R5 are connected to form a cyclic boronic acid ester such as 4,4,5,5-tetramethyl-1,3,2-dioxaborolane; and X is a halogen such as chlorine, bromine or iodine Compounds of general formula II (Scheme 1) can be prepared as described in the literature (J. Med. Chem. 2009, 52, 7949). Compounds of general formula IV can be prepared by reaction of compounds of general formula II and compounds of general formula III in the presence of a base such as potassium tert-butoxide. Compounds of general formula VI can be prepared by treatment of compounds of general formula IV with compounds of general formula V in the presence of a base such as but not limited to potassium carbonate or cesium carbonate. Compounds of general formula VII can be prepared by reaction of compounds of general formula VI with a reagent such as 4,4,4',4',5,5,5',5'-octamethyl-2,2'-bi(1,3,2-dioxaborolane) in the presence of a palladium catalyst such as $PdCl_2(dppf)$ ([1,1'-bis(diphenylphosphino)ferrocene]dichloropalladium(II)) and a base such as potassium acetate. Reaction of compounds of general formula VII with compounds of general formula VIII in the presence of a palladium catalyst such as $PdCl_2(dppf)$ and a base such as cesium carbonate gives compounds of general formula Ia. Alternatively, compounds of general formula VI can react with compounds of general formula VIIIa in the presence of a palladium catalyst such as $PdCl_2(dppf)$ ([1,1'-bis(diphenylphosphino)ferrocene]dichloropalladium(II)) and a base such as cesium carbonate to give compounds of general formula Ia.

Method 2:

Scheme 2 where $R_1$, $R_2$, and $R_3$ are as described for formula I

Compounds of general formula Ia where $R_1$ is hydrogen (Scheme 2) can be prepared by reaction of compounds of general formula II and compounds of general formula III (scheme 2) in the presence of a base such as potassium tert-butoxide. Compounds of general formula Ia where $R_1$ is not hydrogen can be prepared by treatment of compounds of general formula Ia where $R_1$ is hydrogen with compounds of general formula V in the presence of a base such as but not limited to potassium carbonate or cesium carbonate.

Method 3:

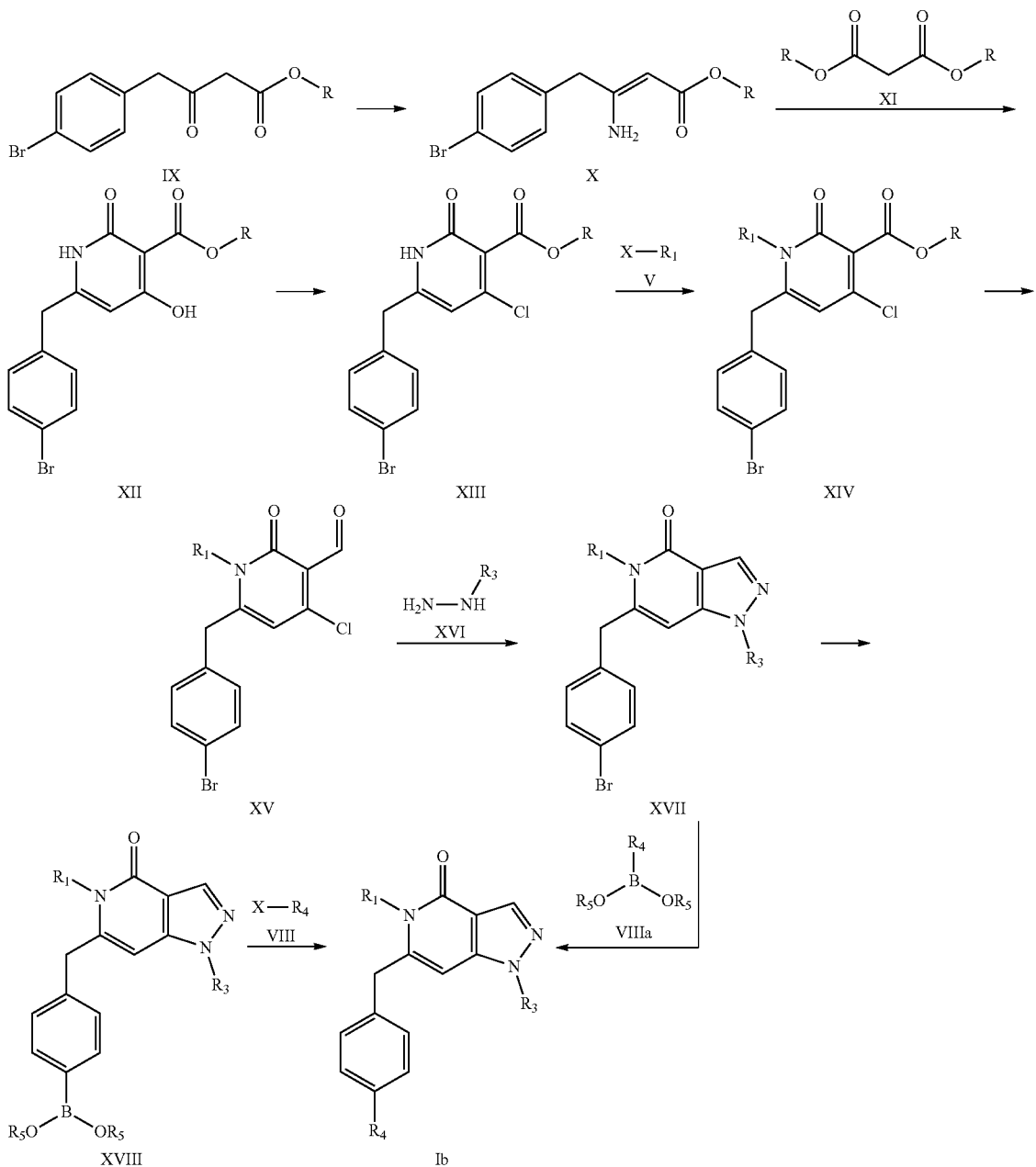

Scheme 3 where $R_1$ and $R_3$ are as described for formula I; R is an alkyl group such as methyl or ethyl; $R_4$ is phenyl or a heteroaromatic group; all of which can be substituted one or more times with one or more substituents selected from the group consisting of methyl, halogen, hydroxy, cyano or methoxy; and $R_5$ is hydrogen or the two $R_5$ are connected to form a cyclic boronic acid ester such as 4,4,5,5-tetramethyl-1,3,2-dioxaborolane; and X is a halogen such as chlorine, bromine or iodine Compounds of general formula X (Scheme 3) can be prepared by treatment of compounds of general formula IX with ammonium acetate. Treatment of compounds of general formulae X and XI with a base such as sodium ethoxide gives compounds of general formula XII. Treatment of compounds of general formula XII with a reagent such as dichlorophosphorylbenzene gives compounds of general formula XIII, which can be alkylated with compounds of general formula V in the presence of a base such as but not limited to potassium carbonate or cesium carbonate to give compounds of general formula XIV. Reduction of the ester moiety of compounds of general formula XIV gives compounds of general formula XV. Reaction of compounds of general formula XV with hydrazines of general formula XVI gives compounds of general formula XVII, which after reaction with a reagent such as 4,4,4',4',5,5,5',5'-octamethyl-2,2'-bi(1,3,2-dioxaborolane) in the presence of a palladium catalyst such as $PdCl_2(dppf)$ and a base such as potassium acetate gives compounds of general formula XVIII. Reaction of compounds of general formula XVIII with compounds of general formula VIII in the presence of a palladium catalyst such as PdCl$_2$(dppf) and a base such as cesium carbonate gives compounds of general formula Ib (scheme 3). Alternatively, compounds of general formula XVII can react with compounds of general formula VIIIa in the presence of a palladium catalyst such as PdCl$_2$(dppf) ([1,1'-bis(diphenylphosphino)ferrocene]dichloropalladium(II)) and a base such as cesium carbonate to give compounds of general formula Ib (scheme 3).

Method 4:

Compounds of general formula XX (Scheme 4) can be prepared by treatment of compounds of general formula XIX with ammonium acetate. Treatment of compounds of general formulae XX and XI with a base such as sodium ethoxide gives compounds of general formula XXI. Treatment of compounds of general formula XXI with a reagent such as dichlorophosphorylbenzene gives compounds of general formula XXII, which can be alkylated with compounds of general formula V in the presence of a base such as but not limited to potassium carbonate or cesium carbonate. Reduction of the ester moiety of compounds of general formula XXIII gives compounds of general formula XXIV. Reaction of compounds of general formula XXIV with hydrazines of general formula XVI gives compounds of general formula Ib (scheme 4).

Method 5:

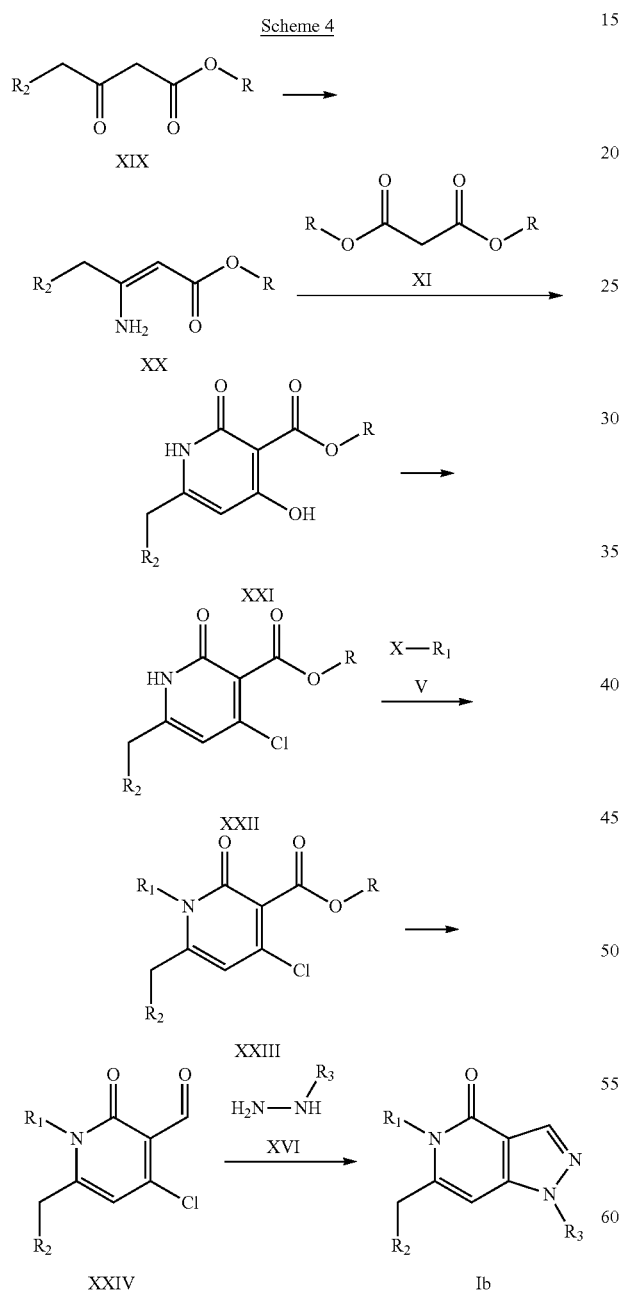

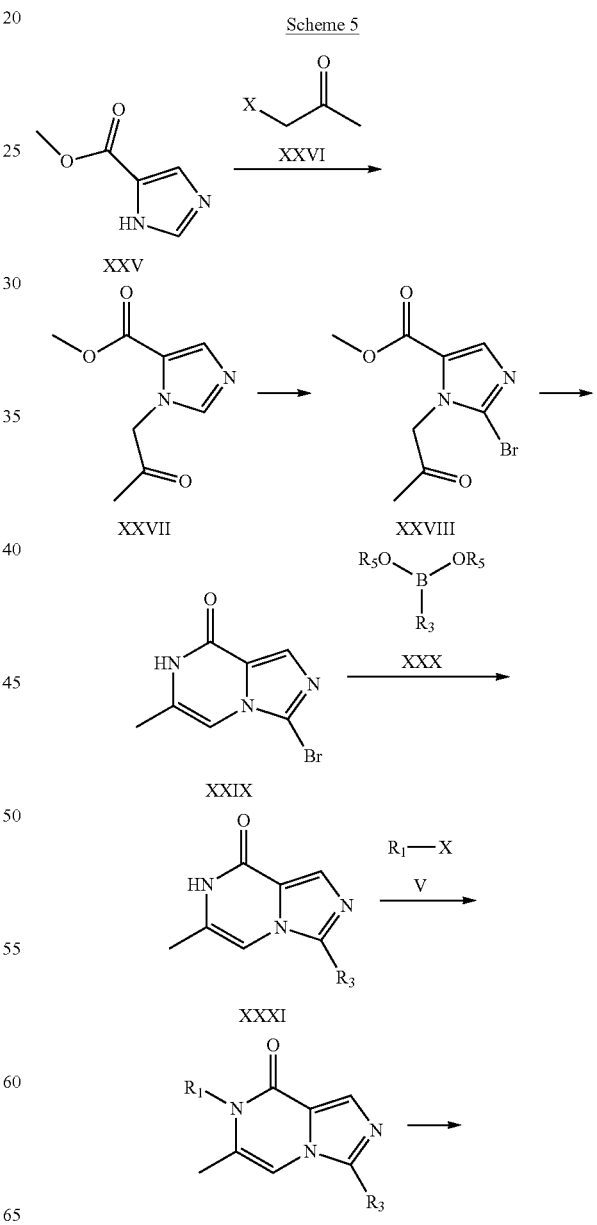

where R$_1$, R$_2$, and R$_3$ are as described for formula I; R is an alkyl group such as methyl or ethyl; and X is a halogen such as chlorine, bromine or iodine -continued

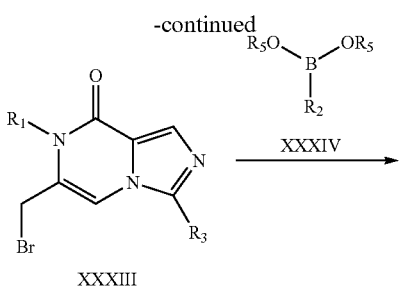

where $R_1$, $R_2$, and $R_3$ are as described for formula I; $R_5$ is hydrogen or the two $R_5$ are connected to form a cyclic boronic acid ester such as 4,4,5,5-tetramethyl-1,3,2-dioxaborolane; and X is a halogen such as chlorine, bromine or iodine Compounds of general formula XXVII (Scheme 5) can be prepared from the commercial available methyl 1H-imidazole-5-carboxylate XXV (CAS: 17325-26-7) by reaction with an α-halogenated ketone with general formula XXVI in the presence of a base exemplified but not limited to potassium carbonate. Treating imidazole XXVII with a brominating reagent exemplified but not limited to N-bromosuccinimide (NBS) in the presence of a radical initiator exemplified by but not limited to azobisisobutyronitrile (AIBN) gives imidazole XXVIII. Compounds of general formula XXIX are formed by treatment imidazole XXVIII with ammonium acetate. Compounds of the general formula XXXI can be prepared from intermediate XXIX using standard cross-coupling reaction conditions exemplified by but not limited to a Suzuki-Miyaura cross-coupling reaction. Such conditions for the cross-coupling reaction are exemplified by but not limited to using; a boronic acid ester of general formula XXX, potassium carbonate as the base, and PdCl$_2$(dppf) as the catalyst. In some examples $R_3$ contains an unsaturated carbon-carbon bond which can be reduced by hydrogenation under conditions known to the person skilled in the art. Compounds of general formula XXXI can be alkylated with compounds of general formula V in the presence of a base such as but not limited to potassium carbonate or cesium carbonate to give compounds of general formula XXXII. Treating compounds of general formula XXXII with a brominating reagent exemplified but not limited to N-bromosuccinimide (NBS) in the presence of a radical initiator exemplified by but not limited to azobisisobutyronitrile (AIBN) gives compounds of general formula XXXIII. Reaction of compounds of general formula XXXIII with compounds of general formula XXXIV in the presence of a palladium catalyst such as PdCl$_2$(dppf) and a base such as potassium carbonate gives compounds of general formula Ic.

Method 6:

Scheme 6

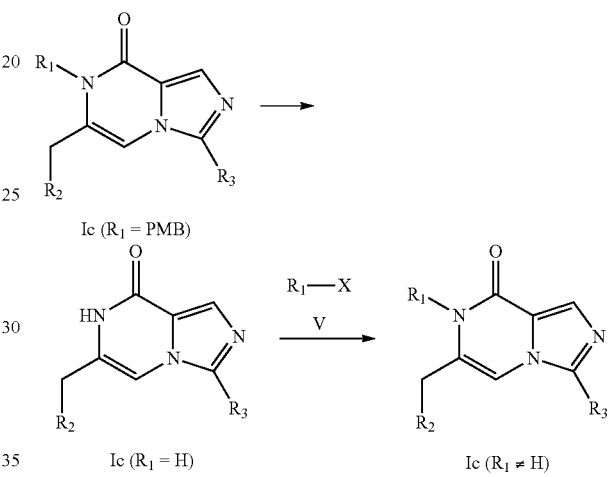

where $R_1$, $R_2$, and $R_3$ are as described for formula I; and X is a halogen such as chlorine, bromine or iodine Compounds of general formula Ic, where $R_1$ is hydrogen (Scheme 6) can be prepared by treatment of compounds of general formula Ic, where $R_1$ is para-methoxy benzyl (PMB) with an acid such as trifluoroacetic acid. Compounds of general formula Ic, where $R_1$ is hydrogen can be alkylated with compounds of general formula V in the presence of a base such as but not limited to potassium carbonate or cesium carbonate to give compounds of general formula Ic.

Method 7:

Scheme 7

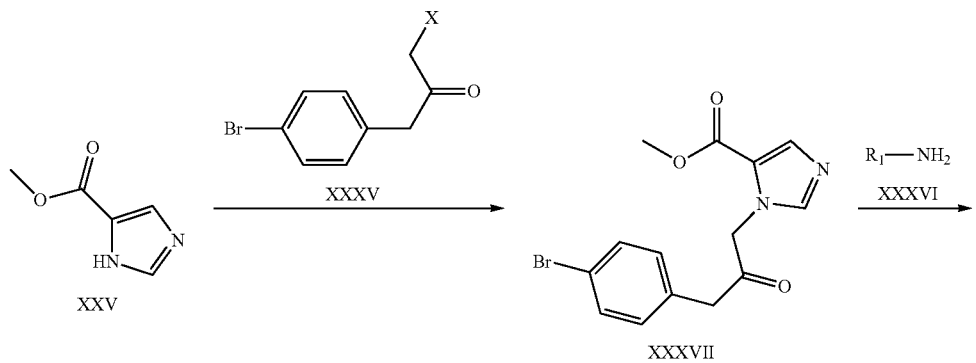

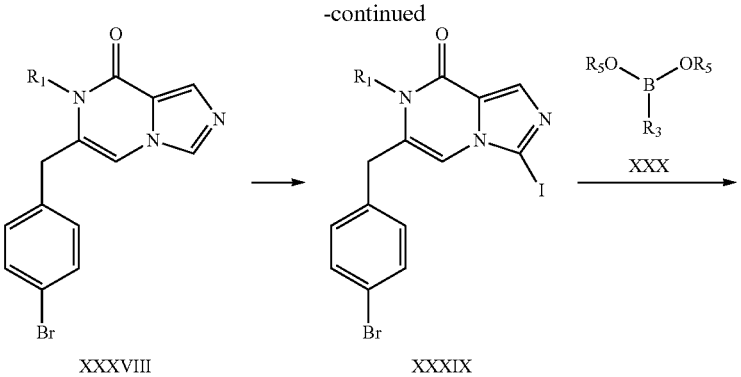

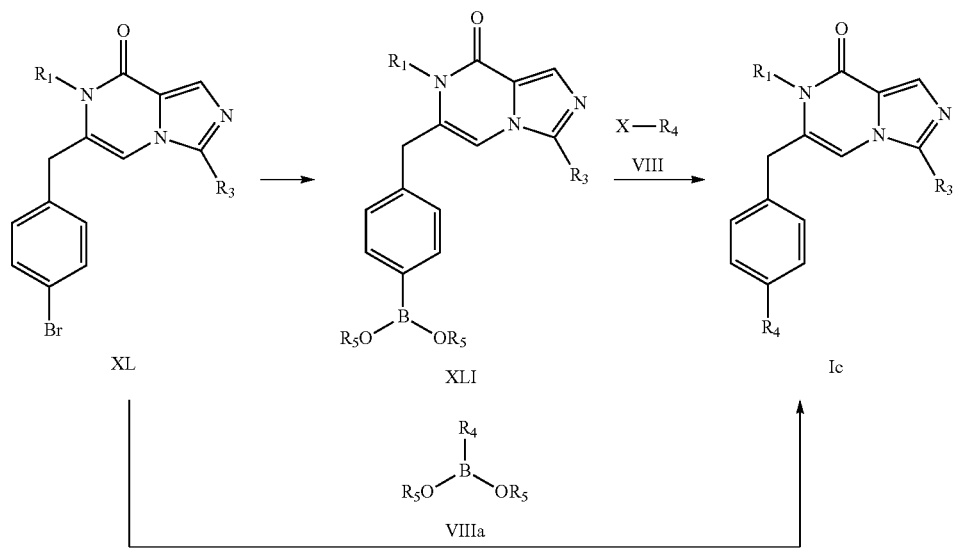

where $R_1$ and $R_3$ are as described for formula I; $R_4$ is phenyl or a heteroaromatic group; all of which can be substituted one or more times with one or more substituents selected from the group consisting of methyl, halogen, hydroxy, cyano or methoxy; $R_5$ is hydrogen or the two $R_5$ are connected to form a cyclic boronic acid ester such as 4,4,5,5-tetramethyl-1,3,2-dioxaborolane; and X is a halogen such as chlorine, bromine or iodine Compound XXXVII (Scheme 7) can be prepared from the commercial available methyl 1H-imidazole-5-carboxylate XXV (CAS: 17325-26-7) by reaction with an α-halogenated ketone with general formula XXXV in the presence of a base exemplified but not limited to potassium carbonate. Treating imidazole XXXVII with an amine of general formula XXXVI gives compounds of general formula XXXVIII. Treatment of compounds of general formula XXXVIII with a base such as tetramethylpiperidinylmagnesium chloride lithium chloride (TMPMgCl.LiCl) followed by reaction with iodine gives compounds of general formula XXXIX. Compounds of the general formula XL can be prepared from intermediate XXXIX using standard cross-coupling reaction conditions exemplified by but not limited to a Suzuki-Miyaura cross-coupling reaction. Such conditions for the cross-coupling reaction are exemplified by but not limited to using a boronic acid ester of general formula XXX, potassium carbonate as the base, and Pd(dppf)Cl$_2$ as the catalyst. Reaction of compounds of general formula XL with a reagent such as 4,4,4',4',5,5,5',5'-octamethyl-2,2'-bi(1,3,2-dioxaborolane) in the presence of a palladium catalyst such as PdCl$_2$(dppf) and a base such as potassium acetate gives compounds of general formula XLI. Reaction of compounds of general formula XLI with compounds of general formula VIII in the presence of a palladium catalyst such as PdCl$_2$(dppf) and a base such as cesium carbonate gives compounds of general formula Ic. Alternatively, compounds of general formula XL can react with compounds of general formula VIIIa in the presence of a palladium catalyst such as PdCl$_2$(dppf) ([1,1'-bis(diphenylphosphino)ferrocene]dichloropalladium(II)) and a base such as cesium carbonate to give compounds of general formula Ic. In some examples $R_3$ contains an unsaturated carbon-carbon bond which can be reduced by hydrogenation under conditions known to the person skilled in the art.

Method 8:

Scheme 8

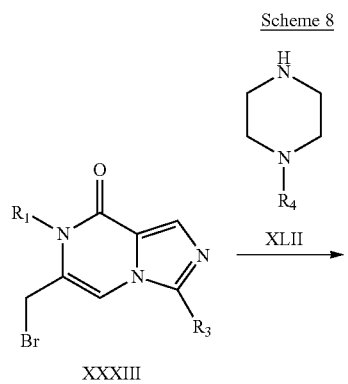

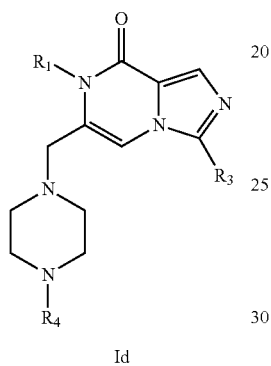

where $R_1$, $R_2$, and $R_3$ are as described for formula I; $R_4$ is phenyl or a heteroaromatic group; all of which can be substituted one or more times with one or more substituents selected from the group consisting of methyl, halogen, hydroxy, cyano or methoxy Compounds of general formula Id can be obtained by the reaction of compounds of general formula XXXIII with compounds of general formula XLII in the presence of a base such as N,N-diisopropylethylamine.

Method 9:

Scheme 9

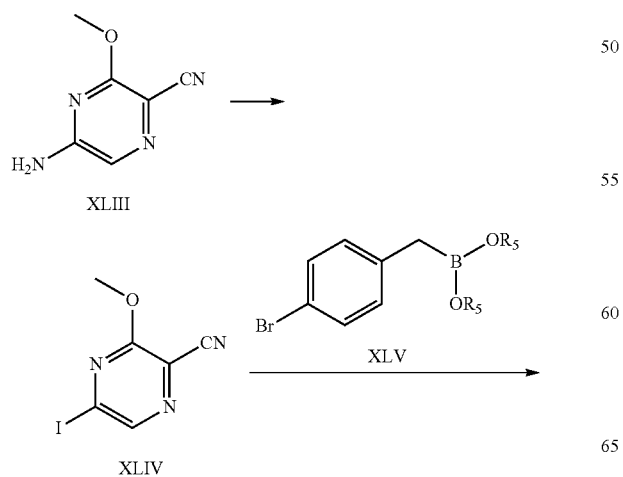

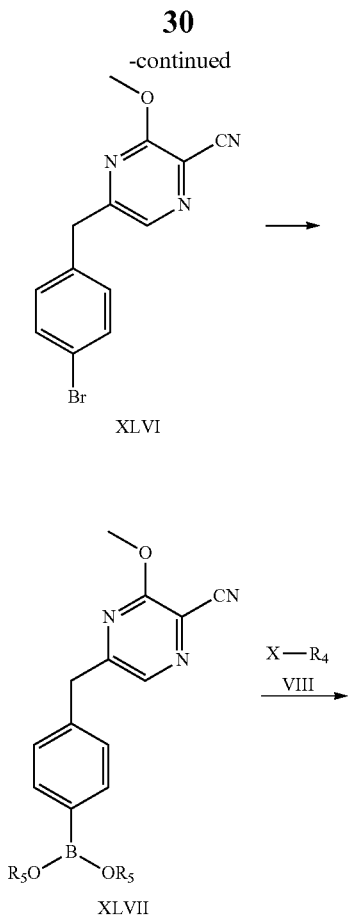

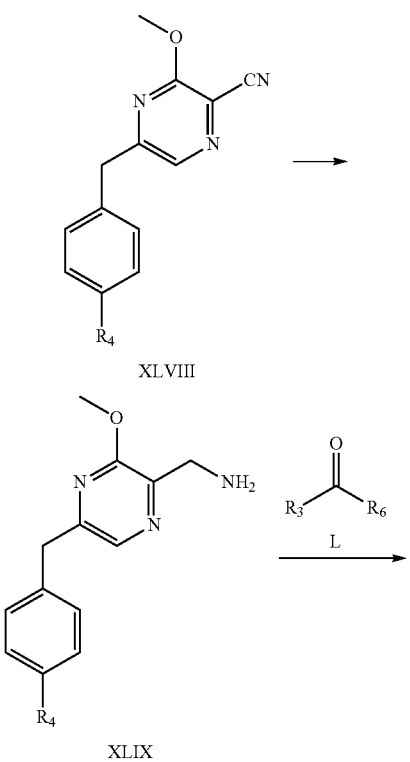

-continued

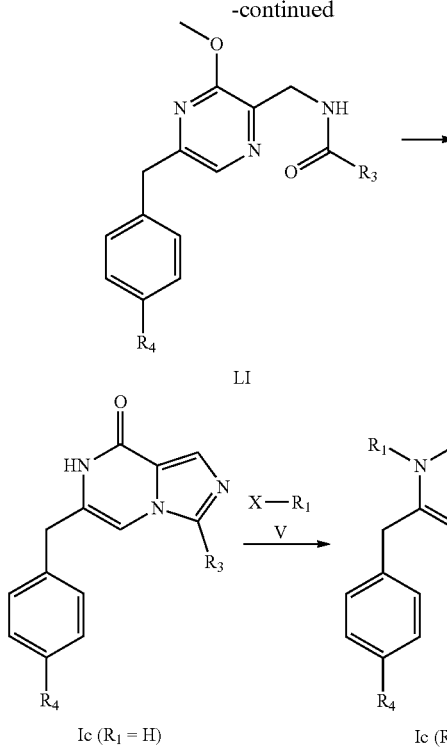

where $R_1$, $R_2$, and $R_3$ are as described for formula I; $R_4$ is phenyl or a heteroaromatic group; all of which can be substituted one or more times with one or more substituents selected from the group consisting of methyl, halogen, hydroxy, cyano or methoxy; and $R_5$ is hydrogen or the two $R_5$ are connected to form a cyclic boronic acid ester such as 4,4,5,5-tetramethyl-1,3,2-dioxaborolane; $R_6$ is hydroxy, chlorine or $R_3CO_2$—; and X is a halogen such as chlorine, bromine or iodine Compound XLIV can be prepared by treatment of compound XLIII with a reagent such as isoamyl nitrite and methyleniodide in the presence of copper(I)iodide. Reaction of compound XLIV with compound XLV in the presence of a palladium catalyst such as $PdCl_2(dppf)$ and a base such as potassium carbonate gives compound XLVI. Reaction of compound XLVI with a reagent such as 4,4,4',4',5,5,5',5'-octamethyl-2,2'-bi(1,3,2-dioxaborolane) in the presence of a palladium catalyst such as $PdCl_2(dppf)$ and a base such as potassium acetate gives compounds of general formula XLVII. Compounds of the general formula XLVIII can be prepared from intermediate XLVII using standard cross-coupling reaction conditions exemplified by but not limited to a Suzuki-Miyaura cross-coupling reaction. Such conditions for the cross-coupling reaction are exemplified by but not limited to using; a compound of general formula VIII, potassium acetate as the base, and $Pd(dppf)Cl_2$ as the catalyst. Reduction of the cyano moiety of compounds of general formula XLVIII can be accomplished by treatment with hydrogen in the presence of a catalyst such as palladium on carbon to give compounds of general formula XLIX. Treatment of compounds of general formula XLIX with carboxylic acid chloride or carboxylic anhydride of general formula L in the presence of a base such as triethylamine or treatment of compounds of general formula XLIX with carboxylic acid of general formula L in the presence of an amide coupling reagent such as HATU (1-[bis(dimethylamino)methylene]-1H-1,2,3-triazolo[4,5-b]pyridinium 3-oxid hexafluorophosphate) gives compounds of general formula LI. Compounds of general formula Ic, where $R_1$ is hydrogen can be obtained by treatment of compounds of general formula LI with a reagent such as phosphoryl chloride followed by subjection to hydrolysis conditions such as aqueous hydrochloric acid. Compounds of general formula Ic, where $R_1$ is hydrogen can be alkylated with compounds of general formula V in the presence of a base such as but not limited to potassium carbonate or cesium carbonate to give compounds of general formula Ic, where $R_1$ is not hydrogen.

LC-MS Methods

Method A:

A Waters Acquity UPLC-MS was used. Column: Acquity UPLC BEH C18 1.7 μm; 2.1×50 mm; Column temperature: 60° C.; Solvent system: A=water/trifluoroacetic acid (99.965:0.035) and B=acetonitrile/water/trifluoroacetic acid (94.965:5:0.035); Method: Linear gradient elution with A:B=90:10 to 0:100 in 1.0 minutes and with a flow rate of 1.2 mL/min.

Method B:

An Agilent 1200 LCMS system with ELS detector was used. Column: Waters XBridge ShieldRP18, 2.1×50 mm, 5 μm; Column temperature: 40° C.; Solvent system: A=water/ammonia (99.95:0.05) and B=acetonitrile; Method: Linear gradient elution with A:B=95:5 to 0:100 in 4.0 minutes and with a flow rate of 0.8 mL/min.

Method C:

An Agilent 1200 LCMS system with ELS detector was used. Phenomenex Luna-C18, 5 μm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/min.

Method D:

An Agilent 1200 LCMS system with ELS detector was used. Phenomenex Luna-C18, 5 μm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=90:10 to 0:100 in 4.0 minutes and with a flow rate of 0.8 mL/min.

Preparative supercritical fluid chromatography (SFC) was performed on a Thar 80 instrument. Exemplified conditions can be, but not limited to: Column AD 250×30 mm with 20 μm particle size; Column temperature: 38° C., Mobile phase: Supercritical $CO_2$/EtOH(0.2% $NH_3H_2O$)=45/55.

INTERMEDIATES

Preparation of ethyl 3-amino-4-(4-bromophenyl)but-2-enoate

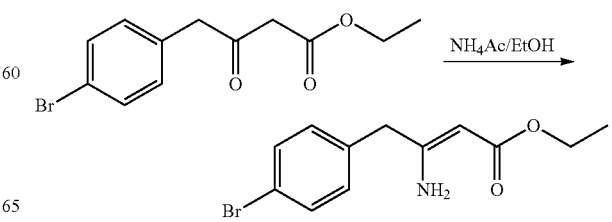

To a solution of ethyl 4-(4-bromophenyl)-3-oxobutanoate (5 g, 17.5 mmol) in dry ethanol (50 mL) was added NH₄OAc (6.76 g, 87.7 mmol). The mixture was heated at 80° C. for 3 hours. The mixture was concentrated and the residue was partitioned between ethyl acetate (50 mL) and water (50 mL). The organic layer was washed with water (50 mL), brine (50 mL), dried over Na₂SO₄, filtered and concentrated to give ethyl 3-amino-4-(4-bromophenyl)but-2-enoate (5 g).

Preparation of ethyl 6-(4-bromobenzyl)-4-hydroxy-2-oxo-1,2-dihydropyridine-3-carboxylate

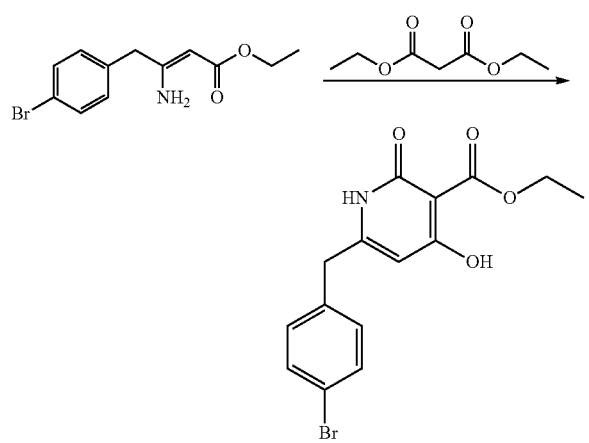

Na (291 mg, 12.7 mmol) was added to ethanol (7 mL). The mixture was stirred until all sodium had reacted. To the resulting solution was added diethyl malonate (1.78 g, 11.1 mmol). The mixture was stirred at room temperature for 1 hour. Then a solution of ethyl 3-amino-4-(4-bromophenyl)but-2-enoate (3 g, 10.6 mmol) in ethanol (3 mL) was added. The mixture was heated at 130° C. for 15 hours. The mixture was cooled to room temperature and poured into ice-water (20 g). The mixture was acidified to pH=2 by 2N HCl and filtered, the filter cake was washed with water (50 mL) and dried under vacuum to give ethyl 6-(4-bromobenzyl)-4-hydroxy-2-oxo-1,2-dihydropyridine-3-carboxylate (3 g). ¹H NMR (DMSO-d6 400 MHz): δ 12.37 (br, 1H), 11.56 (br, 1H), 7.53 (d, J=8.4 Hz, 2H), 7.29 (d, J=8.4 Hz, 2H), 5.72 (s, 1H), 4.23 (q, J=7.2 Hz, 2H), 3.74 (s, 2H), 1.26 (t, J=7.2 Hz, 3H).

Preparation of ethyl 6-(4-bromobenzyl)-4-chloro-2-oxo-1,2-dihydropyridine-3-carboxylate

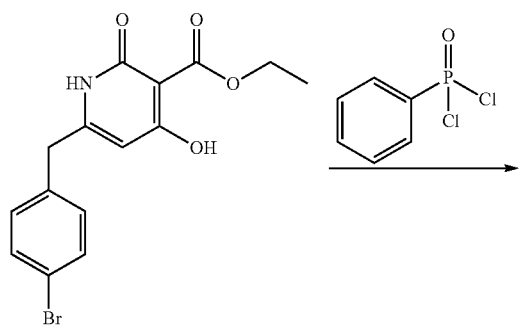

-continued

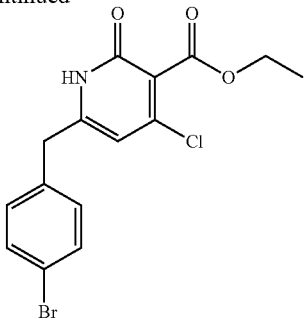

A solution of ethyl 6-(4-bromobenzyl)-4-hydroxy-2-oxo-1,2-dihydropyridine-3-carboxylate (1 g, 2.84 mmol) in dichlorophosphorylbenzene (13.9 g, 71.27 mmol, 10 mL) was heated at 60° C. for 16 hours. The mixture was cooled to room temperature and added to ice-water (20 g). The pH of the mixture was adjusted to pH=7 by saturated aqueous NaHCO₃ solution and extracted with ethyl acetate (30 mL×2). The combined organic layers were washed with water (30 mL), brine (30 mL), dried over Na₂SO₄, filtered and concentrated. The residue was purified by flash chromatography on silica gel (using a gradient of ethyl acetate and petroleum ether) to give ethyl 6-(4-bromobenzyl)-4-chloro-2-oxo-1,2-dihydropyridine-3-carboxylate (0.6 g).

Preparation of ethyl 6-(4-bromobenzyl)-4-chloro-1-methyl-2-oxo-1,2-dihydropyridine-3-carboxylate

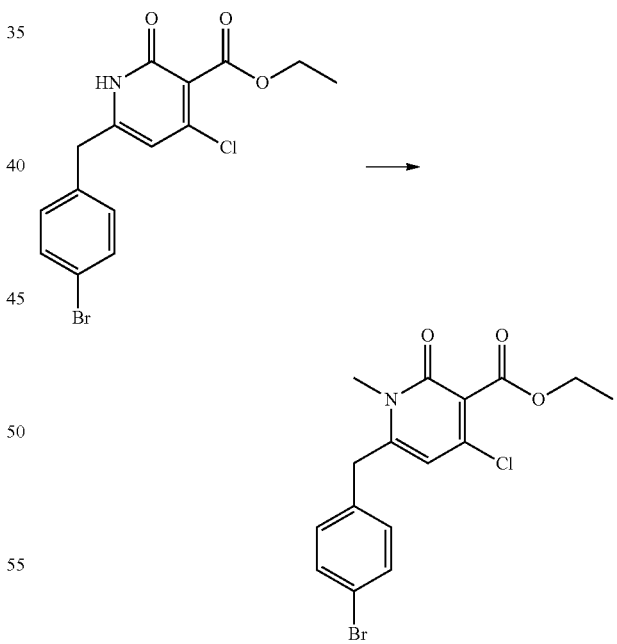

To a solution of ethyl 6-(4-bromobenzyl)-4-chloro-2-oxo-1,2-dihydropyridine-3-carboxylate (2.23 g, 6.02 mmol) in dry DMF (20 mL) was added methyl iodide (812 mg, 5.72 mmol) and Na₂CO₃ (1.28 g, 12.0 mmol). The mixture was stirred at room temperature for 2 hours. Water (30 mL) was added. The mixture was extracted with ethyl acetate (50 mL×2). The combined organic layers were washed with water (50 mL×2), brine (50 mL), dried over Na₂SO₄, filtered and concentrated. The residue was purified by flash chromatography on silica gel (using a gradient of ethyl acetate and petroleum ether) to give ethyl 6-(4-bromobenzyl)-4-chloro-1-methyl-2-oxo-1,2-dihydropyridine-3-carboxylate (1.2 g). $^1$H NMR (CDCl$_3$ 400 MHz): δ 7.50 (d, J=8.4 Hz, 2H), 7.02 (d, J=8.4 Hz, 2H), 6.04 (s, 1H), 4.41 (q, J=7.2 Hz, 2H), 3.91 (s, 2H), 3.40 (s, 3H), 1.38 (t, J=7.2 Hz, 3H).

Preparation of 6-(4-bromobenzyl)-4-chloro-1-methyl-2-oxo-1,2-dihydropyridine-3-carbaldehyde

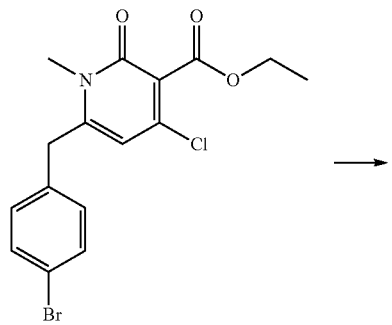

To a solution of ethyl 6-(4-bromobenzyl)-4-chloro-1-methyl-2-oxo-1,2-dihydropyridine-3-carboxylate (1.20 g, 3.12 mmol) in dry THF (10 mL) was added diisobutyl aluminium hydride (DIBAL-H) (6.24 mL) (1 M in toluene) at −78° C. The mixture was stirred at −78° C. for 2 hours. Saturated aqueous NH$_4$Cl (10 mL) was added. The mixture was filtered through celite and the filtrate was extracted with ethyl acetate (20 mL×2). The combined organic layers were washed with water (20 mL), brine (20 mL), dried over Na$_2$SO$_4$, filtered and concentrated. The residue was purified by flash chromatography on silica gel (using a gradient of ethyl acetate and petroleum ether) to give 6-(4-bromobenzyl)-4-chloro-1-methyl-2-oxo-1,2-dihydropyridine-3-carbaldehyde (0.6 g). $^1$H NMR (CDCl$_3$ 400 MHz): δ 10.30 (s, 1H), 7.45 (d, J=8.4 Hz, 2H), 6.97 (d, J=8.4 Hz, 2H), 6.00 (s, 1H), 3.88 (s, 2H), 3.41 (s, 3H).

Preparation of 6-(4-bromobenzyl)-5-methyl-1-(tetrahydro-2H-pyran-4-yl)-1H-pyrazolo[4,3-c]pyridin-4(5H)-one

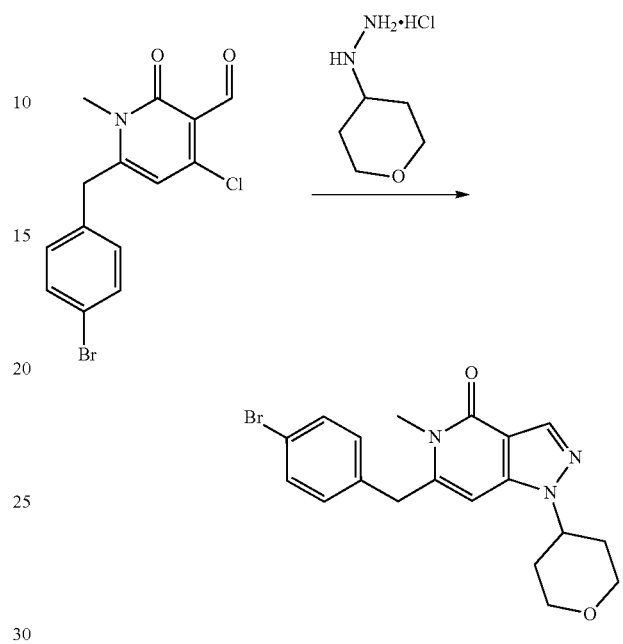

To a solution of 6-(4-bromobenzyl)-4-chloro-1-methyl-2-oxo-1,2-dihydropyridine-3-carbaldehyde (300 mg, 0.88 mmol) in 2-methoxyethanol (3 mL) was added (tetrahydro-2H-pyran-4-yl)hydrazine hydrochloride (269 mg, 1.76 mmol) and triethylamine (446 mg, 4.40 mmol). The mixture was heated under microwave irradiation at 170° C. for 1 hour. The mixture was concentrated and water (20 mL) was added. The mixture was extracted with ethyl acetate (20 mL×2). The combined organic layers were washed with water (20 mL), brine (20 mL), dried over Na$_2$SO$_4$, filtered and concentrated. The residue was purified by flash chromatography on silica gel (using a gradient of ethyl acetate and petroleum ether) to give 6-(4-bromobenzyl)-5-methyl-1-(tetrahydro-2H-pyran-4-yl)-1H-pyrazolo[4,3-c]pyridin-4(5H)-one (200 mg). $^1$H NMR (CDCl$_3$ 400 MHz): δ 8.16 (s, 1H), 7.48 (d, J=8.4 Hz, 2H), 7.04 (d, J=8.4 Hz, 2H), 6.24 (s, 1H), 4.40-4.36 (m, 1H), 4.17-4.13 (m, 2H), 4.02 (s, 2H), 3.57 (t, J=10.0 Hz, 2H), 2.42-2.31 (m, 2H), 3.42 (s, 3H), 1.95-1.92 (m, 2H).

Preparation of 5-methyl-1-(tetrahydro-2H-pyran-4-yl)-6-(4-(4,4,5,5-tetramethyl-1,3,2-dioxaborolan-2-yl)benzyl)-1H-pyrazolo[4,3-c]pyridin-4(5H)-one

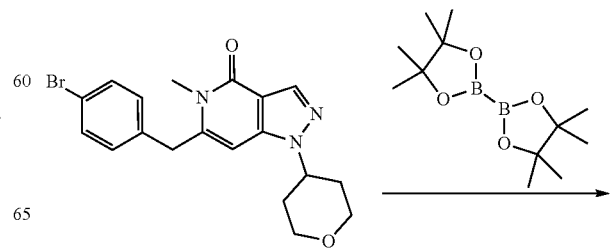

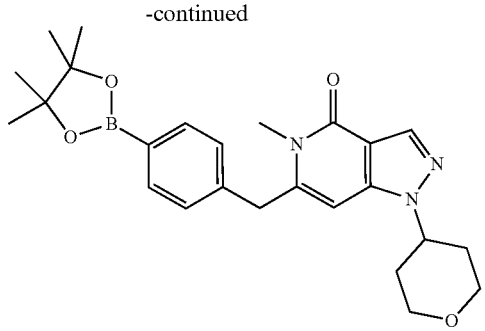

To a solution of 6-(4-bromobenzyl)-5-methyl-1-(tetrahydro-2H-pyran-4-yl)-1H-pyrazolo[4,3-c]pyridin-4(5H)-one (50 mg, 0.12 mmol) in dioxane (2 mL) was added 4,4,4',4',5,5,5',5'-octamethyl-2,2'-bi(1,3,2-dioxaborolane) (47 mg, 0.19 mmol), KOAc (37 mg, 0.37 mmol) and Pd(dppf)Cl$_2$ (9 mg, 0.01 mmol). The mixture was degasssed with N$_2$ and heated at 100° C. for 16 hours. The mixture was cooled to 30° C. The solution of 5-methyl-1-(tetrahydro-2H-pyran-4-yl)-6-(4-(4,4,5,5-tetramethyl-1,3,2-dioxaborolan-2-yl)benzyl)-1H-pyrazolo[4,3-c]pyridin-4(5H)-one (59 mg) in dioxane (2 mL) was directly used for the next step.

Preparation of 7-[(4-methoxyphenyl)methyl]-6-methyl-3-tetrahydropyran-4-yl-imidazo[1,5-a]pyrazin-8-one

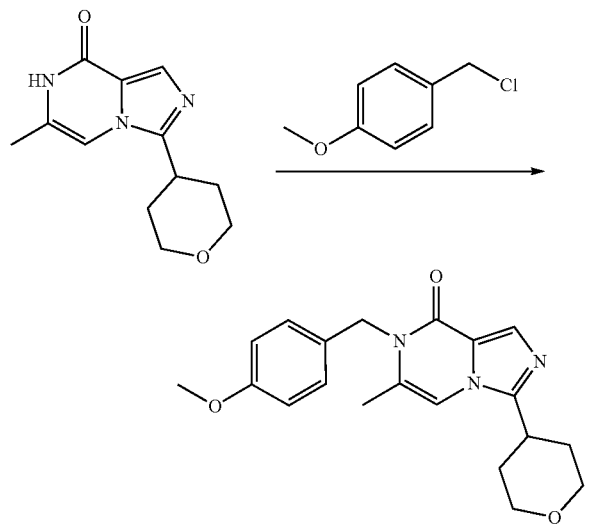

To a solution of 6-methyl-3-tetrahydropyran-4-yl-7H-imidazo[1,5-a]pyrazin-8-one (4.50 g, 19.3 mmol) and 1-(chloromethyl)-4-methoxy-benzene (3.93 g, 25.1 mmol, 3.42 mL) in DMF (40 mL) was added Cs$_2$CO$_3$ (12.57 g, 38.58 mmol). The mixture was stirred at 60° C. for 12 hours. The reaction mixture was concentrated under reduced pressure to remove DMF. The residue was purified by flash silica gel chromatography (using a gradient of ethyl and petroleum ether) to give 7-[(4-methoxyphenyl)methyl]-6-methyl-3-tetrahydropyran-4-yl-imidazo[1,5-a]pyrazin-8-one (5.70 g). $^1$H NMR (CDCl$_3$ 400 MHz): δ 7.92 (s, 1H), 7.16 (d, J=7.2 Hz, 2H), 6.85 (d, J=6.4 Hz, 2H), 6.73 (s, 1H), 5.17 (s, 2H), 4.13-4.11 (m, 2H), 3.78 (s, 3H), 3.58 (t, J=11.6 Hz, 2H), 3.11-3.05 (m, 1H), 2.20-2.08 (m, 5H), 1.90-1.86 (m, 2H).

Preparation of 6-(bromomethyl)-7-(4-methoxybenzyl)-3-(tetrahydro-2H-pyran-4-yl)imidazo[1,5-a]pyrazin-8(7H)-one

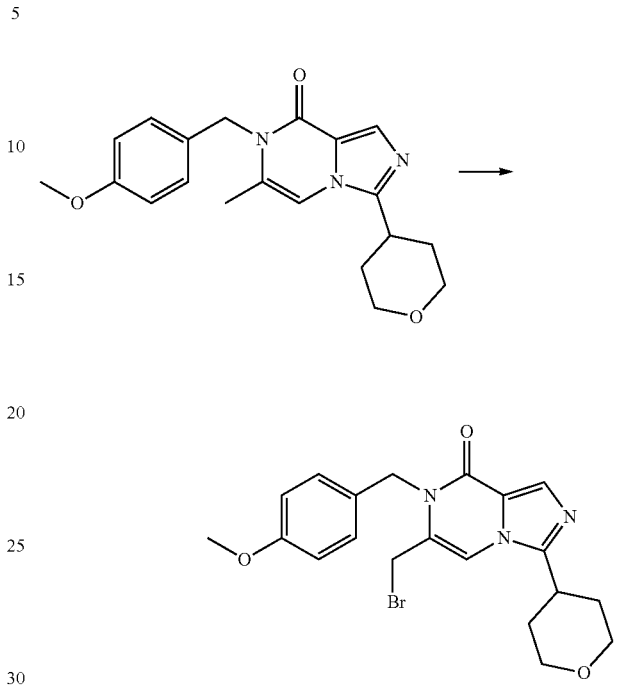

To a solution of 7-[(4-methoxyphenyl)methyl]-6-methyl-3-tetrahydropyran-4-yl-imidazo[1,5-a]pyrazin-8-one (5.20 g, 14.7 mmol) in CHCl$_3$ (220 mL) was added AIBN (483 mg, 2.94 mmol) and NBS (2.49 g, 13.97 mmol). The mixture was stirred at 50° C. for 12 hours. The reaction mixture was diluted with water (30 mL) and extracted with dichloromethane (100 mL×2). The combined organic layers were washed with brine (30 mL), dried over anhydrous Na$_2$SO$_4$, filtered and concentrated. The residue was purified by column chromatography on silica gel (using a gradient of ethyl acetate and petroleum ether) to give 6-(bromomethyl)-7-(4-methoxybenzyl)-3-(tetrahydro-2H-pyran-4-yl)imidazo[1,5-a]pyrazin-8(7H)-one (2 g). $^1$H NMR (CDCl$_3$ 400 MHz): δ 7.96 (s, 1H), 7.16 (d, J=8.8 Hz, 2H), 7.05 (s, 1H), 6.86 (d, J=9.2 Hz, 2H), 5.42 (s, 2H), 4.21 (s, 2H), 4.15-4.12 (m, 2H), 3.78 (s, 3H), 3.58 (t, J=10.0 Hz, 2H), 3.14-3.08 (m, 1H), 2.18-2.09 (m, 2H), 1.90-1.87 (m, 2H).

Preparation of 6-[(4-bromophenyl)methyl]-1-tetrahydropyran-4-yl-5H-pyrazolo[3,4-d]pyrimidin-4-one

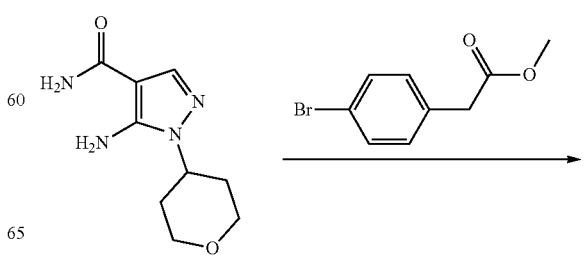

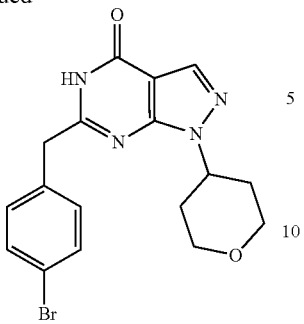

To a solution of 5-amino-1-tetrahydropyran-4-yl-pyrazole-4-carboxamide (4.78 g, 22.7 mmol) in dry THF (200 mL) was added methyl 2-(4-bromophenyl)acetate (7.81 g, 34.1 mmol) and t-BuOK (1 M, 45 mL) in THF (45 mL). The mixture was stirred at 80° C. for 16 hours. The mixture was quenched with water (30 mL) and adjusted with HCl (1N, aqueous) to pH=7.

The mixture was filtered. The filter cake was washed with water (20 mL×3) to give 6-[(4-bromophenyl)methyl]-1-tetrahydropyran-4-yl-5H-pyrazolo[3,4-d]pyrimidin-4-one (5 g).

Preparation of 6-[(4-bromophenyl)methyl]-5-methyl-1-tetrahydropyran-4-yl-pyrazolo[3,4-d]pyrimidin-4-one

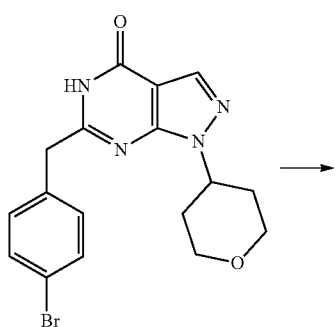

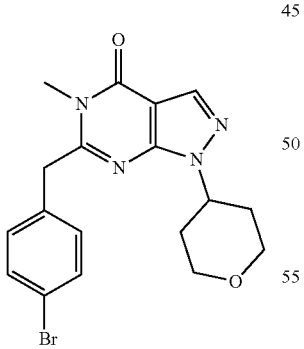

To a solution of 6-[(4-bromophenyl)methyl]-1-tetrahydropyran-4-yl-5H-pyrazolo[3,4-d]pyrimidin-4-one (4.33 g, 11.12 mmol) and iodomethane (1.74 g, 12.2 mmol, 0.76 mL) in CH$_3$CN (150 mL) was added Cs$_2$CO$_3$ (7.25 g, 22.2 mmol). The mixture was stirred at room temperature for 2 hours. The mixture was concentrated under vacuum. The residue was diluted with water (50 mL). The residue was filtered. The filter cake was washed with water (50 mL×2) to give 6-[(4-bromophenyl)methyl]-5-methyl-1-tetrahydropyran-4-yl-pyrazolo[3,4-d]pyrimidin-4-one (2.15 g)

Preparation of 5-methyl-1-(tetrahydro-2H-pyran-4-yl)-6-(4-(4,4,5,5-tetramethyl-1,3,2-dioxaborolan-2-yl)benzyl)-1,5-dihydro-4H-pyrazolo[3,4-d]pyrimidin-4-one

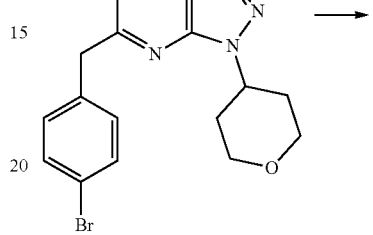

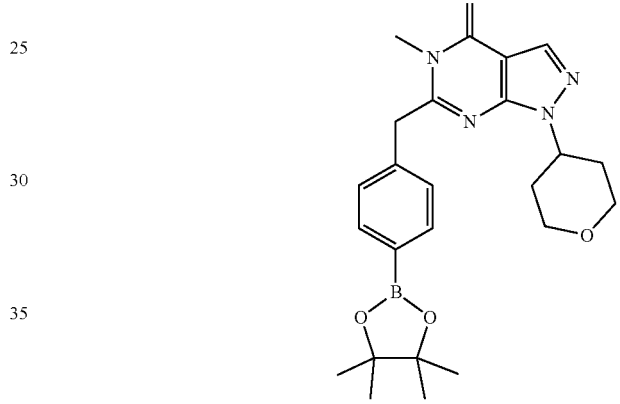

To a solution of 6-[(4-bromophenyl)methyl]-5-methyl-1-tetrahydropyran-4-yl-pyrazolo[3,4-d]pyrimidin-4-one (200 mg, 0.50 mmol) and 4,4,4',4',5,5,5',5'-octamethyl-2,2'-bi(1,3,2-dioxaborolane) (189 mg, 0.74 mmol) in dioxane (5 mL) was added PdCl$_2$(dppf) (36 mg, 0.050 mmol) and KOAc (146 mg, 1.49 mmol). The mixture was degassed and purged with N$_2$ 3 times. The mixture was stirred at 100° C. for 16 hours. The mixture was concentrated under vacuum to give 5-methyl-1-(tetrahydro-2H-pyran-4-yl)-6-(4-(4,4,5,5-tetramethyl-1,3,2-dioxaborolan-2-yl)benzyl)-1,5-dihydro-4H-pyrazolo[3,4-d]pyrimidin-4-one (223 mg).

Preparation of methyl 1-(2-oxopropyl)-1H-imidazole-5-carboxylate

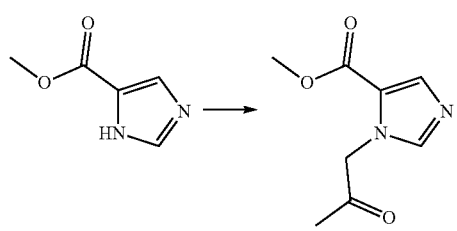

A mixture of methyl 1H-imidazole-5-carboxylate (20 g, 0.16 mol), 1-chloropropan-2-one (22 g, 0.24 mol), and potassium carbonate (44 g, 0.32 mol) in acetone (400 mL) was stirred at 30° C. for 12 hours. The reaction mixture was concentrated under vacuum, the residue was diluted with ethyl acetate (200 mL) and washed with water (50 mL×3). The organic layer was dried over Na$_2$SO$_4$ and concentrated under vacuum. The residue was purified by flash chromatography using a gradient of petroleum ether and ethyl acetate to give methyl 1-(2-oxopropyl)-1H-imidazole-5-carboxylate (10 g).

Preparation of methyl 2-bromo-1-(2-oxopropyl)-1H-imidazole-5-carboxylate

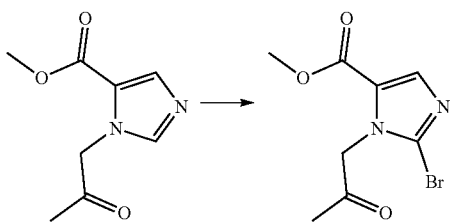

A mixture of methyl 1-(2-oxopropyl)-1H-imidazole-5-carboxylate (10 g, 55 mmol), N-bromosuccinimide (12.7 g, 71.4 mmol) and azobisisobutyronitrile (1.8 g, 11 mmol) in chloroform (100 mL) was stirred at 50° C. for 12 hours. The mixture was concentrated under vacuum. The residue was purified by flash chromatography using a gradient of petroleum ether and ethyl acetate to give methyl 2-bromo-1-(2-oxopropyl)-1H-imidazole-5-carboxylate (13 g).

Preparation of 3-Bromo-6-methylimidazo[1,5-a]pyrazin-8(7H)-one

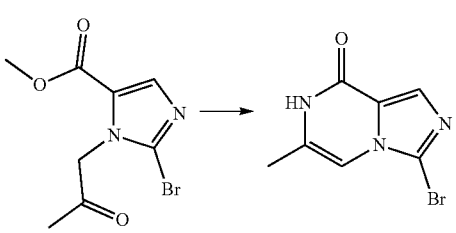

A mixture of methyl 2-bromo-1-(2-oxopropyl)-1H-imidazole-5-carboxylate (14 g, 50 mmol) and ammonium acetate (16.5 g, 215 mmol) in 1,4-dioxane (150 mL) was stirred at 60° C. for 12 hours. The mixture was then stirred at 90° C. for another 24 hours. The reaction mixture was concentrated under vacuum and the residue was diluted with ethyl acetate (600 mL) and washed with water (100 mL×3). The combined organic phases were dried with anhydrous Na$_2$SO$_4$ and concentrated under vacuum. The residue was purified by flash chromatography using a gradient of petroleum ether and ethyl acetate to give 3-bromo-6-methylimidazo[1,5-a]pyrazin-8(7H)-one (4.8 g).

Preparation of 3-(3,6-Dihydro-2H-pyran-4-yl)-6-methylimidazo[1,5-a]pyrazin-8(7H)-one

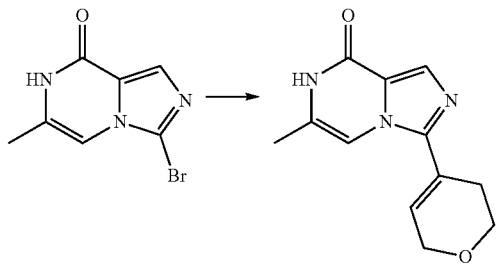 [SMILES: Cc1cn2c(Br)ncc2c(=O)[nH]1 ; Cc1cn2c(C3=CCOCC3)ncc2c(=O)[nH]1]

A mixture of 3-bromo-6-methylimidazo[1,5-a]pyrazin-8(7H)-one (4.5 g, 20 mmol), 2-(3,6-dihydro-2H-pyran-4-yl)-4,4,5,5-tetramethyl-1,3,2-dioxaborolane (4.97 g, 23.7 mmol), Pd(dppf)Cl$_2$ (2.9 g, 3.95 mmol), potassium carbonate (5.5 g, 39 mmol) and water (10 mL) in 1,4-dioxane (40 mL) was stirred at 100° C. for 12 hours. The mixture was filtered and the filtrate was concentrated in vacuo. The residue was purified by flash chromatography on silica gel using a gradient of dichloromethane and methanol to give 3-(3,6-dihydro-2H-pyran-4-yl)-6-methylimidazo[1,5-a]pyrazin-8(7H)-one (4.0 g).

Preparation of 6-Methyl-3-(tetrahydro-2H-pyran-4-yl)imidazo[1,5-a]pyrazin-8(7H)-one

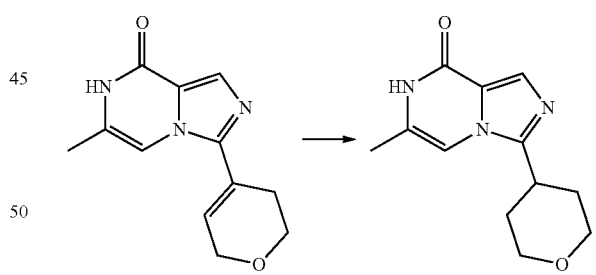

A mixture of 3-(3,6-dihydro-2H-pyran-4-yl)-6-methylimidazo[1,5-a]pyrazin-8(7H)-one (4.0 g, 17 mmol) and 10% Pd/C (300 mg) in tetrahydrofuran (15 mL) was stirred at 15° C. for 7 hours under an atmosphere of hydrogen. The reaction mixture was filtered and the filtrate was concentrated under vacuum to afford 6-methyl-3-(tetrahydro-2H-pyran-4-yl)imidazo[1,5-a]pyrazin-8(7H)-one (3.5 g).

Preparation of
1-bromo-3-(4-bromophenyl)propan-2-one

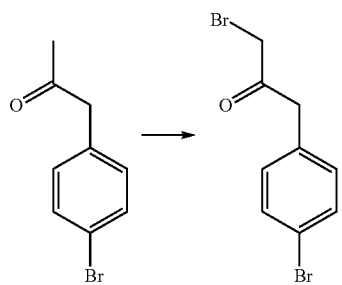

A solution of 1-(4-bromophenyl)propan-2-one (25 g, 117 mmol) in AcOH (30 mL) and aqueous HBr (15 mL) was treated with a solution of $Br_2$ (37.5 g, 235 mmol, 12.1 mL) in AcOH (50 mL) dropwise and the reaction mixture was stirred at room temperature for 4 hours. After that time, acetone (150 mL) was added and the mixture was stirred for 12 hours at room temperature. The mixture was concentrated. The residue was purified by column chromatography on silica gel (petroleum ether/ethyl acetate=100/0 to 90/10) to give 1-bromo-3-(4-bromophenyl)propan-2-one (40 g).

Preparation of methyl 1-(3-(4-bromophenyl)-2-oxo-propyl)-1H-imidazole-5-carboxylate

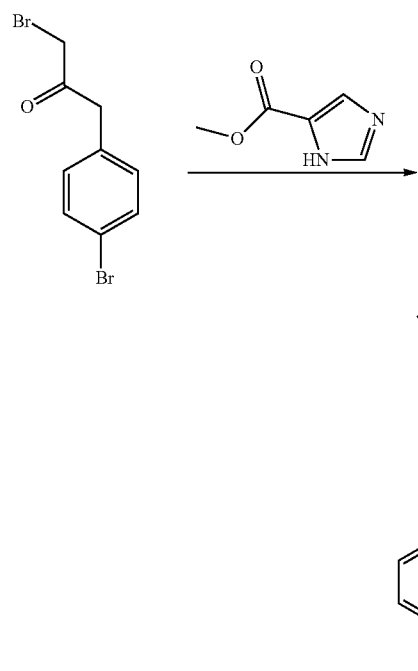

A mixture of methyl 1H-imidazole-5-carboxylate (14 g, 111 mmol), 1-(4-bromophenyl)propan-2-one (35.7 g, 122 mmol), $K_2CO_3$ (30.7 g, 222 mmol) in $CH_3CN$ (150 mL) was stirred at 30° C. for 4 hours. The mixture was diluted with ethyl acetate (200 mL) and extracted with water (100 mL×2). The combined organic layers were washed with saturated aqueous NaCl (100 mL×2), dried over $Na_2SO_4$, filtered and concentrated under reduced pressure. The residue was purified by column chromatography on silica gel (petroleum ether/ethyl acetate=3/1 to 0/1) to give methyl 1-(3-(4-bromophenyl)-2-oxopropyl)-1H-imidazole-5-carboxylate (5.6 g).

Preparation of 6-(4-bromobenzyl)-7-methylimidazo[1,5-a]pyrazin-8(7H)-one

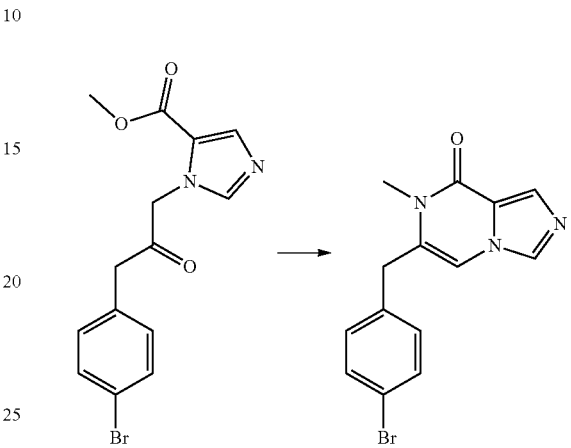

A mixture of methyl 1-(3-(4-bromophenyl)-2-oxopropyl)-1H-imidazole-5-carboxylate (1 g, 2.97 mmol) and $CH_3NH_2$ (2 M in THF, 37.07 mL) in xylene (3 mL) was stirred at 140° C. for 32 hours in a closed tube. The mixture was concentrated and the residue was purified by column chromatography on silica gel (petroleum ether/ethyl acetate=3:1 to 0:1) to give 6-(4-bromobenzyl)-7-methylimidazo[1,5-a]pyrazin-8(7H)-one (344 mg).

Preparation of 6-(4-bromobenzyl)-3-iodo-7-methyl-imidazo[1,5-a]pyrazin-8(7H)-one

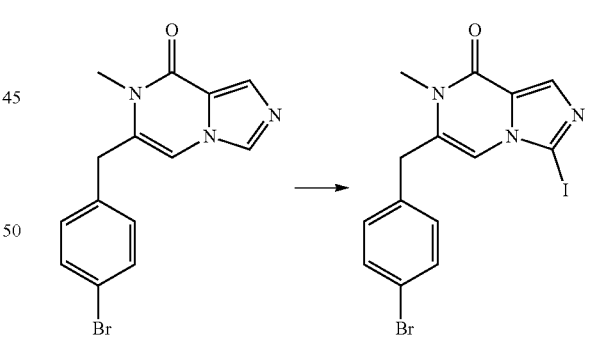

To a solution of 6-[(4-bromophenyl)methyl]-7-methyl-imidazo[1,5-a]pyrazin-8-one (344 mg, 1.08 mmol) in THF (4 mL) was added TMPMgCl.LiCl)2,2,6,6-tetramethylpiperidinylmagnesium chloride lithium chloride complex) (1 M THF, 3.24 mL) at −40° C. The mixture was stirred at −40° C. for 1 hour. Then $I_2$ (1.37 g, 5.41 mmol) in THF (2 mL) was added. The mixture was stirred at −40° C. for 2 hours. The mixture was quenched by addition saturated aqueous $NH_4Cl$ solution (20 mL) at 0° C., and then diluted with ethyl acetate (50 mL) and extracted with water (20 mL×2). The combined organic layers were washed with brine (20 mL×2), dried over $Na_2SO_4$, filtered and concentrated under reduced pressure to give 6-(4-bromobenzyl)-3-iodo-7-methylimidazo[1,5-a]pyrazin-8(7H)-one (460 mg).

Preparation of 6-(4-bromobenzyl)-3-(3,6-dihydro-2H-pyran-4-yl)-7-methylimidazo[1,5-a]pyrazin-8(7H)-one

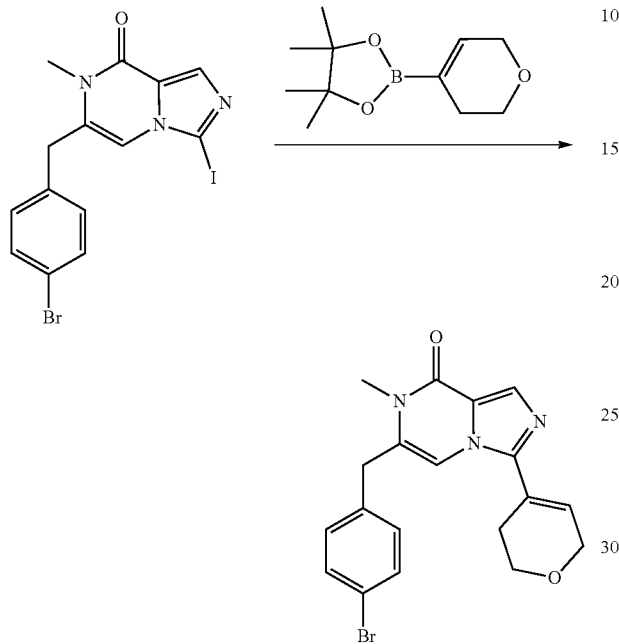

A mixture of 6-(4-bromobenzyl)-3-iodo-7-methylimidazo[1,5-a]pyrazin-8(7H)-one (520 mg, 1.17 mmol), 2-(3,6-dihydro-2H-pyran-4-yl)-4,4,5,5-tetramethyl-1,3,2-dioxaborolane (246 mg, 1.17 mmol), Pd(dppf)Cl$_2$ (43 mg, 0.059 mmol), K$_2$CO$_3$ (486 mg, 3.51 mmol) in dioxane (0.8 mL) and water (0.2 mL) was stirred at 60° C. for 2 hours. The mixture was concentrated and the residue was purified by column chromatography on silica gel (petroleum ether/ethyl acetate=3:1 to 0:1) to give 6-(4-bromobenzyl)-3-(3,6-dihydro-2H-pyran-4-yl)-7-methylimidazo[1,5-a]pyrazin-8(7H)-one (210 mg).

Preparation of 3-(3,6-dihydro-2H-pyran-4-yl)-7-methyl-6-(4-(4,4,5,5-tetramethyl-1,3,2-dioxaborolan-2-yl)benzyl)imidazo[1,5-a]pyrazin-8(7H)-one

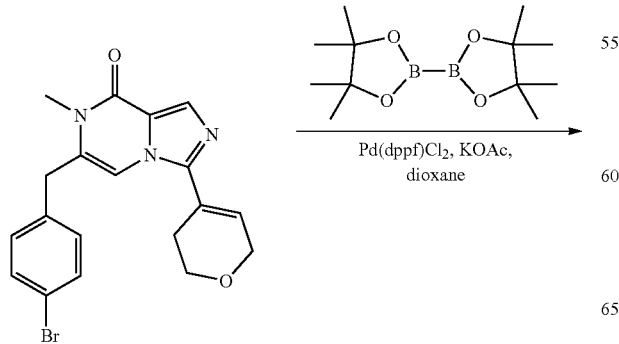

A mixture of 6-(4-bromobenzyl)-3-(3,6-dihydro-2H-pyran-4-yl)-7-methylimidazo[1,5-a]pyrazin-8(7H)-one (60 mg, 0.15 mmol), 4,4,5,5-tetramethyl-2-(4,4,5,5-tetramethyl-1,3,2-dioxaborolan-2-yl)-1,3,2-dioxaborolane (38 mg, 0.15 mmol), KOAc (44 mg, 0.45 mmol), Pd(dppf)Cl$_2$ (5 mg, 0.007 mmol) in dioxane (3 mL) was degased with N$_2$ and stirred at 100° C. for 16 hours. The mixture was concentrated and partitioned between water (5 mL) and ethyl acetate (15 mL). The organic phase was dried with Na$_2$SO$_4$ and concentrated to give a residue which was used directly in the next step.

Preparation of 5-iodo-3-methoxypyrazine-2-carbonitrile

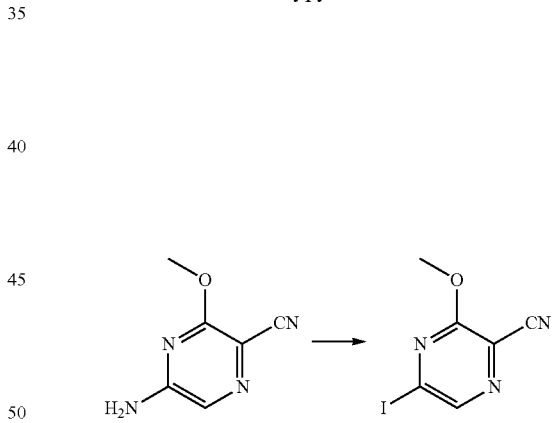

To a solution of 5-amino-3-methoxy-pyrazine-2-carbonitrile (6.1 g, 41 mmol) and CH$_2$I$_2$ (13 g, 49 mmol) in THF (100 mL) was added isoamyl nitrite (7.0 g, 61 mmol) and CuI (8.5 g, 45 mmol) under a N$_2$ atmosphere. The mixture was stirred at 75° C. for 18 hours. The mixture was filtered and the residue was washed with dichloromethane (50 mL×2), the combined filtrates were concentrated. The crude product was purified by flash chromatography on silica gel with petroleum ether/ethyl acetate=30:1 to give 5-Iodo-3-methoxy-pyrazine-2-carbonitrile (7.4 g).

Preparation of 2-(4-bromobenzyl)-4,4,5,5-tetramethyl-1,3,2-dioxaborolane

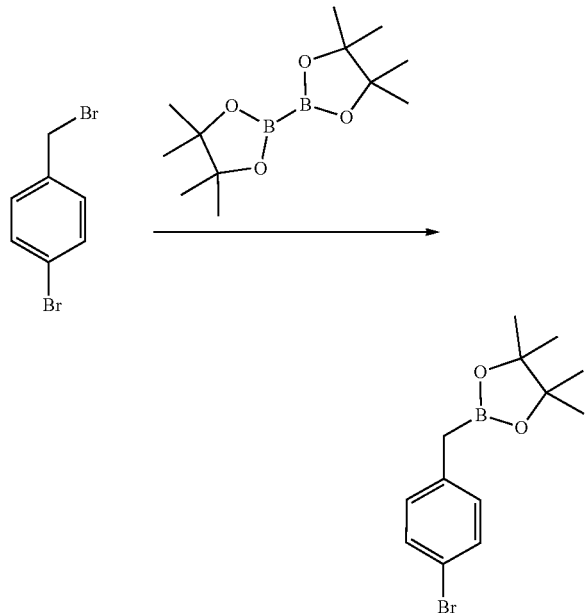

A mixture of 1-bromo-4-(bromomethyl)benzene (10 g, 40 mmol), 4,4,5,5-tetramethyl-2-(4,4,5,5-tetramethyl-1,3,2-dioxaborolan-2-yl)-1,3,2-dioxaborolane (15 g, 60 mmol), CuI (762 mg, 4 mmol), PPh₃ (1.6 g, 6.0 mmol) and lithium methoxide (3.0 g, 80 mmol) in DMF (150 mL) was degassed and purged with N₂ 3 times, the mixture was stirred at 30° C. for 18 hours under a N₂ atmosphere. The mixture was filtered and the residue was washed with ethyl acetate (30 mL×3), the combined filtrates were poured into ice-water (200 mL), and then extracted with ethyl acetate (75 mL×3). The combined organic layers were washed with brine (50 mL), dried over Na₂SO₄ and concentrated. The crude product was purified by flash chromatography on silica gel with petroleum ether/ethyl acetate=20:1 to give 2-(4-bromobenzyl)-4,4,5,5-tetramethyl-1,3,2-dioxaborolane (4.4 g).

Preparation of 5-[(4-bromophenyl)methyl]-3-methoxy-pyrazine-2-carbonitrile

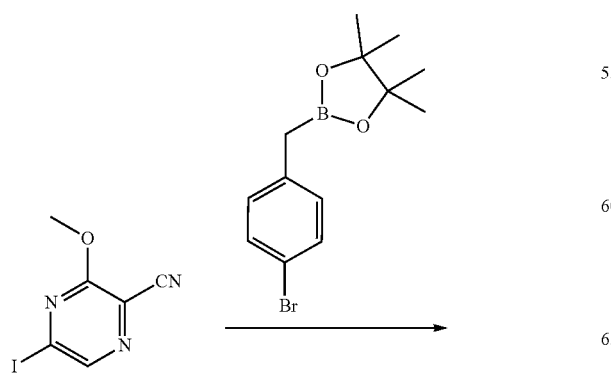

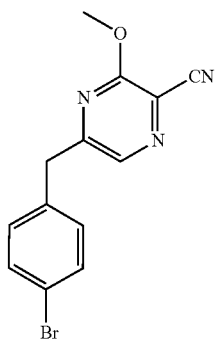

A mixture of 5-iodo-3-methoxy-pyrazine-2-carbonitrile (1.0 g, 3.8 mmol), 2-[(4-bromophenyl)methyl]-4,4,5,5-tetramethyl-1,3,2-dioxaborolane (2.3 g, 7.7 mmol), Pd(dppf)Cl₂ (280 mg, 0.40 mmol), K₂CO₃ (1.0 g, 7.7 mmol) in dioxane (16 mL) and H₂O (8 mL) was degassed and purged with N₂ 3 times, the mixture was stirred at 50° C. for 18 hours under a N₂ atmosphere. Water (30 mL) was added and the mixture was extracted with ethyl acetate (30 mL×3). The combined organic layers were washed with brine (10 mL), dried over Na₂SO₄ and concentrated. The crude product was purified by flash chromatography on silica gel with petroleum ether/ethyl acetate=20:1 to give 5-[(4-bromophenyl)methyl]-3-methoxy-pyrazine-2-carbonitrile (400 mg).

Preparation of 3-methoxy-5-(4-(4,4,5,5-tetramethyl-1,3,2-dioxaborolan-2-yl)benzyl)pyrazine-2-carbonitrile

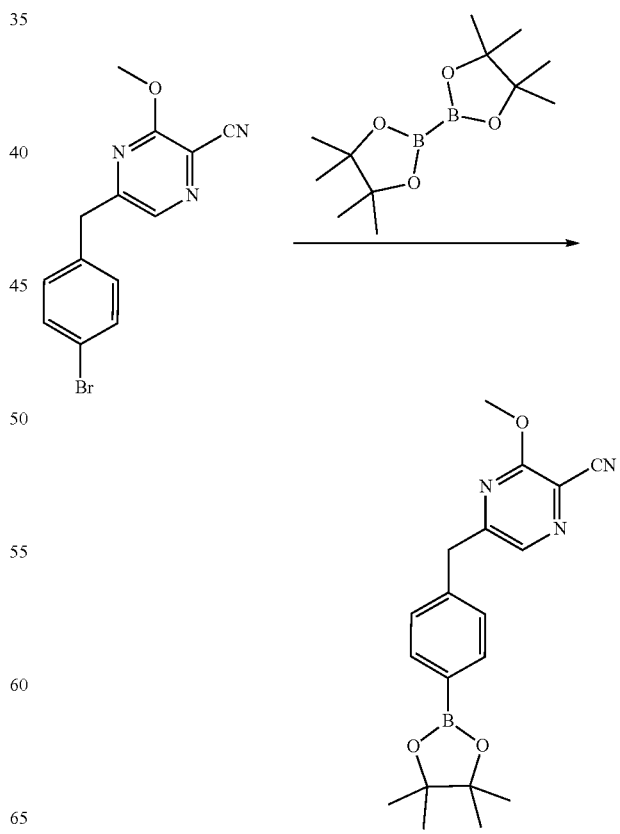

A mixture of 5-[(4-bromophenyl)methyl]-3-methoxy-pyrazine-2-carbonitrile (400 mg, 1.30 mmol), 4,4,5,5-tetramethyl-2-(4,4,5,5-tetramethyl-1,3,2-dioxaborolan-2-yl)-1,3,2-dioxaborolane (503 mg, 2.00 mmol), Pd(dppf)Cl$_2$ (145 mg, 0.200 mmol) and KOAc (389 mg, 4.00 mmol) in dioxane (40 mL) was degassed and purged with N$_2$ 3 times, the mixture was stirred at 100° C. for 2.5 hours under a N$_2$ atmosphere. The mixture was concentrated. The residue was purified by column chromatography on silica gel (petroleum ether/ethyl acetate=10:1) to give 3-methoxy-5-[[4-(4,4,5,5-tetramethyl-1,3,2-dioxaborolan-2-yl)phenyl]methyl]pyrazine-2-carbonitrile (300 mg).

Preparation of 5-[[4-(6-fluoro-2-pyridyl)phenyl]methyl]-3-methoxy-pyrazine-2-carbonitrile

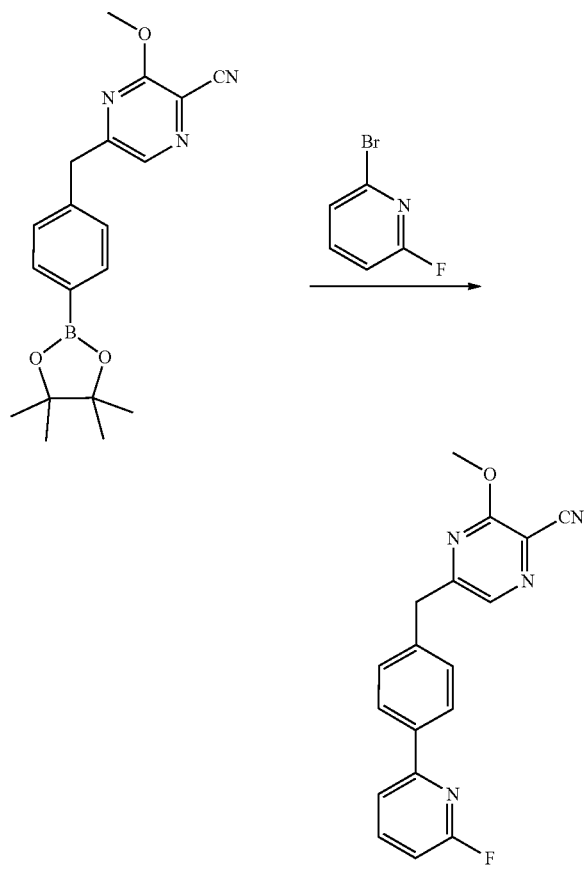

A mixture of 3-methoxy-5-[[4-(4,4,5,5-tetramethyl-1,3,2-dioxaborolan-2-yl)phenyl]methyl]pyrazine-2-carbonitrile (300 mg, 0.90 mmol), 2-bromo-6-fluoro-pyridine (301 mg, 1.70 mmol), Pd(dppf)Cl$_2$ (94 mg, 0.10 mmol), K$_2$CO$_3$ (236 mg, 1.70 mmol) in dioxane (30 mL) was degassed and purged with N$_2$ 3 times, and then the mixture was stirred at 50° C. for 24 hours under a N$_2$ atmosphere. The mixture was filtered and the residue was washed with ethyl acetate (10 mL×2), the combined organic layers were concentrated. The residue was purified by column chromatography on silica gel (petroleum ether/ethyl acetate=5:1) to give 5-[[4-(6-fluoro-2-pyridyl)phenyl]methyl]-3-methoxy-pyrazine-2-carbonitrile (200 mg).

Preparation of [5-[[4-(6-fluoro-2-pyridyl)phenyl]methyl]-3-methoxy-pyrazin-2-yl]methanamine

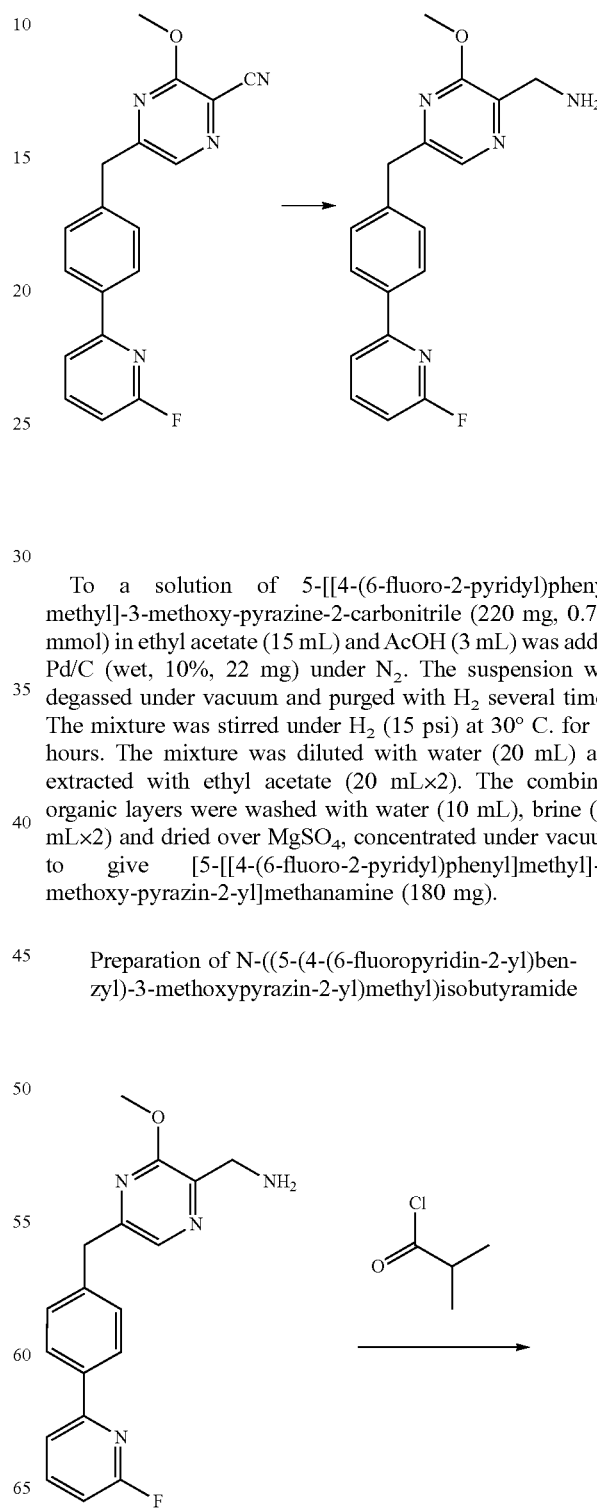

To a solution of 5-[[4-(6-fluoro-2-pyridyl)phenyl]methyl]-3-methoxy-pyrazine-2-carbonitrile (220 mg, 0.700 mmol) in ethyl acetate (15 mL) and AcOH (3 mL) was added Pd/C (wet, 10%, 22 mg) under N$_2$. The suspension was degassed under vacuum and purged with H$_2$ several times. The mixture was stirred under H$_2$ (15 psi) at 30° C. for 28 hours. The mixture was diluted with water (20 mL) and extracted with ethyl acetate (20 mL×2). The combined organic layers were washed with water (10 mL), brine (10 mL×2) and dried over MgSO$_4$, concentrated under vacuum to give [5-[[4-(6-fluoro-2-pyridyl)phenyl]methyl]-3-methoxy-pyrazin-2-yl]methanamine (180 mg).

Preparation of N-((5-(4-(6-fluoropyridin-2-yl)benzyl)-3-methoxypyrazin-2-yl)methyl)isobutyramide

51

-continued

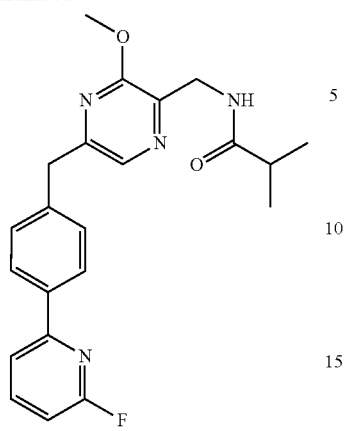

To a mixture of [5-[[4-(6-fluoro-2-pyridyl)phenyl] methyl]-3-methoxy-pyrazin-2-yl]methanamine (150 mg, 0.5 mmol) and 2-methylpropanoyl chloride (197 mg, 1.85 mmol) in THF (2 mL) was added triethylamine (468 mg, 4.6 mmol) under $N_2$. The mixture was stirred at 30° C. for 1 hour. The mixture was diluted with water (20 mL), extracted with ethyl acetate (20 mL×2). The combined organic layers were washed with water (10 mL), brine (10 mL×2) and dried over $MgSO_4$ and concentrated under vacuum. The residue was purified by silica gel chromatography (petroleum ether/ethyl acetate=3:1) to give N-((5-(4-(6-fluoropyridin-2-yl)benzyl)-3-methoxypyrazin-2-yl)methyl)isobutyramide (40 mg).

Preparation of 6-[[4-(6-fluoro-2-pyridyl)phenyl]methyl]-3-isopropyl-7H-imidazo[1,5-a]pyrazin-8-one

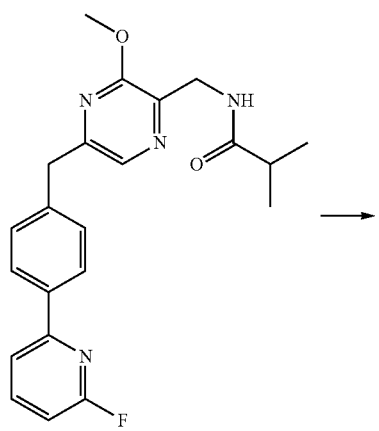

52

-continued

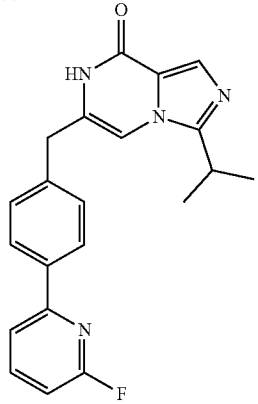

To a mixture of N-((5-(4-(6-fluoropyridin-2-yl)benzyl)-3-methoxypyrazin-2-yl)methyl)isobutyramide (30 mg, 0.08 mmol) in dioxane (3 mL) was added $POCl_3$ (23 mg, 0.15 mmol) under $N_2$. The mixture was stirred at 80° C. for 4 hours. The pH of the mixture was adjusted to pH=7~8 and diluted with water (20 mL) and extracted with ethyl acetate (20 mL×2). The combined organic layers were washed with water (10 mL), brine (10 mL×2) and dried over $MgSO_4$ and concentrated under vacuum to give 6-[[4-(6-fluoro-2-pyridyl)phenyl]methyl]-3-isopropyl-7H-imidazo[1,5-a]pyrazin-8-one (30 mg).

In a similar fashion the following compounds were prepared over two steps:

6-(4-(6-fluoropyridin-2-yl)benzyl)-3-propylimidazo[1,5-a]pyrazin-8(7H)-one from [5-[[4-(6-fluoro-2-pyridyl)phenyl]methyl]-3-methoxy-pyrazin-2-yl]methanamine and butanoyl chloride, 3-ethyl-6-(4-(6-fluoropyridin-2-yl)benzyl)imidazo[1,5-a]pyrazin-8(7H)-one from [5-[[4-(6-fluoro-2-pyridyl)phenyl]methyl]-3-methoxy-pyrazin-2-yl]methanamine and propanoyl chloride.

6-(4-(6-fluoropyridin-2-yl)benzyl)-3-(2,2,2-trifluoroethyl)imidazo[1,5-a]pyrazin-8(7H)-one from [5-[[4-(6-fluoro-2-pyridyl)phenyl]methyl]-3-methoxy-pyrazin-2-yl]methanamine and 3,3,3-trifluoropropanoyl chloride.

6-(4-(6-fluoropyridin-2-yl)benzyl)-3-(tetrahydrofuran-3-yl)imidazo[1,5-a]pyrazin-8(7H)-one from [5-[[4-(6-fluoro-2-pyridyl)phenyl]methyl]-3-methoxy-pyrazin-2-yl]methanamine, tetrahydrofuran-3-carboxylic acid and HATU.

6-(4-(6-fluoropyridin-2-yl)benzyl)-3-(2-methyltetrahydrofuran-3-yl)imidazo[1,5-a]pyrazin-8(7H)-one from [5-[[4-(6-fluoro-2-pyridyl)phenyl]methyl]-3-methoxy-pyrazin-2-yl]methanamine and 2-methyltetrahydrofuran-3-carbonyl chloride.

Preparation of 4-(trimethylstannyl)pyrimidine

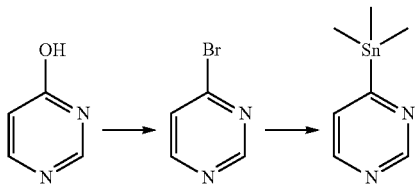

A mixture of pyrimidin-4-ol (1.0 g, 10.4 mmol) with $POBr_3$ (3.3 g, 11.5 mmol) was stirred at 100° C. for 4 hours.

Cooled to 30° C. and poured into ice-water (20 g), aqueous NaHCO$_3$ was added until pH=7 and extracted with dichloromethane (15 mL×3). The combined organic phases were washed with water, dried over Na$_2$SO$_4$, filtered and concentrated under vacuum to afford 4-bromopyrimidine (700 mg). $^1$H NMR (CDCl$_3$, 400 MHz): δ 8.97 (s, 1H), 8.52 (d, J=5.2 Hz, 1H), 7.57 (d, J=5.6 Hz, 1H).

A solution of 4-bromopyrimidine (500 mg, 3.2 mmol), 1,1,1,2,2,2-hexamethyldistannane (1.9 g, 5.80 mmol) and Pd(PPh$_3$)$_4$ (364 mg, 0.32 mmol) in dioxane (10 mL), was stirred at 110° C. for 1 hour. Celite was added and the mixture was concentrated to dryness under reduced pressure. The residue was purified by column chromatography (Al$_2$O$_3$, petroleum ether/ethyl acetate=1:0 to 0:1) to afford 4-(trimethylstannyl)pyrimidine (400 mg). $^1$H NMR (CDCl$_3$, 400 MHz): δ 9.25 (s, 1H), 8.51 (d, J=4.8 Hz, 1H), 7.49 (d, J=4.8 Hz, 1H), 0.39 (s, 9H).

COMPOUNDS OF THE INVENTION

Example 1

5-methyl-6-[[4-(6-methyl-2-pyridyl)phenyl]methyl]-1-tetrahydropyran-4-yl-pyrazolo[4,3-c]pyridin-4-one

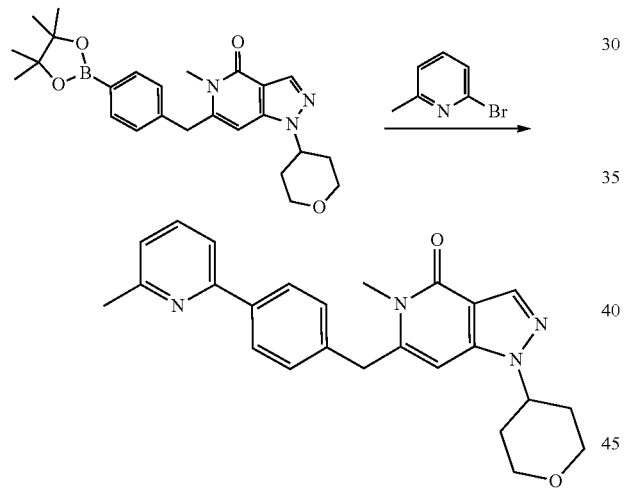

A mixture of 5-methyl-1-(tetrahydro-2H-pyran-4-yl)-6-(4-(4,4,5,5-tetramethyl-1,3,2-dioxaborolan-2-yl)benzyl)-1H-pyrazolo[4,3-c]pyridin-4(5H)-one (55 mg, 0.12 mmol), 2-bromo-6-methyl-pyridine (31 mg, 0.18 mmol), Pd(dppf)Cl$_2$ (9 mg, 0.012 mmol), Cs$_2$CO$_3$ (80 mg, 0.24 mmol) and water (1 mL) in dioxane (2 mL) was stirred at 100° C. for 3 hours. The mixture was concentrated under vacuum. The residue was purified was purified by preparative-TLC (petroleum ether/ethyl acetate=0:1) to give 5-methyl-6-[[4-(6-methyl-2-pyridyl)phenyl]methyl]-1-tetrahydropyran-4-yl-pyrazolo[4,3-c]pyridin-4-one. $^1$H NMR (CDCl$_3$ 400 MHz): δ 8.18 (s, 1H), 7.98 (d, J=8.4 Hz, 2H), 7.66 (q, J=8.0 Hz, 1H), 7.51 (d, J=7.6 Hz, 1H), 7.29-7.27 (m, 2H), 7.13 (d, J=7.6 Hz, 1H), 6.25 (s, 1H), 4.42-4.36 (m, 1H), 4.17-4.12 (m, 4H), 3.61-3.55 (m, 2H), 3.49 (s, 3H), 2.64 (s, 3H), 2.39-2.32 (m, 2H), 1.95-1.91 (m, 2H). LC-MS: t$_R$=1.715 min (Method C), m/z=415.1 [M+H]$^+$.

The following compounds were prepared in a manner similar to example 1:

Example 2

5-methyl-6-[[4-(2-pyridyl)phenyl]methyl]-1-tetrahydropyran-4-yl-pyrazolo[3,4-d]pyrimidin-4-one

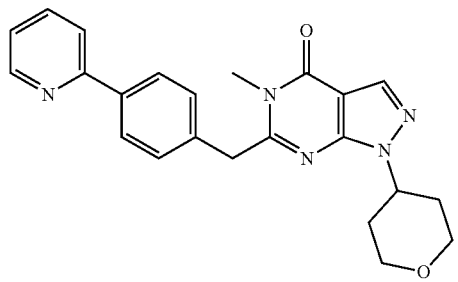 [SMILES: Cn1c(Cc2ccc(-c3ccccn3)cc2)nc2c(cnn2C2CCOCC2)c1=O]

From 5-methyl-1-(tetrahydro-2H-pyran-4-yl)-6-(4-(4,4,5,5-tetramethyl-1,3,2-dioxaborolan-2-yl)benzyl)-1,5-dihydro-4H-pyrazolo[3,4-d]pyrimidin-4-one and 2-bromopyridine. $^1$H NMR (CDCl$_3$ 400 MHz): δ 8.71-8.69 (m, 1H), 8.09 (s, 1H), 7.98 (d, J=8.4 Hz, 2H), 7.79-7.70 (m, 2H), 7.33 (d, J=8.4 Hz, 2H), 7.23-7.25 (m, 1H), 4.91-4.85 (m, 1H), 4.30 (s, 2H), 4.17-4.14 (m, 2H), 3.66-3.59 (m, 2H), 3.50 (s, 3H), 2.44-2.37 (m, 2H), 1.99-1.96 (m, 2H). LC-MS: t$_R$=1.746 min (Method C), m/z=402.0 [M+H]$^+$.

Example 3

5-methyl-6-[[4-(6-methyl-2-pyridyl)phenyl]methyl]-1-tetrahydropyran-4-yl-pyrazolo[3,4-d]pyrimidin-4-one

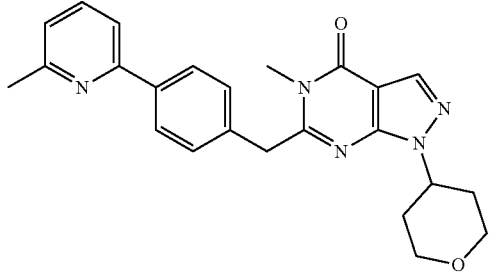 [SMILES: Cc1cccc(-c2ccc(Cc3nc4c(cnn4C4CCOCC4)c(=O)n3C)cc2)n1]

From 5-methyl-1-(tetrahydro-2H-pyran-4-yl)-6-(4-(4,4,5,5-tetramethyl-1,3,2-dioxaborolan-2-yl)benzyl)-1,5-dihydro-4H-pyrazolo[3,4-d]pyrimidin-4-one and 2-bromo-6-methyl-pyridine. $^1$H NMR (CDCl$_3$ 400 MHz): δ 8.09 (s, 1H), 7.97 (d, J=8.4 Hz, 2H), 7.65 (t, J=8.0 Hz, 1H), 7.50 (d, J=8.0 Hz, 1H), 7.31 (d, J=8.0 Hz, 2H), 7.12 (d, J=8.0 Hz, 1H), 4.91-4.85 (m, 1H), 4.29 (s, 2H), 4.17-4.15 (m, 2H), 3.63 (t, J=11.6 Hz, 2H), 3.49 (s, 3H), 2.63 (s, 3H), 2.46-2.37 (m, 2H), 1.99-1.96 (m, 2H). LC-MS: t$_R$=1.717 min (Method C), m/z=416.1 [M+H]$^+$.

Example 4

6-[[4-(6-fluoro-2-pyridyl)phenyl]methyl]-5-methyl-1-tetrahydropyran-4-yl-pyrazolo[3,4-d]pyrimidin-4-one

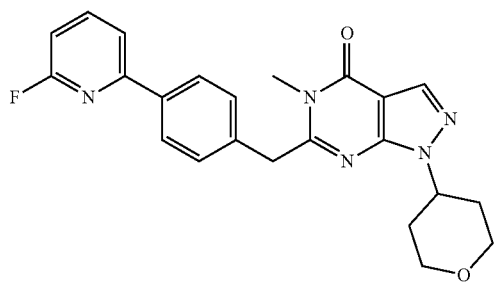 [SMILES: Cn1c(Cc2ccc(-c3cccc(F)n3)cc2)nc2c(cnn2C2CCOCC2)c1=O]

From 5-methyl-1-(tetrahydro-2H-pyran-4-yl)-6-(4-(4,4,5,5-tetramethyl-1,3,2-dioxaborolan-2-yl)benzyl)-1,5-dihydro-4H-pyrazolo[3,4-d]pyrimidin-4-one and 2-bromo-6-fluoropyridine. $^1$H NMR (CDCl$_3$ 400 MHz): δ 8.08 (s, 1H), 7.99 (d, J=8.4 Hz, 2H), 7.89-7.83 (m, 1H), 7.62-7.60 (m, 1H), 7.33 (d, J=8.0 Hz, 2H), 6.89-6.74 (m, 1H), 4.90-4.84 (m, 1H), 4.29 (s, 2H), 4.16-4.13 (m, 2H), 3.62 (t, J=12.0 Hz, 2H), 3.49 (s, 3H), 2.45-2.36 (m, 2H), 1.98-1.95 (m, 2H). LC-MS: $t_R$=2.610 min (Method C), m/z=420.0 [M+H]$^+$.

Example 5

6-[[4-(6-fluoro-2-pyridyl)phenyl]methyl]-5-methyl-1-tetrahydropyran-4-yl-pyrazolo[4,3-c]pyridin-4-one

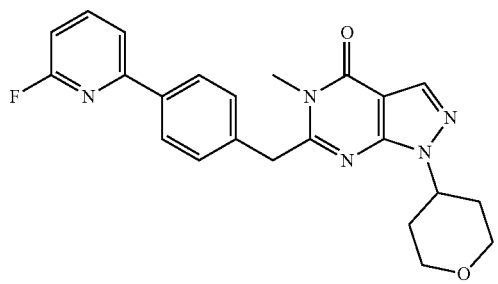 [SMILES: Cn1c(Cc2ccc(-c3cccc(F)n3)cc2)nc2c(cnn2C2CCOCC2)c1=O]

From 5-methyl-1-(tetrahydro-2H-pyran-4-yl)-6-(4-(4,4,5,5-tetramethyl-1,3,2-dioxaborolan-2-yl)benzyl)-1H-pyrazolo[4,3-c]pyridin-4(5H)-one and 2-bromo-6-fluoropyridine. $^1$H NMR (CDCl$_3$ 400 MHz): δ 8.18 (s, 1H), 7.99 (d, J=8.4 Hz, 2H), 7.89 (q, J=8.0 Hz, 1H), 7.61 (dd, J=2.4, 7.6 Hz, 1H), 7.29-7.27 (m, 2H), 6.89 (dd, J=3.2, 8.4 Hz, 1H), 6.28 (s, 1H), 4.43-4.35 (m, 1H), 4.17-4.12 (m, 4H), 3.56 (t, J=12.0 Hz, 2H), 3.47 (s, 3H), 2.41-2.32 (m, 2H), 1.95-1.92 (m, 2H). LC-MS: $t_R$=2.614 min (Method C), m/z=419.0 [M+H]$^+$.

Example 6

5-methyl-6-[[4-(2-pyridyl)phenyl]methyl]-1-tetrahydropyran-4-yl-pyrazolo[4,3-c]pyridin-4-one

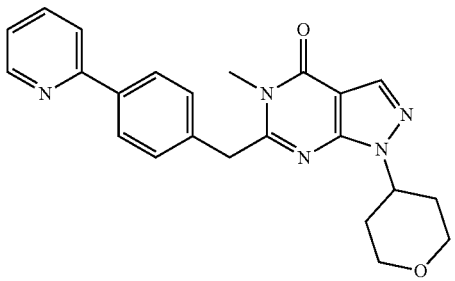 [SMILES: Cn1c(Cc2ccc(-c3ccccn3)cc2)nc2c(cnn2C2CCOCC2)c1=O]

From 5-methyl-1-(tetrahydro-2H-pyran-4-yl)-6-(4-(4,4,5,5-tetramethyl-1,3,2-dioxaborolan-2-yl)benzyl)-1H-pyrazolo[4,3-c]pyridin-4(5H)-one and 2-bromo-pyridine. $^1$H NMR (CDCl$_3$ 400 MHz): δ 8.72-8.70 (m, 1H), 8.18 (s, 1H), 8.01-7.98 (m, 2H), 7.78-7.74 (m, 2H), 7.29 (d, J=8.4 Hz, 2H), 7.27-7.24 (m, 1H), 6.27 (s, 1H), 4.42-4.36 (m, 1H), 4.17-4.13 (m, 4H), 3.57 (dt, J=2.0, 12.0 Hz, 2H), 3.49 (s, 3H), 2.40-2.35 (m, 2H), 1.96-1.92 (m, 2H). LC-MS: $t_R$=1.777 min (Method C), m/z=401.0 [M+H]$^+$.

Example 7

7-[(4-methoxyphenyl)methyl]-6-[[4-(2-pyridyl)piperazin-1-yl]methyl]-3-tetrahydropyran-4-yl-imidazo[1,5-a]pyrazin-8-one

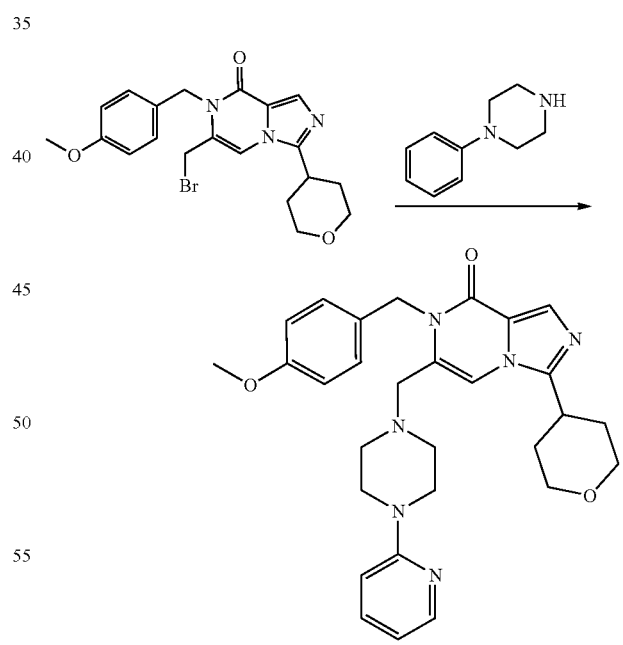

6-(Bromomethyl)-7-(4-methoxybenzyl)-3-(tetrahydro-2H-pyran-4-yl)imidazo[1,5-a]pyrazin-8(7H)-one (52 mg, 0.091 mmol) and 1-(pyridin-2-yl)piperazine (60.4 mg, 0.054 mL, 0.370 mmol) were dissolved in DMF (2.5 mL) and N,N-diisopropylethylamine (0.08 mL, 0.458 mmol) was added. The reaction mixture was heated under microwave conditions for 15 min at 100° C. 7-[(4-methoxyphenyl)methyl]-6-[[4-(2-pyridyl)piperazin-1-yl]methyl]-3-tetrahydropyran-4-yl-imidazo[1,5-a]pyrazin-8-one was isolated after purification by preperative HPLC. $^1$H NMR (CDCl$_3$ 500 MHz): δ 8.21 (m, 1H), 7.95 (d, J=1.8 Hz, 1H), 7.51 (t, J=7.9 Hz, 1H), 7.16 (m, 2H), 6.86 (m, 3H), 6.66 (m, 2H), 5.54 (s, 2H), 4.15 (m, 2H), 3.79 (d, J=1.8 Hz, 3H), 3.61 (m, 6H), 3.25 (s, 2H), 3.07 (m, 1H), 2.60 (t, J=4.9 Hz, 4H), 2.17 (m, 2H), 1.86 (m, 2H). LC-MS: t$_R$=0.51 min (Method A), m/z=515.2 [M+H]$^+$.

The following compound was prepared in a manner similar to example 7:

Example 8

7-[(4-methoxyphenyl)methyl]-6-[(4-phenylpiperazin-1-yl)methyl]-3-tetrahydropyran-4-yl-imidazo[1,5-a]pyrazin-8-one

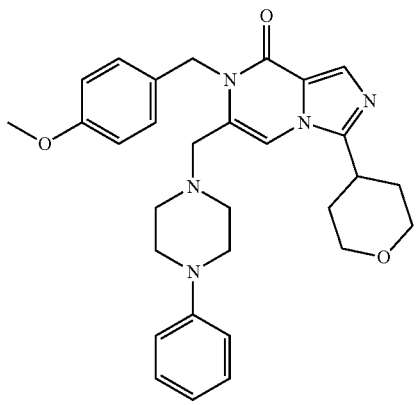 [SMILES: COc1ccc(Cn2c(CN3CCN(c4ccccc4)CC3)cn3c(C4CCOCC4)ncc3c2=O)cc1]

From 6-(bromomethyl)-7-(4-methoxybenzyl)-3-(tetrahydro-2H-pyran-4-yl)imidazo[1,5-a]pyrazin-8(7H)-one and 1-(phenyl)piperazine. $^1$H NMR (CDCl$_3$ 500 MHz): δ 7.96 (d, J=1.9 Hz, 1H), 7.31 (m, 2H), 7.17 (m, 2H), 6.96 (m, 2H), 6.91 (m, 1H), 6.86 (m, 3H), 5.54 (s, 2H), 4.12 (m, 2H), 3.80 (d, J=2.0 Hz, 3H), 3.62 (dd, J=12.9, 10.8 Hz, 2H), 3.25 (dd, J=10.4, 5.9 Hz, 6H), 3.12 (m, 1H), 2.66 (q, J=4.7, 3.5 Hz, 4H), 2.17 (m, 2H), 1.91 (d, J=13.9 Hz, 2H). LC-MS: t$_R$=0.63 min (Method A), m/z=514.2 [M+H]$^+$.

Example 9

7-[(4-methoxyphenyl)methyl]-6-[[4-(2-pyridyl)phenyl]methyl]-3-tetrahydropyran-4-yl-imidazo[1,5-a]pyrazin-8-one

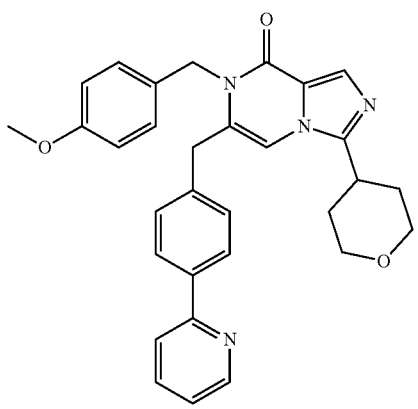 [SMILES: COc1ccc(Cn2c(Cc3ccc(-c4ccccn4)cc3)cn3c(C4CCOCC4)ncc3c2=O)cc1]

Six identical reactions were run in parallel: A mixture of 6-(bromomethyl)-7-(4-methoxybenzyl)-3-(tetrahydro-2H-pyran-4-yl)imidazo[1,5-a]pyrazin-8(7H)-one (500 mg, 1.16 mmol), 2-(4-(4,4,5,5-tetramethyl-1,3,2-dioxaborolan-2-yl)phenyl)pyridine (489 mg, 1.74 mmol), K$_2$CO$_3$ (321 mg, 2.32 mmol), Pd(dppf)Cl$_2$ (170 mg, 0.23 mmol) in dioxane (40 mL) and water (1.50 mL) were degassed and purged with N$_2$ 3 times, then the mixture was stirred at 100° C. for 12 hours under an atmosphere of N$_2$. The six reaction mixtures were combined and concentrated under reduced pressure to remove dioxane and water. The residue was purified by preparative-TLC on silica gel (ethyl acetate) followed by preparative-HPLC to give 7-[(4-methoxyphenyl)methyl]-6-[[4-(2-pyridyl)phenyl]methyl]-3-tetrahydropyran-4-yl-imidazo[1,5-a]pyrazin-8-one. $^1$H NMR (CDCl$_3$ 400 MHz): δ 8.71 (d, J=4.8 Hz, 1H), 8.01 (d, J=8.0 Hz, 2H), 7.97 (s, 1H), 7.81-7.23 (m, 2H), 7.29 (s, 2H), 7.27 (s, 1H), 7.11 (d, J=8.4 Hz, 2H), 6.87 (d, J=8.4 Hz, 2H), 6.76 (s, 1H), 5.03 (s, 2H), 4.12-4.10 (m, 2H), 3.84 (s, 2H), 3.80 (s, 3H), 3.55 (t, J=10.0 Hz, 2H), 3.10-3.04 (m, 1H), 2.19-2.09 (m, 2H), 1.90-1.87 (m, 2H). LC-MS: t$_R$=0.49 min (Method A), m/z=507.1 [M+H]$^+$.

Example 10

6-[[4-(2-pyridyl)phenyl]methyl]-3-tetrahydropyran-4-yl-7H-imidazo[1,5-a]pyrazin-8-one

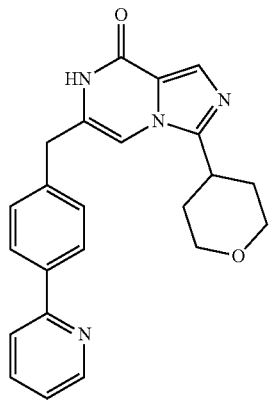 [SMILES: O=c1[nH]c(Cc2ccc(-c3ccccn3)cc2)cn2c(C3CCOCC3)ncc12]

7-[(4-methoxyphenyl)methyl]-6-[[4-(2-pyridyl)phenyl]methyl]-3-tetrahydropyran-4-yl-imidazo[1,5-a]pyrazin-8-one (200 mg, 0.39 mmol) was added to trifluoroacetic acid (15 mL). The mixture was stirred at 100° C. for 6 days. The reaction mixture was concentrated under reduced pressure. The residue was purified by preparative-HPLC to give 6-[[4-(2-pyridyl)phenyl]methyl]-3-tetrahydropyran-4-yl-7H-imidazo[1,5-a]pyrazin-8-one. $^1$H NMR (CDCl$_3$ 400 MHz): δ 8.77 (s, 1H), 8.71-8.70 (m, 1H), 7.99 (d, J=8.0 Hz, 2H), 7.91 (s, 1H), 7.80-7.71 (m, 2H), 7.41 (d, J=8.4 Hz, 2H), 7.27-7.25 (m, 1H), 6.76 (s, 1H), 4.13-4.11 (m, 2H), 3.84 (s, 2H), 3.59-3.56 (m, 2H), 3.11-3.06 (m, 1H), 2.18-2.07 (m, 2H), 1.89-1.86 (m, 2H). LC-MS: t$_R$=1.784 min (Method B), m/z=387.1 [M+H]$^+$.

Example 11

7-methyl-6-[[4-(2-pyridyl)phenyl]methyl]-3-tetrahydropyran-4-yl-imidazo[1,5-a]pyrazin-8-one

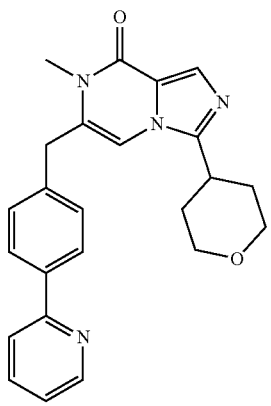 [SMILES: Cn1c(Cc2ccc(-c3ccccn3)cc2)cn2c(C3CCOCC3)ncc2c1=O]

To a solution of 6-[[4-(2-pyridyl)phenyl]methyl]-3-tetrahydropyran-4-yl-7H-imidazo[1,5-a]pyrazin-8-one (67 mg, 0.17 mmol) and CH$_3$I (0.022 mL, 0.35 mmol) in MeCN (3 mL) was added Cs$_2$CO$_3$ (113 mg, 0.35 mmol). The mixture was stirred at room temperature for 16 hours. The reaction mixture was concentrated under reduced pressure to remove MeCN. The residue was purified by column chromatography on silica gel (methanol/dichloromethane=0≈2%) to give 7-methyl-6-[[4-(2-pyridyl)phenyl]methyl]-3-tetrahydropyran-4-yl-imidazo[1,5-a]pyrazin-8-one. $^1$H NMR (CDCl$_3$ 400 MHz): δ 8.71 (d, J=4.4 Hz, 1H), 8.01 (d, J=8.0 Hz, 2H), 7.91 (s, 1H), 7.80-7.72 (m, 2H), 7.34 (d, J=8.4 Hz, 2H), 7.29-7.27 (m, 1H), 6.80 (s, 1H), 4.11 (d, J=11.6 Hz, 2H), 3.98 (s, 2H), 3.55 (t, J=5.8 Hz, 2H), 3.34 (s, 3H), 3.11-3.05 (m, 1H), 2.18-2.08 (m, 2H), 1.90-1.87 (m, 2H). LC-MS: $t_R$=1.536 min (Method C), m/z=401.2 [M+H]$^+$.

The following compound was prepared in a manner similar to example 11:

Example 12

7-ethyl-6-[[4-(2-pyridyl)phenyl]methyl]-3-tetrahydropyran-4-yl-imidazo[1,5-a]pyrazin-8-one

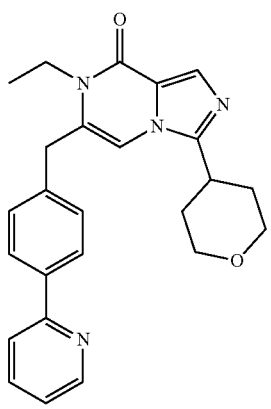 [SMILES: CCn1c(Cc2ccc(-c3ccccn3)cc2)cn2c(C3CCOCC3)ncc2c1=O]

From 6-[[4-(2-pyridyl)phenyl]methyl]-3-tetrahydropyran-4-yl-7H-imidazo[1,5-a]pyrazin-8-one and ethyliodide. $^1$H NMR (CDCl$_3$ 400 MHz): δ 8.68 (d, J=4.0 Hz, 1H), 7.99 (d, J=8.0 Hz, 2H), 7.88 (s, 1H), 7.78-7.71 (m, 2H), 7.32 (d, J=8.0 Hz, 2H), 7.25-7.23 (m, 1H), 6.73 (s, 1H), 4.09 (d, J=11.6 Hz, 2H), 3.95 (s, 2H), 3.87 (q, J=7.2 Hz, 2H), 3.54 (t, J=12.0 Hz, 2H), 3.04 (t, J=11.2 Hz, 1H), 2.14-2.06 (m, 2H), 1.87-1.84 (m, 2H), 1.16 (t, J=9.8 Hz, 3H). LC-MS: $t_R$=1.643 min (Method C), m/z=415.2 [M+H]$^+$.

The following compounds were prepared in a manner similar to example 9:

Example 13

7-methyl-6-[[4-(6-methyl-2-pyridyl)phenyl]methyl]-3-tetrahydropyran-4-yl-imidazo[1,5-a]pyrazin-8-one

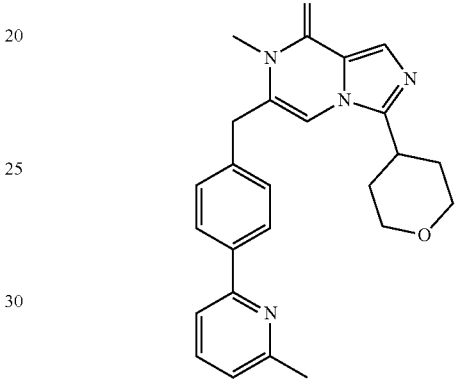

From 6-(bromomethyl)-7-(4-methoxybenzyl)-3-(tetrahydro-2H-pyran-4-yl)imidazo[1,5-a]pyrazin-8(7H)-one and 2-methyl-6-(4-(4,4,5,5-tetramethyl-1,3,2-dioxaborolan-2-yl)phenyl)pyridine TFA salt. $^1$H NMR (DMSO-d$_6$ 600 MHz): δ 8.09-8.05 (m, 3H), 7.93 (brs, 2H), 7.82 (s, 1H), 7.46 (d, J=8.0 Hz, 2H), 7.13 (brs, 1H), 4.11 (s, 2H), 3.99 (dt, J=11.5, 3.3 Hz, 2H), 3.55-3.42 (m, 3H), 3.18 (s, 3H), 2.55 (s, 3H), 1.90-1.82 (m, 4H). LC-MS: $t_R$=0.33 min (Method A), m/z=415.1 [M+H]$^+$.

Example 14

6-[[4-(6-fluoro-2-pyridyl)phenyl]methyl]-7-methyl-3-tetrahydropyran-4-yl-imidazo[1,5-a]pyrazin-8-one

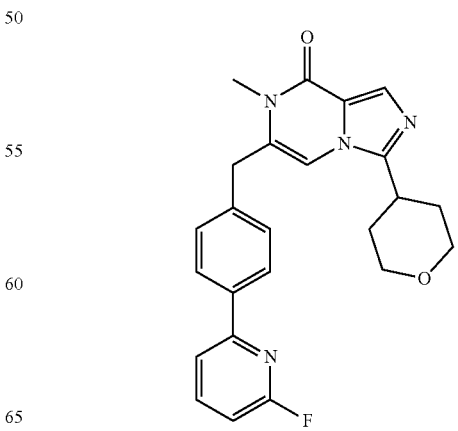

From 6-(bromomethyl)-7-(4-methoxybenzyl)-3-(tetrahydro-2H-pyran-4-yl)imidazo[1,5-a]pyrazin-8(7H)-one and 2-fluoro-6-(4-(4,4,5,5-tetramethyl-1,3,2-dioxaborolan-2-yl)phenyl)pyridine TFA salt. $^1$H NMR (DMSO-$d_6$ 600 MHz): δ 8.1-8.00 (m, 4H), 7.95-7.91 (m, 1H), 7.85-7.80 (s, 1H), 7.49-7.44 (m, 2H), 7.37 (d, J=7.6 Hz, 1H), 6.35 (brs, 1H), 4.11 (s, 1H), 3.99 (dt, J=11.5, 3.3 Hz, 2H), 3.55-3.42 (m, 3H), 3.18 (s, 3H), 1.88-1.82 (m, 4H). LC-MS: $t_R$=0.56 min (Method A), m/z=419.0 [M+H]$^+$.

Example 15

6-[[4-[6-(difluoromethyl)-2-pyridyl]phenyl]methyl]-7-methyl-3-tetrahydropyran-4-yl-imidazo[1,5-a]pyrazin-8-one

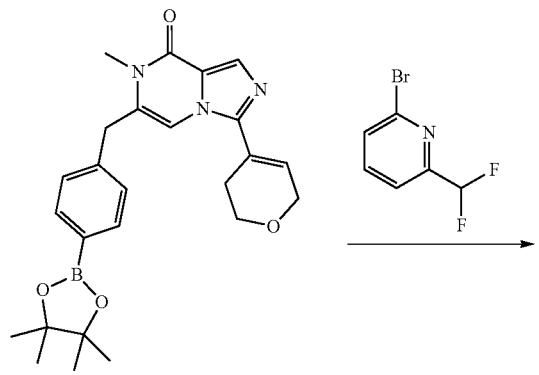

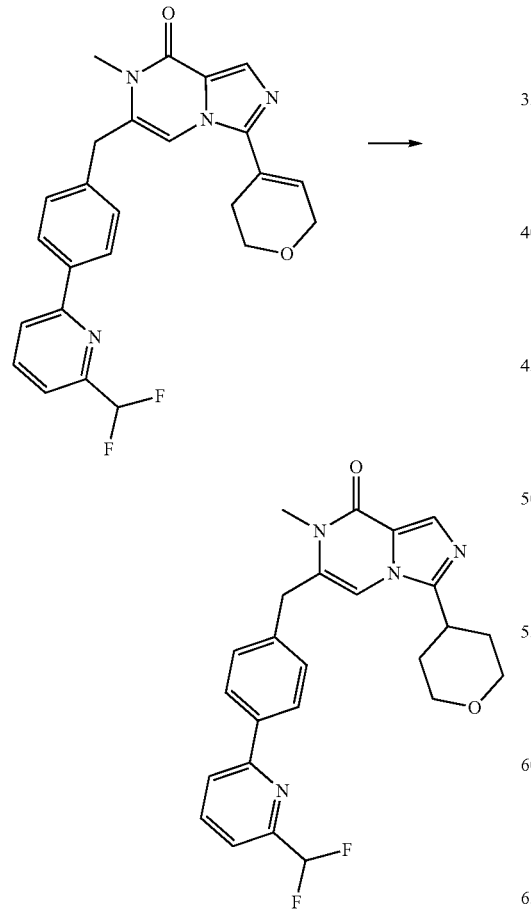

A mixture of 3-(3,6-dihydro-2H-pyran-4-yl)-7-methyl-6-(4-(4,4,5,5-tetramethyl-1,3,2-dioxaborolan-2-yl)benzyl)imidazo[1,5-a]pyrazin-8(7H)-one (67 mg, 0.15 mmol), $Cs_2CO_3$ (146 mg, 0.45 mmol), Pd(dppf)Cl$_2$ (5.48 mg, 0.007 mmol), 2-bromo-6-(difluoromethyl)pyridine (31 mg, 0.15 mmol) in dioxane (1 mL), water (0.4 mL) under a $N_2$ atmosphere was stirred at 100° C. for 4 hours. The mixture was concentrated and the residue was extracted with ethyl acetate (20 mL). The organic phase was dried over $Na_2SO_4$ and concentrated. The residue was purified by preparative TLC on silica gel (ethyl acetate) to give 6-(4-(6-(difluoromethyl)pyridin-2-yl)benzyl)-3-(3,6-dihydro-2H-pyran-4-yl)-7-methylimidazo[1,5-a]pyrazin-8(7H)-one (36 mg). A mixture of 6-(4-(6-(difluoromethyl)pyridin-2-yl)benzyl)-3-(3,6-dihydro-2H-pyran-4-yl)-7-methylimidazo[1,5-a]pyrazin-8(7H)-one (36 mg, 0.08 mol), Pd/C (10%, 8 mg) in methanol (1 mL) under a $H_2$ atmosphere (15 psi) was stirred at room temperature for 5 hours. The mixture was filtered, and concentrated. The residue was purified by preparative HPLC to give 6-[[4-[6-(difluoromethyl)-2-pyridyl]phenyl]methyl]-7-methyl-3-tetrahydropyran-4-yl-imidazo[1,5-a]pyrazin-8-one. $^1$H NMR (CDCl$_3$ 400 MHz): δ 8.05 (d, J=8.3 Hz, 2H), 7.96-7.89 (m, 2H), 7.87-7.81 (m, 1H), 7.62 (d, J=7.5 Hz, 1H), 7.35 (d, J=8.3 Hz, 2H), 6.82 (s, 1H), 6.71 (t, J=55.2 Hz, 1H), 4.17-4.06 (m, 2H), 3.99 (s, 2H), 3.57 (dt, J=2.4, 12 Hz, 2H), 3.33 (s, 3H), 3.16-3.01 (m, 1H), 2.22-2.01 (m, 2H), 1.91-1.87 (m, 2H). LC-MS: $t_R$=2.415 min (Method C), m/z=451.0 [M+H]$^+$.

The following compounds were prepared in a manner similar to example 15:

Example 16

6-[[4-(6-methoxy-2-pyridyl)phenyl]methyl]-7-methyl-3-tetrahydropyran-4-yl-imidazo[1,5-a]pyrazin-8-one

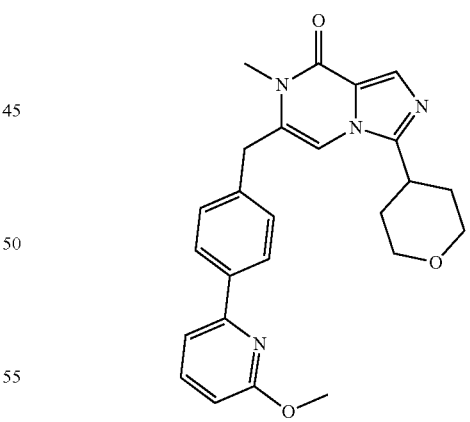

From 3-(3,6-dihydro-2H-pyran-4-yl)-7-methyl-6-(4-(4,4,5,5-tetramethyl-1,3,2-dioxaborolan-2-yl)benzyl)imidazo[1,5-a]pyrazin-8(7H)-one and 2-bromo-6-methoxy-pyridine. $^1$H NMR (CDCl$_3$ 400 MHz): δ 8.07-8.05 (m, 2H), 7.91 (s, 1H), 7.67-7.63 (m, 1H), 7.35-7.30 (m, 3H), 6.82 (s, 1H), 6.72 (d, J=4.8 Hz, 1H), 4.13-4.10 (m, 2H), 4.04 (s, 3H), 3.97 (s, 2H) 3.60-3.54 (m, 2H), 3.33 (s, 3H), 3.12-3.06 (m, 1H), 2.17-2.09 (m, 2H), 1.90-1.87 (m, 2H). LC-MS: $t_R$=2.403 min (Method C), m/z=431.1 [M+H]$^+$.

Example 17

6-[[4-(3-methoxy-2-pyridyl)phenyl]methyl]-7-methyl-3-tetrahydropyran-4-yl-imidazo[1,5-a]pyrazin-8-one

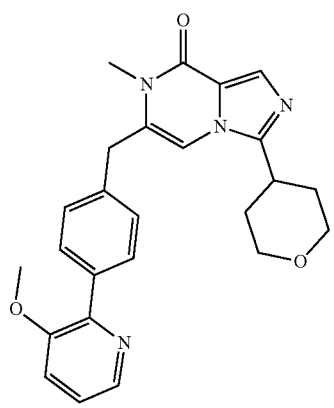 [SMILES: COc1cccnc1-c1ccc(Cc2cn3c(C4CCOCC4)ncc3c(=O)n2C)cc1]

From 3-(3,6-dihydro-2H-pyran-4-yl)-7-methyl-6-(4-(4,4,5,5-tetramethyl-1,3,2-dioxaborolan-2-yl)benzyl)imidazo[1,5-a]pyrazin-8(7H)-one and 2-bromo-3-methoxypyridine. $^1$H NMR (CDCl$_3$ 400 MHz): δ 8.32 (d, J=1.2, 4.4 Hz, 1H), 7.93 (d, J=8.4 Hz, 2H), 7.90 (s, 1H), 7.33-7.28 (m, 4H), 6.80 (s, 1H), 4.11-4.10 (m, 2H), 3.97 (s, 2H), 3.89 (s, 3H), 3.60-3.55 (m, 2H), 3.35 (s, 3H), 3.11-3.05 (m, 1H), 2.18-2.07 (m, 2H), 1.90-1.86 (m, 2H). LC-MS: $t_R$=1.84 min (Method C), m/z=431.0 [M+H]$^+$.

Example 18

7-methyl-6-[[4-(o-tolyl)phenyl]methyl]-3-tetrahydropyran-4-yl-imidazo[1,5-a]pyrazin-8-one

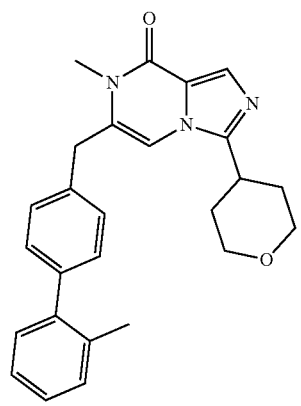 [SMILES: Cc1ccccc1-c1ccc(Cc2cn3c(C4CCOCC4)ncc3c(=O)n2C)cc1]

From 3-(3,6-dihydro-2H-pyran-4-yl)-7-methyl-6-(4-(4,4,5,5-tetramethyl-1,3,2-dioxaborolan-2-yl)benzyl)imidazo[1,5-a]pyrazin-8(7H)-one and 1-bromo-2-methyl-benzene. $^1$H NMR (CDCl$_3$ 400 MHz): δ 7.90 (s, 1H), 7.35-7.33 (m, 2H), 7.29-7.28 (m, 4H), 7.24-7.21 (m, 2H), 6.76 (s, 1H), 4.13-4.11 (m, 2H), 3.97 (s, 2H), 3.58-3.56 (m, 2H), 3.38 (s, 3H), 3.09-2.02 (m, 1H), 2.27 (s, 3H), 2.13-2.10 (m, 2H), 1.90-1.86 (m, 2H). LC-MS: $t_R$=2.407 min (Method D), m/z=414.0 [M+H]$^+$.

Example 19

7-methyl-6-[(4-phenylphenyl)methyl]-3-tetrahydropyran-4-yl-imidazo[1,5-a]pyrazin-8-one

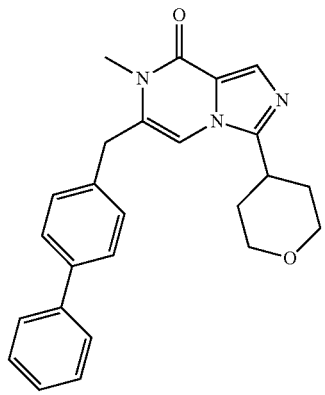 [SMILES: Cn1c(Cc2ccc(-c3ccccc3)cc2)cn2c(C3CCOCC3)ncc2c1=O]

From 6-(4-bromobenzyl)-3-(3,6-dihydro-2H-pyran-4-yl)-7-methylimidazo[1,5-a]pyrazin-8(7H)-one and phenylboronic acid. $^1$H NMR (CDCl$_3$ 400 M Hz): δ 7.91 (s, 1H), 7.61-7.58 (m, 4H), 7.48-7.45 (m, 2H), 7.40-7.30 (m, 1H), 7.30-7.28 (m, 2H), 6.80 (s, 1H), 4.14-4.11 (m, 2H), 3.96 (s, 2H), 3.56 (dt, J=2.0, 11.6 Hz, 2H), 3.35 (s, 3H), 3.11-3.04 (m, 1H), 2.15-2.11 (m, 2H), 1.91-1.87 (m, 2H). LC-MS: $t_R$=2.233 min (Method D), m/z=400.1 [M+H]$^+$.

Example 20

7-methyl-6-(4-(1-methyl-1H-imidazol-4-yl)benzyl)-3-(tetrahydro-2H-pyran-4-yl)imidazo[1,5-a]pyrazin-8(7H)-one

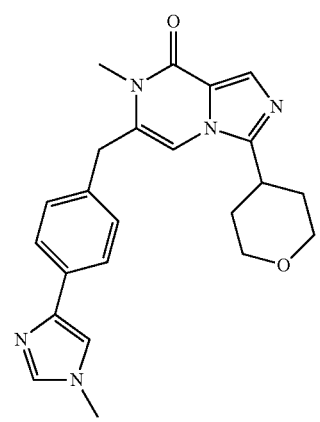 [SMILES: Cn1cnc(-c2ccc(Cc3cn4c(C5CCOCC5)ncc4c(=O)n3C)cc2)c1]

From 3-(3,6-dihydro-2H-pyran-4-yl)-7-methyl-6-(4-(4,4,5,5-tetramethyl-1,3,2-dioxaborolan-2-yl)benzyl)imidazo[1,5-a]pyrazin-8(7H)-one and 4-bromo-1-methyl-1H-imidazole. $^1$H NMR (CDCl$_3$ 400 M Hz): δ 7.89 (s, 1H), 7.76 (d, J=8.4 Hz, 2H), 7.50 (s, 1H), 7.23-7.20 (m, 3H), 6.75 (s, 1H), 4.12-4.10 (m, 2H), 3.91 (s, 2H), 3.75 (s, 3H), 3.59-2.53 (m, 2H), 3.34 (s, 3H), 3.10-2.02 (m, 1H), 2.17-2.06 (m, 2H), 1.90-1.84 (m, 2H). LC-MS: $t_R$=1.565 min (Method C), m/z=404.0 [M+H]$^+$.

Example 21

6-[[4-(6-fluoro-2-pyridyl)phenyl]methyl]-3-isopropyl-7-methyl-imidazo[1,5-a]pyrazin-8-one

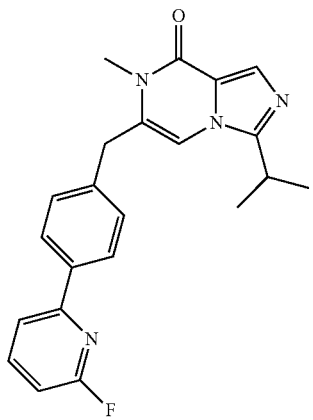 [SMILES: CC(C)c1ncc2c(=O)n(C)c(Cc3ccc(-c4cccc(F)n4)cc3)cn12]

To a mixture of 6-[[4-(6-fluoro-2-pyridyl)phenyl]methyl]-3-isopropyl-7H-imidazo[1,5-a]pyrazin-8-one (25 mg, 0.07 mmol) and MeI (20 mg, 0.14 mmol) in THF (5 mL) was added $K_2CO_3$ (19 mg, 0.14 mmol) under $N_2$. The mixture was stirred at 50° C. for 14 hours. The mixture was filtrated and washed by ethyl acetate and concentrated in vacuo. The residue was purified by preparative HPLC to give 6-(4-(6-fluoropyridin-2-yl)benzyl)-3-isopropyl-7-methylimidazo[1,5-a]pyrazin-8(7H)-one. $^1$H NMR (CDCl$_3$ 400 MHz): δ 8.04-8.02 (m, 2H), 7.89-7.84 (m, 2H), 7.65-7.63 (m, 1H), 7.35-7.33 (m, 2H), 6.91-6.89 (m, 1H), 6.74 (s, 1H), 3.97 (s, 2H), 3.34 (s, 3H), 3.15-3.12 (m, 1H), 1.40 (d, J=7.2 Hz, 6H). LC-MS: $t_R$=2.062 min (Method C), m/z=377.0 [M+H]$^+$.

Example 22

6-(4-(6-fluoropyridin-2-yl)benzyl)-7-methyl-3-propylimidazo[1,5-a]pyrazin-8(7H)-one

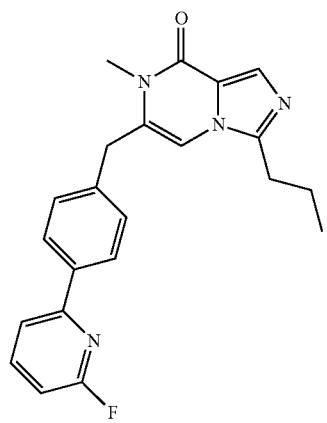 [SMILES: CCCc1ncc2c(=O)n(C)c(Cc3ccc(-c4cccc(F)n4)cc3)cn12]

Example 22 was prepared in a manner similar to example 21 from 6-(4-(6-fluoropyridin-2-yl)benzyl)-3-propylimidazo[1,5-a]pyrazin-8(7H)-one and methyl iodide. $^1$H NMR (CDCl$_3$ 400 MHz): δ 8.02 (d, J=8.4 Hz, 2H), 7.89-7.86 (m, 2H), 7.64 (dd, J=2.4, 7.2 Hz, 1H), 7.34 (d, J=8.4 Hz, 2H), 6.90 (dd, J=3.2, 8.0 Hz, 1H), 6.72 (s, 1H), 3.97 (s, 2H), 3.34 (s, 3H), 2.81 (t, J=7.6 Hz, 2H), 1.88-1.82 (m, 2H), 1.01 (t, J=7.2 Hz, 3H). LC-MS: $t_R$=2.148 min (Method C), m/z=377.0 [M+H]$^+$.

Example 23

3-ethyl-6-(4-(6-fluoropyridin-2-yl)benzyl)-7-methyl-imidazo[1,5-a]pyrazin-8(7H)-one

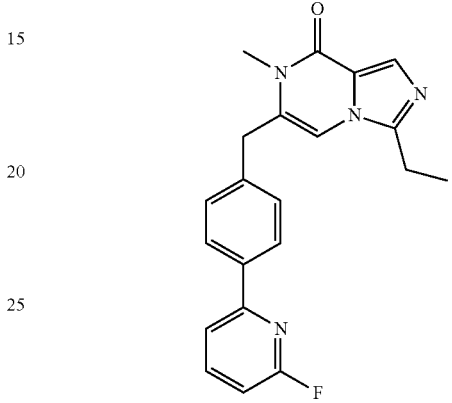

Example 23 was prepared in a manner similar to example 21 from 3-ethyl-6-(4-(6-fluoropyridin-2-yl)benzyl)imidazo[1,5-a]pyrazin-8(7H)-one and methyl iodide. $^1$H NMR (CDCl$_3$ 400 MHz): δ 8.02 (d, J=8.4 Hz, 2H), 7.88-7.84 (m, 2H), 7.63 (dd, J=2.4, 7.6 Hz, 1H), 7.34 (d, J=8.0 Hz, 2H), 6.90 (dd, J=2.8, 8.0 Hz, 1H), 6.70 (s, 1H), 3.97 (s, 2H), 3.34 (s, 3H), 2.84 (q, J=7.6 Hz, 2H), 1.41 (t, J=7.6 Hz, 3H). LC-MS: $t_R$=2.03 min (Method C), m/z=363.0 [M+H]$^+$.

Example 24

7-methyl-6-(4-(pyrazin-2-yl)benzyl)-3-(tetrahydro-2H-pyran-4-yl)imidazo[1,5-a]pyrazin-8(7H)-one

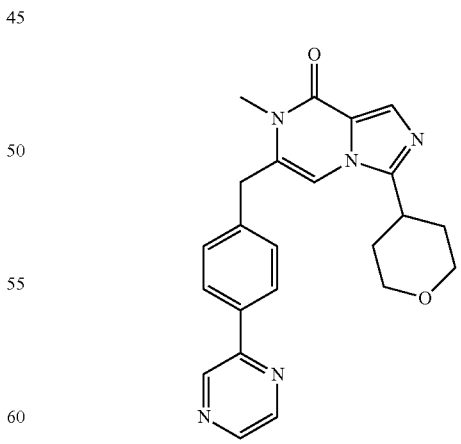

Example 24 was prepared in a manner similar to example 15 from 6-(4-bromobenzyl)-3-(3,6-dihydro-2H-pyran-4-yl)-7-methylimidazo[1,5-a]pyrazin-8(7H)-one and 2-(trimethylstannyl)pyrazine. $^1$H NMR (CDCl$_3$ 400 MHz): δ 9.04 (d, J=1.2 Hz, 1H), 8.66-8.65 (m, 1H), 8.55 (d, J=2.0 Hz, 1H), 8.04 (d, J=8.0 Hz, 2H), 7.91 (s, 1H), 7.39 (d, J=8.4 Hz, 2H), 6.84 (s, 1H), 4.13-4.11 (m, 2H), 4.00 (s, 2H), 3.57 (dt, J=2.0, 11.6 Hz, 2H), 3.33 (s, 3H), 3.12-3.07 (m, 1H), 2.15-2.11 (m, 2H), 1.91-1.88 (m, 2H). LC-MS: $t_R$=1.84 min (Method C), m/z=402.0 [M+H]$^+$.

Example 25

6-(4-(6-fluoropyridin-2-yl)benzyl)-7-methyl-3-(2,2,2-trifluoroethyl)imidazo[1,5-a]pyrazin-8(7H)-one

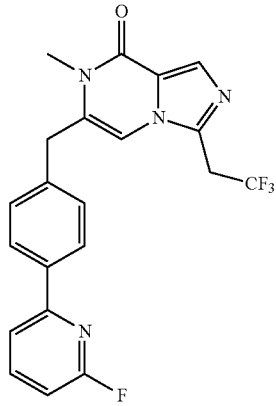 [SMILES: Cn1c(Cc2ccc(-c3cccc(F)n3)cc2)cn2c(CC(F)(F)F)ncc2c1=O]

Example 25 was prepared in a manner similar to example 21 from 6-(4-(6-fluoropyridin-2-yl)benzyl)-3-(2,2,2-trifluoroethyl)imidazo[1,5-a]pyrazin-8(7H)-one and methyl iodide. $^1$H NMR (CDCl$_3$ 400 MHz): δ 8.03 (d, J=8.3 Hz, 2H), 7.96 (s, 1H), 7.90-7.84 (m, 1H), 7.64 (dd, J=2.4, 7.4 Hz, 1H), 7.33 (d, J=8.3 Hz, 2H), 6.90 (dd, J=2.8, 8.0 Hz, 1H), 6.79 (s, 1H), 3.98 (s, 2H), 3.77 (q, J=10.0 Hz, 2H), 3.37 (s, 3H). LC-MS: $t_R$=2.671 min (Method C), m/z=417.0 [M+H]$^+$.

Example 26

7-methyl-6-(4-(pyrimidin-4-yl)benzyl)-3-(tetrahydro-2H-pyran-4-yl)imidazo[1,5-a]pyrazin-8(7H)-one

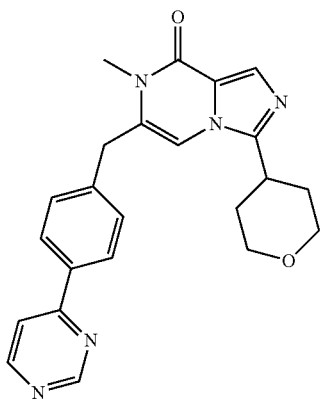 [SMILES: Cn1c(Cc2ccc(-c3ccncn3)cc2)cn2c(C3CCOCC3)ncc2c1=O]

Example 26 was prepared in a manner similar to example 15 from 6-(4-bromobenzyl)-3-(3,6-dihydro-2H-pyran-4-yl)-7-methylimidazo[1,5-a]pyrazin-8(7H)-one and 4-(trimethylstannyl)pyrimidine. $^1$H NMR (CDCl$_3$ 400 MHz): δ 9.28 (d, J=1.2, 1H), 8.79 (d, J=4.2 Hz, 1H), 8.11 (d, J=8.4 Hz, 2H), 7.91 (s, 1H), 7.71 (dd, J=1.2, 4.0 Hz, 1H), 7.38 (d, J=8.4 Hz, 2H), 6.83 (s, 1H), 4.13-4.10 (m, 2H), 4.00 (s, 2H), 3.59-3.53 (m, 2H), 3.12 (s, 3H), 3.12-3.06 (m, 1H), 2.18-2.08 (m, 2H), 1.90-1.86 (m, 2H). LC-MS: $t_R$=1.859 min (Method C), m/z=402.0 [M+H]$^+$.

Example 27

6-(4-(6-fluoropyridin-2-yl)benzyl)-7-methyl-3-(tetrahydrofuran-3-yl)imidazo[1,5-a]pyrazin-8(7H)-one, Isomer 1

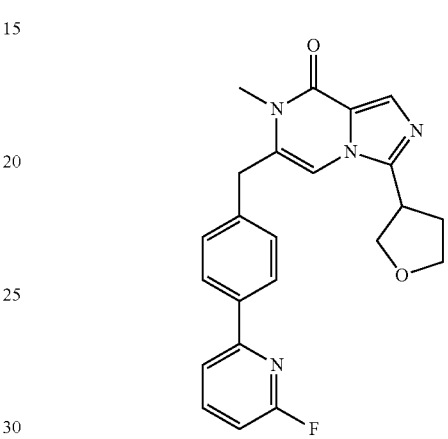

Example 27 was prepared in a manner similar to example 21 from 6-(4-(6-fluoropyridin-2-yl)benzyl)-3-(tetrahydrofuran-3-yl)imidazo[1,5-a]pyrazin-8(7H)-one and methyl iodide. And the two enantiomers were separated on preparative SFC and HPLC. $^1$H NMR (CDCl$_3$ 400 MHz): δ 8.03 (d, J=8.4 Hz, 2H), 7.92-7.83 (m, 2H), 7.64 (dd, J=1.9, 7.6 Hz, 1H), 7.34 (d, J=8.4 Hz, 2H), 6.91 (dd, J=2.9, 7.9 Hz, 1H), 6.76 (s, 1H), 4.19-4.13 (m, 1H), 4.10-3.91 (m, 5H), 3.62 (quin, J=7.6 Hz, 1H), 3.36 (s, 3H), 2.38 (q, J=7.5 Hz, 2H). LC-MS: $t_R$=2.302 min (Method C), m/z=405.0 [M+H]$^+$. SFC-MS: $t_R$=3.724 min. ee %=100%. [α]$_D^{20}$+6.0 (c=0.20, MeOH).

Example 28

6-(4-(6-fluoropyridin-2-yl)benzyl)-7-methyl-3-(tetrahydrofuran-3-yl)imidazo[1,5-a]pyrazin-8(7H)-one, Isomer 2

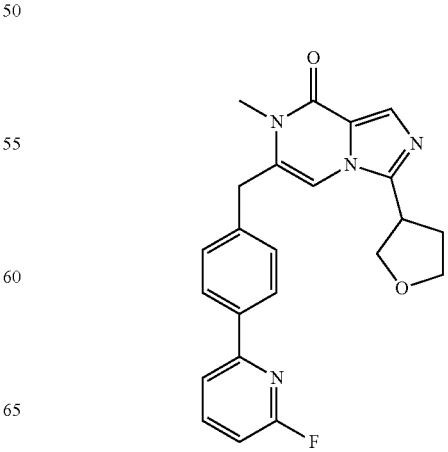

Example 28 was prepared in a manner similar to example 21 from 6-(4-(6-fluoropyridin-2-yl)benzyl)-3-(tetrahydrofuran-3-yl)imidazo[1,5-a]pyrazin-8(7H)-one and methyliodide. And the two enantiomers were separated on preparative SFC and HPLC. $^1$H NMR (CDCl$_3$ 400 MHz): δ 8.03 (d, J=8.4 Hz, 2H), 7.91-7.83 (m, 2H), 7.64 (dd, J=2.1, 7.6 Hz, 1H), 7.34 (d, J=8.2 Hz, 2H), 6.91 (dd, J=2.9, 7.9 Hz, 1H), 6.76 (s, 1H), 4.19-4.13 (m, 1H), 4.10-3.91 (m, 5H), 3.62 (quin, J=7.7 Hz, 1H), 3.36 (s, 3H), 2.38 (q, J=7.4 Hz, 2H). LC-MS: t$_R$=2.286 min (Method C), m/z=405.0 [M+H]$^+$. SFC: t$_R$=4.031 min. ee %=95.54%. [α]$_D^{20}$ −6.0 (c=0.20, MeOH).

Example 29

6-(4-(6-fluoropyridin-2-yl)benzyl)-7-methyl-3-(2-methyltetrahydrofuran-3-yl)imidazo[1,5-a]pyrazin-8(7H)-one, Isomer 1

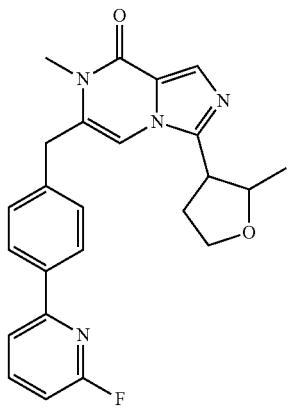 [SMILES: CC1OCCC1c1ncc2c(=O)n(C)c(Cc3ccc(-c4cccc(F)n4)cc3)cn12]

Example 29 was prepared in a manner similar to example 21 from 6-(4-(6-fluoropyridin-2-yl)benzyl)-3-(2-methyltetrahydrofuran-3-yl)imidazo[1,5-a]pyrazin-8(7H)-one and methyliodide. And the stereoisomers were separated by SFC. $^1$H NMR (CDCl$_3$ 400 MHz): δ 8.03 (d, J=8.4 Hz, 2H), 7.91-7.85 (m, 2H), 7.64 (dd, J=2.0, 7.6 Hz, 1H), 7.34 (d, J=8.0 Hz, 2H), 6.91 (dd, J=2.8, 8.0 Hz, 1H), 6.70 (s, 1H), 4.23-4.18 (m, 1H), 4.09-4.02 (m, 2H), 3.97 (s, 2H), 3.37 (s, 3H), 3.02 (q, J=8.4 Hz, 1H), 2.44-2.38 (m, 2H), 1.29 (d, J=6.0 Hz, 3H). LC-MS: t$_R$=2.33 min (Method C), m/z=419.0 [M+H]$^+$. SFC-MS: t$_R$=5.58 min, ee %=100%. [α]$_D^{20}$ +5.0 (c=0.20, dichloromethane).

Example 30 6-(4-(6-fluoropyridin-2-yl)benzyl)-7-methyl-3-(2-methyltetrahydrofuran-3-yl)imidazo[1,5-a]pyrazin-8(7H)-one, Isomer 2

Example 30 was prepared in a manner similar to example 21 from 6-(4-(6-fluoropyridin-2-yl)benzyl)-3-(2-methyltetrahydrofuran-3-yl)imidazo[1,5-a]pyrazin-8(7H)-one and methyl iodide. And the stereoisomers were separated by SFC. $^1$H NMR (CDCl$_3$ 400 MHz): δ 8.03 (d, J=8.4 Hz, 2H), 7.91-7.87 (m, 2H), 7.64 (dd, J=2.4, 7.6 Hz, 1H), 7.34 (d, J=8.0 Hz, 2H), 6.90 (dd, J=3.2, 8.0 Hz, 1H), 6.77 (s, 1H), 4.25-4.19 (m, 2H), 3.96 (s, 2H), 3.85-3.81 (m, 1H), 3.66-3.64 (m, 1H), 3.37 (s, 3H), 2.68-2.63 (m, 1H), 2.43-2.38 (m, 1H), 0.87 (d, J=6.4 Hz, 3H). LC-MS: t$_R$=2.25 min (Method C), m/z=419.0 [M+H]$^+$. SFC-MS: t$_R$=5.67 min, ee %=100%. [α]$_D^{20}$ −139.0 (c=0.20, dichloromethane).

Example 31

6-(4-(6-fluoropyridin-2-yl)benzyl)-7-methyl-3-(2-methyltetrahydrofuran-3-yl)imidazo[1,5-a]pyrazin-8(7H)-one, Isomer 3

Example 31 was prepared in a manner similar to example 21 from 6-(4-(6-fluoropyridin-2-yl)benzyl)-3-(2-methyltetrahydrofuran-3-yl)imidazo[1,5-a]pyrazin-8(7H)-one and methyliodide. And the stereoisomers were separated by SFC. $^1$H NMR (CDCl$_3$ 400 MHz): δ 8.03 (d, J=8.4 Hz, 2H), 7.92-7.87 (m, 2H), 7.64 (dd, J=2.0, 7.6 Hz, 1H), 7.34 (d, J=8.0 Hz, 2H), 6.91 (dd, J=2.8, 7.6 Hz, 1H), 6.70 (s, 1H), 4.23-4.18 (m, 1H), 4.08-4.02 (m, 2H), 3.97 (s, 2H), 3.37 (s, 3H), 3.02 (q, J=8.8 Hz, 1H), 2.44-2.38 (m, 2H), 1.29 (d, J=6.0 Hz, 3H). LC-MS: $t_R$=2.34 min (Method C), m/z=419.0 [M+H]$^+$. SFC-MS: $t_R$=5.99 min, ee %=99.23%. $[\alpha]_D^{20}$ −17.0 (c=0.20, dichloromethane).

Example 32

6-(4-(6-fluoropyridin-2-yl)benzyl)-7-methyl-3-(2-methyltetrahydrofuran-3-yl)imidazo[1,5-a]pyrazin-8(7H)-one, Isomer 4

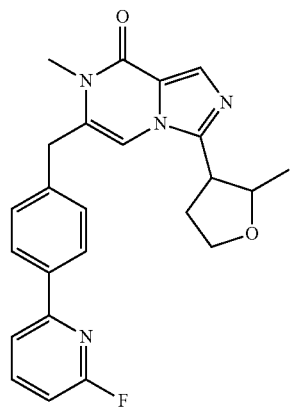 [SMILES: CC1OCCC1c1ncc2c(=O)n(C)c(Cc3ccc(-c4cccc(F)n4)cc3)cn12]

Example 32 was prepared in a manner similar to example 21 from 6-(4-(6-fluoropyridin-2-yl)benzyl)-3-(2-methyltetrahydrofuran-3-yl)imidazo[1,5-a]pyrazin-8(7H)-one and methyl iodide. And the stereoisomers were separated by SFC. $^1$H NMR (CDCl$_3$ 400 MHz): δ 8.03 (d, J=8.4 Hz, 2H), 7.91-7.87 (m, 2H), 7.64 (dd, J=2.8, 7.6 Hz, 1H), 7.33 (d, J=8.0 Hz, 2H), 6.90 (dd, J=3.2, 8.0 Hz, 1H), 6.77 (s, 1H), 4.25-4.19 (m, 2H), 3.96 (s, 2H), 3.85-3.81 (m, 1H), 3.66-3.64 (m, 1H), 3.37 (s, 3H), 2.68-2.63 (m, 1H), 2.43-2.38 (m, 1H), 0.87 (d, J=6.4 Hz, 3H). LC-MS: $t_R$=2.25 min (Method C), m/z=419.0 [M+H]$^+$. SFC-MS: $t_R$=6.84 min, ee %=100%. $[\alpha]_D^{20}$+103.0 (c=0.20, dichloromethane).

In Vitro Testing

PDE1 Inhibition Assay

PDE1A, PDE1B and PDE1C assays were performed as follows: the assays were performed in 60 µL samples containing a fixed amount of the PDE1 enzyme (sufficient to convert 20-25% of the cyclic nucleotide substrate), a buffer (50 mM HEPES (4-(2-hydroxyethyl)-1-piperazineethanesulfonic acid) pH 7.6; 10 mM MgCl$_2$; 0.02% Tween20), 0.1 mg/ml BSA (bovine serum albumin), 15 nM tritium labelled cAMP and varying amounts of inhibitors. Reactions were initiated by addition of the cyclic nucleotide substrate, and reactions were allowed to proceed for 1 hr at room temperature before being terminated through mixing with 20 µL (0.2 mg) yttrium silicate SPA beads (PerkinElmer). The beads were allowed to settle for 1 hour in the dark before the plates were counted in a Wallac 1450 Microbeta counter. The measured signals were converted to activity relative to an uninhibited control (100%) and IC$_{50}$ values were calculated using XlFit (model 205, IDBS).

PDE9 Inhibition Assay

A PDE9 assay may for example, be performed as follows: The assay is performed in 60 µL samples containing a fixed amount of the relevant PDE enzyme (sufficient to convert 20-25% of the cyclic nucleotide substrate), a buffer (50 mM HEPES pH 7.6; 10 mM MgCl$_2$; 0.02% Tween20), 0.1 mg/ml BSA, 225 pCi of $^3$H-labelled cyclic nucleotide substrate, tritium labeled cAMP to a final concentration of 5 nM and varying amounts of inhibitors. Reactions are initiated by addition of the cyclic nucleotide substrate, and reactions are allowed to proceed for one hr at room temperature before being terminated through mixing with 15 µL 8 mg/mL yttrium silicate SPA beads (Amersham). The beads are allowed to settle for one hr in the dark before the plates are counted in a Wallac 1450 Microbeta counter. The measured signal can be converted to activity relative to an uninhibited control (100%) and IC$_{50}$ values can be calculated using the Xlfit extension to EXCEL.

In the context of the present invention the assay was performed in 60 µL assay buffer (50 mM HEPES pH 7.6; 10 mM MgCl$_2$; 0.02% Tween20) containing enough PDE9 to convert 20-25% of 10 nM $^3$H-cAMP, and $^3$H-labelled cGMP to a final concentration of 15 nM, and 10 µM of inhibitor. Following 1 hr incubation the reactions were terminated by addition of 15 µL 8 mg/mL yttrium silicate SPA beads (Amersham). The beads were allowed to settle for one hr in the dark before the plates were counted in a Wallac 1450 Microbeta counter.

The invention claimed is:
1. A compound according to formula (I)

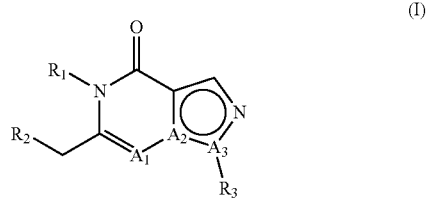

wherein
A$_1$ is N, A$_2$ is C and A$_3$ is N; or
A$_1$ is C, A$_2$ is C and A$_3$ is N; or
A$_1$ is C, A$_2$ is N and A$_3$ is C;
R$_1$ is hydrogen, or linear or branched C$_1$-C$_8$ alkyl; or
R$_1$ is methyl substituted with phenyl, wherein said phenyl is optionally substituted one or more times with one or more substituents selected from the group consisting of halogen, C$_1$-C$_3$ alkyl, fluoromethyl, difluoromethyl, trifluoromethyl, methoxy, difluoromethoxy and trifluoromethoxy;
R$_2$ is phenyl which is substituted in the 4-position with phenyl or with a heteroaromatic group; wherein said phenyl substituent or said heteroaromatic group can be substituted one or more times with one or more substituents selected from the group consisting of methyl, fluoromethyl, difluoromethyl, trifluoromethyl, halogen, hydroxy, cyano, methoxy, difluoromethoxy and trifluoromethoxy; or
R$_2$ is piperazin-1-yl which is substituted in the 4-position with phenyl or with a heteroaromatic group; wherein said phenyl substituent or said heteroaromatic group can be substituted one or more times with one or more substituents selected from the group consisting of methyl, fluoromethyl, difluoromethyl, trifluoromethyl, halogen, hydroxy, cyano, methoxy, difluoromethoxy and trifluoromethoxy;
R$_3$ is selected from the group consisting of linear or branched C$_2$-C$_8$ alkyl, saturated monocyclic C$_3$-C$_8$ cycloalkyl, oxetanyl, tetrahydrofuranyl, and tetrahydropyranyl; all of which can be substituted one or more times with one or more substituents selected from the group consisting of methyl, fluorine, hydroxy, cyano and methoxy;

or a pharmaceutically acceptable salt thereof.

2. The compound according to claim 1, wherein $A_1$ is N, $A_2$ is C and $A_3$ is N, or a pharmaceutically acceptable salt thereof.

3. The compound according to claim 1, wherein $A_1$ is C, $A_2$ is C and $A_3$ is N, or a pharmaceutically acceptable salt thereof.

4. The compound according to claim 1, wherein $A_1$ is C, $A_2$ is N and $A_3$ is C, or a pharmaceutically acceptable salt thereof.

5. The compound of claim 1, wherein $R_1$ is selected from methyl and ethyl, or a pharmaceutically acceptable salt thereof.

6. The compound of claim 1, wherein $R_1$ is methyl substituted with phenyl, wherein said phenyl can be substituted one time with methoxy, or a pharmaceutically acceptable salt thereof.

7. The compound of claim 1, wherein $R_2$ is phenyl which is substituted in the 4-position with phenyl or with pyridinyl; wherein said phenyl substituent or said pyridinyl can be substituted one or more times with one or more substituents selected from the group consisting of methyl, fluoromethyl, halogen, hydroxy, cyano and methoxy, or a pharmaceutically acceptable salt thereof.

8. The compound of claim 1, wherein $R_2$ is piperazin-1-yl which is substituted in the 4-position with phenyl or with pyridinyl; wherein said phenyl substituent or said pyridinyl can be substituted one or more times with one or more substituents selected from the group consisting of methyl, fluoromethyl, halogen, hydroxy, cyano and methoxy, or a pharmaceutically acceptable salt thereof.

9. The compound according to claim 8, wherein said heteroaromatic group is 2-pyridinyl, or a pharmaceutically acceptable salt thereof.

10. The compound of claim 7, wherein said one or more substituents are selected from methyl, fluoromethyl, difluoromethyl, trifluoromethyl, fluorine, methoxy, difluoromethoxy and trifluoromethoxy, or a pharmaceutically acceptable salt thereof.

11. The compound of claim 1, wherein $R_3$ is unsubstituted tetrahydropyranyl, or a pharmaceutically acceptable salt thereof.

12. The compound according to claim 1, wherein the compound is selected from the group consisting of:
1. 5-methyl-6-[[4-(6-methyl-2-pyridyl)phenyl]methyl]-1-tetrahydropyran-4-yl-pyrazolo [4,3-c]pyridin-4-one;
2. 5-methyl-6-[[4-(2-pyridyl)phenyl]methyl]-1-tetrahydropyran-4-yl-pyrazolo [3,4-d]pyrimidin-4-one;
3. 5-methyl-6-[[4-(6-methyl-2-pyridyl)phenyl]methyl]-1-tetrahydropyran-4-yl-pyrazolo [3,4-d]pyrimidin-4-one;
4. 6-[[4-(6-fluoro-2-pyridyl)phenyl]methyl]-5-methyl-1-tetrahydropyran-4-yl-pyrazolo[3,4-d]pyrimidin-4-one;
5. 6-[[4-(6-fluoro-2-pyridyl)phenyl]methyl]-5-methyl-1-tetrahydropyran-4-yl-pyrazolo[4,3-c]pyridin-4-one;
6. 5-methyl-6-[[4-(2-pyridyl)phenyl]methyl]-1-tetrahydropyran-4-yl-pyrazolo[4,3-c]pyridin-4-one;
7. 7-[(4-methoxyphenyl)methyl]-6-[[4-(2-pyridyl)piperazin-1-yl]methyl]-3-tetrahydropyran-4-yl-imidazo[1,5-a]pyrazin-8-one;
8. 7-[(4-methoxyphenyl)methyl]-6-[(4-phenylpiperazin-1-yl)methyl]-3-tetrahydropyran-4-yl-imidazo[1,5-a]pyrazin-8-one;
9. 7-[(4-methoxyphenyl)methyl]-6-[[4-(2-pyridyl)phenyl]methyl]-3-tetrahydropyran-4-yl-imidazo[1,5-a]pyrazin-8-one;
10. 6-[[4-(2-pyridyl)phenyl]methyl]-3-tetrahydropyran-4-yl-7H-imidazo[1,5-a]pyrazin-8-one;
11. 7-methyl-6-[[4-(2-pyridyl)phenyl]methyl]-3-tetrahydropyran-4-yl-imidazo[1,5-a]pyrazin-8-one;
12. 7-ethyl-6-[[4-(2-pyridyl)phenyl]methyl]-3-tetrahydropyran-4-yl-imidazo[1,5-a]pyrazin-8-one;
13. 7-methyl-6-[[4-(6-methyl-2-pyridyl)phenyl]methyl]-3-tetrahydropyran-4-yl-imidazo[1,5-a]pyrazin-8-one;
14. 6-[[4-(6-fluoro-2-pyridyl)phenyl]methyl]-7-methyl-3-tetrahydropyran-4-yl-imidazo[1,5-a]pyrazin-8-one;
15. 6-[[4-[6-(difluoromethyl)-2-pyridyl]phenyl]methyl]-7-methyl-3-tetrahydropyran-4-yl-imidazo[1,5-a]pyrazin-8-one;
16. 6-[[4-(6-methoxy-2-pyridyl)phenyl]methyl]-7-methyl-3-tetrahydropyran-4-yl-imidazo[1,5-a]pyrazin-8-one;
17. 6-[[4-(3-methoxy-2-pyridyl)phenyl]methyl]-7-methyl-3-tetrahydropyran-4-yl-imidazo[1,5-a]pyrazin-8-one;
18. 7-methyl-6-[[4-(o-tolyl)phenyl]methyl]-3-tetrahydropyran-4-yl-imidazo[1,5-a]pyrazin-8-one;
19. 7-methyl-6-[(4-phenylphenyl)methyl]-3-tetrahydropyran-4-yl-imidazo[1,5-a]pyrazin-8-one;
20. 7-methyl-6-(4-(1-methyl-1H-imidazol-4-yl)benzyl)-3-(tetrahydro-2H-pyran-4-yl)imidazo[1,5-a]pyrazin-8(7H)-one;
21. 6-[[4-(6-fluoro-2-pyridyl)phenyl]methyl]-3-isopropyl-7-methyl-imidazo[1,5-a]pyrazin-8-one;
22. 6-(4-(6-fluoropyridin-2-yl)benzyl)-7-methyl-3-propylimidazo[1,5-a]pyrazin-8(7H)-one;
23. 3-ethyl-6-(4-(6-fluoropyridin-2-yl)benzyl)-7-methyl-imidazo[1,5-a]pyrazin-8(7H)-one;
24. 7-methyl-6-(4-(pyrazin-2-yl)benzyl)-3-(tetrahydro-2H-pyran-4-yl)imidazo[1,5-a]pyrazin-8(7H)-one;
25. 6-(4-(6-fluoropyridin-2-yl)benzyl)-7-methyl-3-(2,2,2-trifluoroethyl)imidazo[1,5-a]pyrazin-8(7H)-one;
26. 7-methyl-6-(4-(pyrimidin-4-yl)benzyl)-3-(tetrahydro-2H-pyran-4-yl)imidazo[1,5-a]pyrazin-8(7H)-one;
27. 6-(4-(6-fluoropyridin-2-yl)benzyl)-7-methyl-3-(tetrahydrofuran-3-yl)imidazo[1,5-a]pyrazin-8(7H)-one, isomer 1;
28. 6-(4-(6-fluoropyridin-2-yl)benzyl)-7-methyl-3-(tetrahydrofuran-3-yl)imidazo[1,5-a]pyrazin-8(7H)-one, isomer 2;
29. 6-(4-(6-fluoropyridin-2-yl)benzyl)-7-methyl-3-(2-methyltetrahydrofuran-3-yl)imidazo[1,5-a]pyrazin-8(7H)-one, isomer 1;
30. 6-(4-(6-fluoropyridin-2-yl)benzyl)-7-methyl-3-(2-methyltetrahydrofuran-3-yl)imidazo[1,5-a]pyrazin-8(7H)-one, isomer 2;
31. 6-(4-(6-fluoropyridin-2-yl)benzyl)-7-methyl-3-(2-methyltetrahydrofuran-3-yl)imidazo[1,5-a]pyrazin-8(7H)-one, isomer 3;
32. 6-(4-(6-fluoropyridin-2-yl)benzyl)-7-methyl-3-(2-methyltetrahydrofuran-3-yl)imidazo[1,5-a]pyrazin-8(7H)-one, isomer 4;

or a pharmaceutically acceptable salt of any of these compounds.

13. A pharmaceutical composition comprising a therapeutically effective amount of a compound of claim 1, or a pharmaceutically acceptable salt thereof, and one or more pharmaceutically acceptable carriers, diluents or excipients.

14. A method for the treatment of a neurodegenerative disorder, or a psychiatric disorder, which method comprises the administration of a therapeutically effective amount of a compound of claim 1, or a pharmaceutically acceptable salt thereof, to a patient in need thereof.

15. The method of claim 14, wherein the neurodegenerative disorder is selected from the group consisting of Alzheimer's Disease, Parkinson's Disease and Huntington's Disease.

16. The method of claim 14, wherein the psychiatric disorder is selected from the group consisting of Attention Deficit Hyperactivity Disorder (ADHD), depression, anxiety, narcolepsy, cognitive impairment and cognitive impairment associated with schizophrenia (CIAS), and restless leg syndrome.

* * * * *